US012606842B2

(12) United States Patent
Simon et al.

(10) Patent No.: US 12,606,842 B2
(45) Date of Patent: *Apr. 21, 2026

(54) PLANT VECTORS, COMPOSITIONS AND USES RELATING THERETO

(71) Applicants: University of Maryland, College Park, College Park, MD (US); The Regents of the University of California, Oakland, CA (US)

(72) Inventors: Anne Elizabeth Simon, Bowie, MD (US); Jingyuan Liu, College Park, MD (US); Georgios Vidalakis, Riverside, CA (US); Sohrab Bodaghi, Laguna Niguel, CA (US)

(73) Assignees: University of Maryland, College Park; The Regents of the University of California

( * ) Notice: Subject to any disclaimer, the term of this patent is extended or adjusted under 35 U.S.C. 154(b) by 227 days.

This patent is subject to a terminal disclaimer.

(21) Appl. No.: 17/291,431

(22) PCT Filed: Nov. 12, 2019

(86) PCT No.: PCT/US2019/060945
§ 371 (c)(1),
(2) Date: May 5, 2021

(87) PCT Pub. No.: WO2020/102210
PCT Pub. Date: May 22, 2020

(65) Prior Publication Data
US 2022/0002746 A1 Jan. 6, 2022

Related U.S. Application Data

(60) Provisional application No. 62/760,098, filed on Nov. 13, 2018.

(51) Int. Cl.
*C12N 15/82* (2006.01)
*A01N 63/60* (2020.01)
*C12N 15/64* (2006.01)

(52) U.S. Cl.
CPC ......... *C12N 15/8281* (2013.01); *A01N 63/60* (2020.01); *C12N 15/64* (2013.01); *C12N 15/8218* (2013.01)

(58) Field of Classification Search
CPC ............................ C12N 15/8281; C12N 15/64
See application file for complete search history.

(56) References Cited

U.S. PATENT DOCUMENTS

| | | | |
|---|---|---|---|
| 5,304,731 A | 4/1994 | Masuta et al. | |
| 7,217,854 B1 * | 5/2007 | Baulcombe ........ | C12N 15/8218 800/278 |
| 8,389,804 B2 | 3/2013 | Dawson et al. | |
| 2006/0127364 A1 | 6/2006 | Christian et al. | |
| 2010/0017911 A1 | 1/2010 | Dawson et al. | |
| 2011/0288147 A1 | 11/2011 | Brown | |
| 2013/0212739 A1 | 8/2013 | Giritch et al. | |
| 2014/0296503 A1 | 10/2014 | Avniel et al. | |
| 2015/0096078 A1 | 4/2015 | Dawson et al. | |
| 2015/0315604 A1 * | 11/2015 | Giritch ............... | C12N 15/8257 800/288 |
| 2017/0044560 A1 | 2/2017 | Paldi et al. | |
| 2018/0002682 A1 | 1/2018 | Sternberg et al. | |
| 2018/0235210 A1 | 8/2018 | Zeng et al. | |
| 2019/0093117 A1 | 3/2019 | Li et al. | |
| 2021/0324394 A1 | 10/2021 | Navarro et al. | |
| 2024/0002871 A1 | 1/2024 | Simon | |
| 2024/0381876 A1 | 11/2024 | Simon | |

FOREIGN PATENT DOCUMENTS

| | | | | |
|---|---|---|---|---|
| AU | 2016238902 B2 | 11/2018 | | |
| BR | 112015027022 A2 | 9/2017 | | |
| CN | 105567728 A | 5/2016 | | |
| CN | 115052979 A | 9/2022 | | |
| JP | 2007-518412 A | 7/2007 | | |
| JP | 2011-015640 A | 1/2011 | | |
| JP | 2013-532992 A | 8/2013 | | |
| JP | 2016-514465 A | 5/2016 | | |
| WO | WO-0005379 A1 * | 2/2000 | ........... | C07K 14/005 |
| WO | 2003087146 A2 | 10/2003 | | |
| WO | 2020035619 A1 | 2/2020 | | |
| WO | 2020051156 A1 | 3/2020 | | |
| WO | 2020102210 A1 | 5/2020 | | |
| WO | WO 2021/097086 | 5/2021 | | |

OTHER PUBLICATIONS

Kappagantu et al., 2020, Viral hacks of the plant vasculature: the role of phloem alterations in systemic virus infection. Annual review of virology, 7, 351-370. (Year: 2020).*
Thomas et al., 2003, Turnip crinkle virus coat protein mediates suppression of RNA silencing in Nicotiana benthamiana. Virology, 306(1), 33-41. (Year: 2003).*
Park et al., 2017, The use of a tobacco mosaic virus-based expression vector system in chrysanthemum. The Plant Pathology Journal, 33(4), 429. (Year: 2017).*
Liu et al., 2021, Translation and Movement of an Infectious Umbravirus-like RNA Citrus Yellow Vein Associated Virus (Doctoral dissertation, University of Maryland, College Park). (Year: 2021).*
Abdelhalek et al., 2018, A comparative analysis of the suppressor activity of Tobacco mosaic virus proteins in the tomato plant. Jordan J Biol Sci Short Commun, 11(4), 469-473. (Year: 2018).*

(Continued)

*Primary Examiner* — David H Kruse
*Assistant Examiner* — Santosh Sharma

(57) ABSTRACT

The present disclosure relates to a single stranded RNA vector suitable for introducing a therapeutic agent, such as a peptide, a protein or a small RNA, into a host plant. The vector does not encode for any movement protein or coat protein, but is capable of capable of systemic and phloem-limited movement and replication within the host plant.

28 Claims, 27 Drawing Sheets
Specification includes a Sequence Listing.

(56) References Cited

OTHER PUBLICATIONS

Kwon et al., 2021, Complete nucleotide sequence, genome organization, and comparative genomic analyses of citrus yellow-vein associated virus (CYVaV). Frontiers in Microbiology, 12, 683130. (Year: 2021).*

Definition of Vector by National Human Genome Research Institute (https://www.genome.gov/, Accessed Mar. 28, 2024) (Year: 2024).*

Weathers, L. G. (1960). Yellow-vein disease of citrus and studies of interactions between yellow-vein and other viruses of citrus. Virology, 11(4), 753-764. (Year: 1960).*

Ruiz, M.T. et al. (1998) "*Initiation And Maintenance Of Virus-Induced Gene Silencing*," Plant Cell 10(6):937-946.

Aguado, L.C. et al. (2017), "*RNase III nucleases from diverse kingdoms serve as antiviral effectors*", Nature 547:114-117.

Balachandran, S. et al. (1997), "*Phloem sap proteins from Cucurbita maxima and Ricinus communis have the capacity to traffic cell to cell through plasmodesmata*", PNAS 94(25):14150-14155.

Barratt et al. (2011), "*Callose Synthase GSL7 Is Necessary for Normal Phloem Transport and Inflorescence Growth in Arabidopsis*", Plant Physiol 155(1):328-341.

Bendix, C., and Lewis, J.D. (2018), "*The enemy within: phloem-limited pathogens*", Mo Plant Path 19:238-254.

Cadena-Nava, et al. (2012), "*Self-assembly of viral capsid protein and RNA molecules of different sizes: requirement for a specific high protein/RNA mass ratio*", J. Virol. 86:3318-3326.

Calderwood, A. et al. (2016), "*Transcript Abundance Explains mRNA Mobility Data in Arabidopsis thaliana*", Plant Cell 28:610-615.

Chen, X.Y. and Kim, J.Y. (2009), "*Callose synthesis in higher plants*", Plant Sig Behav 4(6):489-492.

Cheng, et al. (2015), "*Expressing p20 hairpin RNA of Citrus tristeza virus confers Citrus aurantium with tolerance/resistance against stem pitting and seedling yellow CTV strains*", J. Integrative Agriculture 14(9):1767-1777.

Chin, L.S. et al. (1993), "*The beet western yellows virus ST9-associated RNA shares structural and nucleotide sequence homology with Tombusviruses*", Virology 192(2):473-482.

Collum, T.D. et al. (2016), "*Tobacco mosaic virus-directed reprogramming of auxin/indole acetic acid protein transcriptional responses enhances virus phloem loading*", Proc Natl Acad Sci USA 113:E2740-E2749.

Deom, C.M. et al. (1987), "*The 30-kilodalton gene product of tobacco mosaic virus potentiates virus movement*", Science (New York, NY) 237:389-394.

Enrique et al. (2011), "*Novel demonstration of RNAi in citrus reveals importance of citrus callose synthase in defense against Xanthomonas citri subsp. Citri*", Plant Biotech J 9:394-407.

Folimonova, S.Y. and Tilsner, J. (2018), "*Hitchhikers, highway tolls and roadworks: the interactions of plant viruses with the phloem*", Curr Opin Plant Biol 43:82-88.

Gao, F. and Simon, A.E. (2017), "*Differential use of 3' CITEs by the subgenomic RNA of Pea enation mosaic virus 2*", Virology 510:194-204.

Gaupels, F. et al. (2008), "*Nitric oxide generation in Vicia faba phloem cells reveals them to be sensitive detectors as well as possible systemic transducers of stress signals*", New Phytol 178:634-646.

GenBank Accession JX101610, "*Citrus yellow vein-associated virus isolate YV920, complete genome*", Jul. 31, 2013.

Gómez, G. and Pallás, V. (2004), "*A long-distance translocatable phloem protein from cucumber forms a ribonucleoprotein complex in vivo with Hop stunt viroid RNA*", J Virol 78(18):10104-10110.

Gómez, G. et al. (2005), "*Identification of translocatable RNA-binding phloem proteins from melon, potential components of the long-distance RNA transport system*", Plant J 41:107-116.

Ham, B.K. and Lucas, W.J. (2017), "*Phloem-Mobile RNAs as Systemic Signaling Agents*", Annual Rev Plant Biol 68:173-195.

Ham, B.K. et al. (2009), "*A polypyrimidine tract binding protein, pumpkin RBP50, forms the basis of a phloem-mobile ribonucleoprotein complex*", Plant Cell 21:197-215.

Heinlein, M. (2015), "*Plant virus replication and movement*", Virology 479:657-671.

International Search Report PCT/US2019/060945 (WO 2020/102210) (2020) (5 pages).

International Search Report PCT/US2020/060228 (WO 2021/097086) (2021) (4 pages).

Jia, et al. (2014), "*Xcc-facilitated agroinfiltration of citrus leaves: a tool for rapid functional analysis of transgenes in citrus leaves*", Plant Cell Rep. 33:1993-2001.

Kim, G. et al. (2014), "*Genomic-scale exchange of mRNA between a parasitic plant and its hosts*", Science 345:808-811.

Kim, M. et al. (2001), "*Developmental changes due to long-distance movement of a homeobox fusion transcript in tomato*", Science (New York, NY) 293:287-289.

Koh, H. et al. (2012). "*Silent Information Regulator 2 (Sir2) and Forkhead Box O (FOXO) Complement Mitochondrial Dysfunction and Dopaminergic Neuron Loss in Drosophila PTEN-induced Kinase 1 (PINK1) Null Mutant*", J Biol Chem 287(16):12750-12758.

Lee, J.Y. and Frank, M. (2018), "*Plasmodesmata in phloem: different gateways for different cargoes*", Curr Opin Plant Biol 43:119-124.

May, et al. (2020), "*The Multifunctional Long-Distance Movement Protein of Pea Enation Mosaic Virus 2 Protects Viral and Host Transcripts from Nonsense-Mediated Decay*", mBio 11:300204-20.

Morris, R.J. (2018), "*On the selectivity, specificity and signaling potential of the long-distance movement of messenger RNA*", Curr Opin Plant Biol 43:1-7.

Pallas, V. and Gomez, G. (2013), "*Phloem RNA-binding proteins as potential components of the long-distance RNA transport system*", Front Plant Sci 4:130.

Passmore, B.K. et al. (1993), "*Beet western yellows virus-associated RNA: an independently replicating RNA that stimulates virus accumulation*", PNAS 90(31):10168-10172.

Quito-Avila, D.F. et al. (2015), "*Detection and partial genome sequence of a new umbra-like virus of papaya discovered in Ecuador*", Eur J Plant Pathol 143:199-204.

Ryabov, E.V. et al. (2001), "*Umbravirus-encoded proteins both stabilize heterologous viral RNA and mediate its systemic movement in some plant species*", Virology 288:391-400.

Schoelz, J.E. et al. (2011), "*Intracellular transport of plant viruses: finding the door out of the cell*", Mol Plant 4:813-831.

Senthil-Kumar et al. (2008), "*Virus-induced gene silencing and its application in characterizing genes involved in water-deficit-stress tolerance*", J Plant Physiol 165(13):1404-1421.

Singla-Rastogi, et al. (2019), "*Plant small RNA species direct gene silencing in pathogenic bacteria as well as disease protection*", Preprint posted to bioRxiv (47 pages).

Thieme, C.J. et al. (2015), "*Endogenous Arabidopsis messenger RNAs transported to distant tissues*", Nature Plants 1(4):15025.

Tilsner, J. (2014), "*Techniques for RNA in vivo imaging in plants*", J Microscopy 258(1):1-5.

Turgeon, R. and Wolf, S. (2009), "*Phloem Transport: Cellular Pathways and Molecular Trafficking*", Ann Rev Plant Biol 60:207-221.

Weathers, L. (1957), "*A vein-yellowing disease of citrus caused by a graft-transmissible virus*", Plant Disease Reporter 41:741-742.

Weathers, L.G. (1960), "*Yellow-vein disease of citrus and studies of interactions between yellow-vein and other viruses of citrus*", Virology 11:753-764.

Weathers, L.G. (1963), "*Use of synergy in identification of strain of Citrus yellow vein virus*", Nature 200:812-813.

Written Opinion of the International Searching Authority PCT/US2019/060945 (WO 2020/102210) (2020) (7 pages).

Written Opinion of the International Searching Authority PCT/US2020/060228 (WO 2021/097086) (2021) (7 pages).

Xia, C. et al. (2018), "*Elucidation of the Mechanisms of Long-Distance mRNA Movement in a Nicotiana benthamiana/Tomato Heterograft System*", Plant Physiol 177:745-758.

Xie et al. (2011), "*CalS7 encodes a callose synthase responsible for callose deposition in the phloem*", Plant J 65(1):1-14.

(56)        References Cited

OTHER PUBLICATIONS

Xoconostle-Cazares, B. et al. (1999), *"Plant paralog to viral movement protein that potentiates transport of mRNA into the phloem"*, Science (New York, NY) 283:94-98.

Yang, Y. et al. (2015), *"Messenger RNA exchange between scions and rootstocks in grafted grapevines"*, BMC Plant Biol 15, 251.

Yoo, B.C. et al. (2004), *"A systemic small RNA signaling system in plants"*, Plant Cell 16:1979-2000.

Zhang, W.N. et al. (2016), *"tRNA-Related Sequences Trigger Systemic mRNA Transport in Plants"*, Plant Cell 28:1237-1249.

Japanese Patent Application No. 2021-549930, Office Action dated Oct. 17, 2023.

Indonesian Patent Application No. P00202104029, Office Action dated Dec. 13, 2022.

European Patent Application No. 19884145.4, Extended European Search Report dated Jul. 21, 2022.

Zaidi, S. et al., "Viral Vectors for Plant Genome Engineering", Frontiers in Plant Science, vol. 8, Apr. 11, 2017, pp. 1-6.

Hefferon, K. "Plant Virus Expression Vector Development: New Perspectives", Biomed Research International, vol. 2014, Jan. 1, 2014. pp. 1-6.

Kwon, S. et al., "Complete Nucleotide Sequence, Genome Organization, and Comparative Genomic Analyses of Citrus Yellow-Vein Associated Virus (CYVaV)", Frontiers in Microbiology, vol. 12, Jun. 8, 2021, pp. 1-12.

Chilean Patent Application No. 01254-2021, Office Action dated May 19, 2023.

Duan et al., "Complete genome sequence of citrus huanglongbing bacterium, 'Candidatus Liberibacter asiaticus' obtained through metagenomics," Molecular Plant-Microbe Interactions, 22(8), 1011-1020, 2009.

Luck et al., "siRNA-Finder (si-Fi) software for RNAi-target design and off-target prediction", Frontiers in Plant Science, 10, 1023, 2019.

Oxford learner's dictionary meaning of word "effective". https://www.oxfordlearnersdictionaries.com/definition/english/effective. (accessed May 18, 2023).

U.S. Appl. No. 17/317,596, Restriction Requirement dated Jan. 4, 2023.

U.S. Appl. No. 17/317,596, Office Action dated May 24, 2023.

U.S. Appl. No. 17/317,596, Final Office Action dated Jan. 12, 2024.

European Patent Application No. 20886307.6, Supplementary Partial European Search Report dated Dec. 14, 2023.

Fagoaga, Carmen et al., "Post-Transcriptional Gene Silencing of the p23 Silencing Suppressor of Citrus tristeza virus Confers Resistance to the Virus in Transgenic Mexican Lime", Plant Molecular Biology, vol. 60, No. 2, Jan. 1, 2006, pp. 153-165.

Chilean Patent Application No. 01254-2021, Office Action dated Feb. 16, 2024.

European Patent Application No. 20886307.6, Extended European Search Report dated Mar. 6, 2024.

Japanese Patent Application No. 2021-549930, Office Action dated Jun. 14, 2024.

Bao, Y., et al., "Virus Classification by Pairwise Sequence Comparison (PASC)", Encyclopedia of Virology. 2008, pp. 342-348.

Chinese Patent Application No. 202080093354.9, Office Action dated Jun. 28, 2024.

Yao Lixiao et al., "Advances and strategies in citrus genetic engineering and breeding", Journal of Fruit Science, vol. 30, No. 6, Nov. 10, 2013, p.p. 1056-1064.

Chinese Patent Application No. 201980088371.0, Office Action dated Jun. 28, 2024.

Liu Qiyan, "Molecular identification and comparative genomic study of four closteroviruses isolated from wild citrus", China Master's Theses Full-text Database (Electronic Journal), Collection of Agricultural Science and Technology, Jan. 15, 2022, pp. 1-69.

U.S. Appl. No. 17/317,596, Office Action dated Aug. 14, 2024.

Japanese Patent Application No. 2021-549930, Office Action dated Dec. 3, 2024.

U.S. Appl. No. 17/775,822, Restriction Requirement dated Sep. 11, 2024.

U.S. Appl. No. 17/775,822, Office Aciton dated Dec. 17, 2024.

U.S. Appl. No. 17/317,596, Office Action dated Feb. 26, 2025.

U.S. Appl. No. 17/096,593, Office Action dated Mar. 3, 2025.

Mexican Patent Application No. MX/a/2021/005555, Office Action dated Jun. 3, 2025.

Korean Patent Application No. 10-2021-7017524, Office Action dated May 30, 2025.

* cited by examiner

A

B

CYVaV
(SEQ ID NOs:
17, 18 and 19)

PEMV2
(SEQ ID NO:25)

(SEQ ID NO: 2)

(A)              (B)

N. Benthamiana 16C (C)

Mock        +CYVaV

| Using Refolding Buffer | No Refolding Buffer (Negative Control) |

(A)                            (B)

NW    Ponceau        NW    Ponceau
      Staining               Staining

(A)

(B)

(C)

A

B

C

G 2250                                                                          2251

(SEQ ID NO: 26)

TAGGCCTCGACACGGGAAGGTAGCTGTCCCGGCACTGGGTTGCACATATTCGTGCCGACGCCAC

F            Local    Systemic

G 2301        (SEQ ID NO: 27)                    2302

CCGGCCTCGACACGGGAAGGTAGCTATTCGTGCCGACGCCGT

B          CYVaV-wt      +60      CYVaV-GDD

Insert in RdRp ORF

A (SEQ ID NO: 31)

(SEQ ID NO: 30)

(SEQ ID NO: 29)

GAAA/11nt
(SEQ ID NO: 28)

B (SEQ ID NO: 32)

Crystallography scaffold

C

Additional Insert(s) Location

Inserted into an RNA
(SEQ ID NO: 33

Lock sequence 1

SEQUENCE LISTING

<160> NUMBER OF SEQ ID NOS: 36

<210> SEQ ID NO 1
<211> LENGTH: 2692
<212> TYPE: RNA
<213> ORGANISM: Citrus Yellow Vein associated Virus (CYVaV)

<400> SEQUENCE: 1

```
ggguaaauau ggauccuuca ucuuugcccc gugccuguug gcaucaugcc agacaggugu      60
uucgagcauc aacuagcuuc ucaagagagg ugguucgcgc ugcucguaga uggguuacca     120
ugcccaccag ucgccaugca uaugacuuuu caacgagucu aggcauugug auugcugagc     180
cugcagcucg uuuacgacgc cgucugcccu cguacgaaa gugcgcagag aaguuaguag     240
uccacaagca agucgacacu uuggguggacg aauggugcuc uggaauuccc aacccugaua     300
ucguagaagu ugguugggca cuccgucuga gggaccguuu cggucuuccu cccgcuucug     360
agccuacccg gcucaguggu gagagauggg ugcucaaaca acucaauggg guagauccug     420
agucauggaa ugcugaucuu gguaggucag uucauaucca aggagacuac gccccaggga     480
ggaaugccca uaucgcucag gucgcggcga ccuugugguu aacuaggacc uugcaugaca     540
aggccuuggc ucgccaccag gguuuucgcg auuugcagug auuggggucg acgggcuaga     600
ggcaaaagca gugccucuag cuucuggacu ccgacugcuu ccgguuccgc gacccggaca     660
aagucgacga cugucucaga ccuuguuacu uccaacaccu cgugcucaau ucgugaauca     720
cgcgugcucg gcuaacaacc uuggacgugu gaugaccaca cguguguugc aguacaaggg     780
ccgagauccg auccuucccu cuucugaagc ccuucaccga cuuaaccuuc ggauagcuga     840
```

-continued

```
gcuauauagg ucuagaccuu cuaccgucua uccauuaagu uaugaagggu uucucaauug      900
cuaugaaggc cgacagcgua cucguuacgc ccaagccguc gagcaguuga ugcgguccac      960
ucuugagccg aaagaugcgc gaguugaaac guucauuaag aacgagaaau uugacugggc     1020
guugaaaggg gaggaggcug auccucgagc aauccaacca aggaagccga aauauuuggc     1080
ugagguugga cggugguuca aaccuuugga gcgaaucauc uacaaggauc ucaguaaaag     1140
guuguauggu gagggugcug agccguguau cgccaaaggc cuaaaugcau uagaaucugg     1200
agcgacuuug aggcgcaaau gggagaaguu uucuucucca guuugcguuu cucucgacgc     1260
uuccagguuc gaccugcaug uaagcguugg caugcuaaag uucacacaca agcuauauga     1320
cuauuacugu aagucuccca cucuccagcg cuaucucaaa uggacacucc gcaaccaugg     1380
cgucgccucc ugcaaagaau ugucauauga guaugagguu guuggccgga gaugagugg      1440 ugacauggac acugcauugg gcaacugcgu cauuaugucg auacuuacau gguuuaugcu     1500
uagugaacuu ggcauuaagc augaauuauu cgauaauggu gacgauugu uguucauuug      1560 cgagucucac gacgucccca gccccgaggu aauuacaaac ugguuuucgg acuuuggguu     1620
ugugguuagg uuggaaggcg ucacguccgu guuugagcgu auugaguuuu gccaaacuuc     1680
cccaguaugg acugagaggg guuggcugau guguaggaau auuaagucau ugaguaaaga     1740
ccuuacgaau guuaauucgu gcacgggcuc cacgauugaa uauacccacu gguugaaagc     1800 aguggggaaag ugcgggucaa uacucaaugc uggguuaccu auauuucagu ccuuucacaa     1860
caugcuggaa aggcuuggca cuaacucucg uauugaucga ggggguuuucu ucaaaucagg     1920 gcuaguuaau cucauucgug ggauggacag gcagccugac guugacauca cuacuuccgc     1980
ucggcuuucu uucgaagugg cauucgggau aacacccggg augcaauugg cuauugaacg     2040
guacuaugac ucugucaugg gcucgcugag uaaaauagaa acaacuaagu ggccaauuga     2100
acuaagaaag gaauacgaac acggaaguga gugguacgag gacuuaggcg uccuaggaug     2160
aauaggguca uugguuuacc gaugauaccu guucagaaua ggauugcucg agcuucguug     2220 guuagggguaa cucacauacc uucuuccaua acuggaaaag gucgugugag caaccuaacc     2280
aguuaaugua ggugucuuuc cguaucuagu cacgauggua agcaacccgu uuaucuguac     2340
ggcgcucacc cgugggguagg aaggugaagg uuuugugucc uuuaggucuu ggacagucug     2400
cgggcuuggg aacgacgccc cgcuagcaac guacugcucu ccuaccggac ugguagcuua     2460
auugucaucu uggagcgaua gcacuguggg ccucacccuu cgcgcguugg acguguugcg     2520
ugccccccac agauuuguga aacucuaugg agcaguuccg cgagccagaa gggaggaugg     2580
ccgccuggcg uaauccagga gcucuggggg gcuuguacuc agaguagcau ucugcuuuag     2640
acuguuaacu uuaugaacca cgcgugucac gugggggagag uuaacagcgc cc            2692
```

<210> SEQ ID NO 2
<211> LENGTH: 225
<212> TYPE: RNA
<213> ORGANISM: Citrus Yellow Vein associated Virus (CYVaV)
<220> FEATURE:
<221> NAME/KEY: misc_feature
<222> LOCATION: (1)..(225)
<223> OTHER INFORMATION: 3' End of CYVaV

<400> SEQUENCE: 2

```
ucuuggagcg auagcacugu gggccucacc cuucgcgcgu uggacguguu gcgugccccc       60
cacagauuug ugaaacucua uggagcaguu ccgcgagcca gaagggagga uggccgccug      120
gcguaaucca ggagcucugg ggggcuugua cucagaguag cauucugcuu uagacuguua      180
```

-continued acuuuaugaa ccacgcgugu cacguggggga gaguuaacag cgccc                       225

<210> SEQ ID NO 3
<211> LENGTH: 84
<212> TYPE: RNA
<213> ORGANISM: Citrus Yellow Vein associated Virus (CYVaV)
<220> FEATURE:
<221> NAME/KEY: misc_feature
<222> LOCATION: (1)..(84)
<223> OTHER INFORMATION: The 3' Cap Independent Translation Enhancer (3'
      CITE) of CYVaV

<400> SEQUENCE: 3
ucuuggagcg auagcacugu gggccucacc cuucgcgcgu uggacguguu gcgugccccc         60
cacagauuug ugaaacucua ugga                                               84

<210> SEQ ID NO 4

<400> SEQUENCE: 4

000

<210> SEQ ID NO 5

<400> SEQUENCE: 5

000

<210> SEQ ID NO 6
<211> LENGTH: 570
<212> TYPE: RNA
<213> ORGANISM: Citrus Yellow Vein associated Virus (CYVaV)
<220> FEATURE:
<221> NAME/KEY: misc_feature
<222> LOCATION: (1)..(570)
<223> OTHER INFORMATION: Polynucleotide Sequence of CYVaV Encoding
      Protein p21 (bases 9 to 578)

<400> SEQUENCE: 6
auggauccuu caucuuugcc ccgugccugu uggcaucaug ccagacaggu guuucgagca         60
ucaacuagcu ucucaagaga ggugguucgc gcugcucgua gauggguuac caugcccacc        120
agucgccaug cauaugacuu uucaacgagu cuaggcauug ugauugcuga gccugcagcu        180
cguuuacgac gccgucugcc cucuguacga aagugcgcag agaaguuagu aguccacaag        240
caagucgaca cuuuggugga cgaauggugc ucuggaauuc ccaacccuga uaucguagaa        300
guugguuggg cacuccgucu gagggaccgu uucggucuuc cucccgcuuc ugagccuacc        360
cggcucagug gugagagaug ggugcucaaa caacucaaug ggguagaucc ugagucaugg        420
aaugcugauc uugguagguc aguucauauc caaggagacu acgccccagg gaggaaugcc        480
cauaucgcuc aggucgcggc gaccuugugg uuaacuagga ccuugcauga caaggccuug        540
gcucgccacc aggguuuucg cgauuugcag                                         570

<210> SEQ ID NO 7
<211> LENGTH: 190
<212> TYPE: PRT
<213> ORGANISM: Citrus Yellow Vein associated Virus (CYVaV)
<220> FEATURE:
<221> NAME/KEY: MISC_FEATURE
<222> LOCATION: (1)..(190)
<223> OTHER INFORMATION: Citrus Yellow Vein associated Virus (CYVaV)
      Protein p21

<400> SEQUENCE: 7

-continued

```
Met Asp Pro Ser Ser Leu Pro Arg Ala Cys Trp His His Ala Arg Gln
1               5                  10                  15

Val Phe Arg Ala Ser Thr Ser Phe Ser Arg Glu Val Val Arg Ala Ala
                20                  25                  30

Arg Arg Trp Val Thr Met Pro Thr Ser Arg His Ala Tyr Asp Phe Ser
            35                  40                  45

Thr Ser Leu Gly Ile Val Ile Ala Glu Pro Ala Ala Arg Leu Arg Arg
        50                  55                  60

Arg Leu Pro Ser Val Arg Lys Cys Ala Glu Lys Leu Val Val His Lys
65                  70                  75                  80

Gln Val Asp Thr Leu Val Asp Glu Trp Cys Ser Gly Ile Pro Asn Pro
                85                  90                  95

Asp Ile Val Glu Val Gly Trp Ala Leu Arg Leu Arg Asp Arg Phe Gly
            100                 105                 110

Leu Pro Pro Ala Ser Glu Pro Thr Arg Leu Ser Gly Glu Arg Trp Val
        115                 120                 125

Leu Lys Gln Leu Asn Gly Val Asp Pro Glu Ser Trp Asn Ala Asp Leu
    130                 135                 140

Gly Arg Ser Val His Ile Gln Gly Asp Tyr Ala Pro Gly Arg Asn Ala
145                 150                 155                 160

His Ile Ala Gln Val Ala Ala Thr Leu Trp Leu Thr Arg Thr Leu His
                165                 170                 175

Asp Lys Ala Leu Ala Arg His Gln Gly Phe Arg Asp Leu Gln
            180                 185                 190
```

<210> SEQ ID NO 8
<211> LENGTH: 1407
<212> TYPE: RNA
<213> ORGANISM: Citrus Yellow Vein associated Virus (CYVaV)
<220> FEATURE:
<221> NAME/KEY: misc_feature
<222> LOCATION: (1)..(1407)
<223> OTHER INFORMATION: Polynucleotide Sequence of CYVaV Encoding
      Protein p81 (bases 752 to 2158)

<400> SEQUENCE: 8

```
augaccacac guguguugca guacaagggc cgagauccga uccuuccuc uucugaagcc      60 cuucaccgac uuaaccuucg gauagcugag cuauauaggu cuagaccuuc uaccgucuau     120
ccauuaaguu augaagggu ucucaauugc uaugaaggcc gacagcguac ucguuacgcc      180
caagccgucg agcaguugau gcgguccacu cuugagccga aagaugcgcg aguugaaacg     240
uucauuaaga acgagaaauu ugacugggcg uugaaagggg aggaggcuga uccucgagca     300
auccaaccaa ggaagccgaa auauuuggcu gagguuggac ggugguucaa accuuuggag     360
cgaaucaucu acaaggaucu caguaaaagg uuguauggug agggugcuga gccguguauc     420
gccaaaggcc uaaaugcauu agaaucugga gcgacuuuga ggcgcaaaug ggagaaguuu     480
ucuucuccag uuugcguuuc ucucgacgcu uccagguucg accugcaugu aagcguuggc     540
augcuaaagu ucacacacaa gcuauaugac uauuacugua agucucccac ucuccagcgc     600
uaucucaaau ggacacuccg caaccauggc gucgccuccu gcaaagaauu gucauaugag     660
uaugagguug uuggccggag aaugaguggu gacauggaca cugcauuggg caacugcguc     720
auuaugucga uacuuacaug guuuaugcuu agugaacuug gcauuaagca ugaauuauuc     780 gauaauuggug acgauuguuu guucauuugc gagucucacg acguccccag ccccgaggua     840
auuacaaacu gguuuucgga cuuugggguu gugguuaggu uggaaggcgu cacguccgug     900
```

-continued

```
uuugagcgua uugaguuuug ccaaacuucc ccaguaugga cugagagggg uuggcugaug      960
uguaggaaua uuaagucauu gaguaaagac cuuacgaaug uuaauucgug cacgggcucc     1020
acgauugaau auacccacug guugaaagca gugggaaagu gcgggucaau acucaaugcu     1080
gguguaccua uauuucaguc cuuucacaac augcuggaaa ggcuuggcac uaacucucgu     1140
auugaucgag ggguuuucuu caaaucaggg cuaguuaauc ucauucgugg gauggacagg     1200
cagccugacg uugacaucac uacuuccgcu cggcuuucuu ucgaaguggc auucgggaua     1260
acacccggga ugcaauuggc uauugaacgg uacuaugacu cugucauggg cucgcugagu     1320
aaaauagaaa caacuaagug gccaauugaa cuaagaaagg aauacgaaca cggaagugag     1380
ugguacgagg acuuaggcgu ccuagga                                         1407
```

<210> SEQ ID NO 9
<211> LENGTH: 469
<212> TYPE: PRT
<213> ORGANISM: Citrus Yellow Vein associated Virus (CYVaV)

<400> SEQUENCE: 9

```
Met Thr Thr Arg Val Leu Gln Tyr Lys Gly Arg Asp Pro Ile Leu Pro
1               5                   10                  15

Ser Ser Glu Ala Leu His Arg Leu Asn Leu Arg Ile Ala Glu Leu Tyr
            20                  25                  30

Arg Ser Arg Pro Ser Thr Val Tyr Pro Leu Ser Tyr Glu Gly Phe Leu
        35                  40                  45

Asn Cys Tyr Glu Gly Arg Gln Arg Thr Arg Tyr Ala Gln Ala Val Glu
    50                  55                  60

Gln Leu Met Arg Ser Thr Leu Glu Pro Lys Asp Ala Arg Val Glu Thr
65                  70                  75                  80

Phe Ile Lys Asn Glu Lys Phe Asp Trp Ala Leu Lys Gly Glu Glu Ala
                85                  90                  95

Asp Pro Arg Ala Ile Gln Pro Arg Lys Pro Lys Tyr Leu Ala Glu Val
            100                 105                 110

Gly Arg Trp Phe Lys Pro Leu Glu Arg Ile Ile Tyr Lys Asp Leu Ser
        115                 120                 125

Lys Arg Leu Tyr Gly Glu Gly Ala Glu Pro Cys Ile Ala Lys Gly Leu
    130                 135                 140

Asn Ala Leu Glu Ser Gly Ala Thr Leu Arg Arg Lys Trp Glu Lys Phe
145                 150                 155                 160

Ser Ser Pro Val Cys Val Ser Leu Asp Ala Ser Arg Phe Asp Leu His
                165                 170                 175

Val Ser Val Gly Met Leu Lys Phe Thr His Lys Leu Tyr Asp Tyr Tyr
            180                 185                 190

Cys Lys Ser Pro Thr Leu Gln Arg Tyr Leu Lys Trp Thr Leu Arg Asn
        195                 200                 205

His Gly Val Ala Ser Cys Lys Glu Leu Ser Tyr Glu Tyr Glu Val Val
    210                 215                 220

Gly Arg Arg Met Ser Gly Asp Met Asp Thr Ala Leu Gly Asn Cys Val
225                 230                 235                 240

Ile Met Ser Ile Leu Thr Trp Phe Met Leu Ser Glu Leu Gly Ile Lys
                245                 250                 255

His Glu Leu Phe Asp Asn Gly Asp Asp Cys Leu Phe Ile Cys Glu Ser
            260                 265                 270

His Asp Val Pro Ser Pro Glu Val Ile Thr Asn Trp Phe Ser Asp Phe
```

```
                275              280              285

Gly Phe Val Val Arg Leu Glu Gly Val Thr Ser Val Phe Glu Arg Ile
    290              295              300

Glu Phe Cys Gln Thr Ser Pro Val Trp Thr Glu Arg Gly Trp Leu Met
305              310              315              320

Cys Arg Asn Ile Lys Ser Leu Ser Lys Asp Leu Thr Asn Val Asn Ser
                325              330              335

Cys Thr Gly Ser Thr Ile Glu Tyr Thr His Trp Leu Lys Ala Val Gly
            340              345              350

Lys Cys Gly Ser Ile Leu Asn Ala Gly Val Pro Ile Phe Gln Ser Phe
            355              360              365

His Asn Met Leu Glu Arg Leu Gly Thr Asn Ser Arg Ile Asp Arg Gly
        370              375              380

Val Phe Phe Lys Ser Gly Leu Val Asn Leu Ile Arg Gly Met Asp Arg
385              390              395              400

Gln Pro Asp Val Asp Ile Thr Thr Ser Ala Arg Leu Ser Phe Glu Val
                405              410              415

Ala Phe Gly Ile Thr Pro Gly Met Gln Leu Ala Ile Glu Arg Tyr Tyr
            420              425              430

Asp Ser Val Met Gly Ser Leu Ser Lys Ile Glu Thr Thr Lys Trp Pro
            435              440              445

Ile Glu Leu Arg Lys Glu Tyr Glu His Gly Ser Glu Trp Tyr Glu Asp
        450              455              460

Leu Gly Val Leu Gly
465

<210> SEQ ID NO 10

<400> SEQUENCE: 10

000

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000
```

<210> SEQ ID NO 16

<400> SEQUENCE: 16

000

<210> SEQ ID NO 17
<211> LENGTH: 166
<212> TYPE: RNA
<213> ORGANISM: Citrus Yellow Vein associated Virus (CYVaV)
<220> FEATURE:
<221> NAME/KEY: misc_feature
<222> LOCATION: (1)..(166)
<223> OTHER INFORMATION: Polynucleotide Sequence of Recoding Frameshift
      Sites of CYVaV

<400> SEQUENCE: 17
ucgcucaggu cgcggcgacc uugugguuaa cuaggaccuu gcaugacaag gccuuggcuc      60
gccaccaggg uuuucgcgau uugcagugau uggggucgac gggcuagagg caaaagcagu     120
gccucuagcu ucuggacucc gacugcuucc gguuccgcga cccgga                   166

<210> SEQ ID NO 18
<211> LENGTH: 25
<212> TYPE: RNA
<213> ORGANISM: Citrus Yellow Vein associated Virus (CYVaV)
<220> FEATURE:
<221> NAME/KEY: misc_feature
<222> LOCATION: (1)..(25)
<223> OTHER INFORMATION: Polynucleotide Sequence of Recoding Frameshift
      Sites of CYVaV

<400> SEQUENCE: 18
caaagucgac gacugucuca gaccu                                           25

<210> SEQ ID NO 19
<211> LENGTH: 34
<212> TYPE: RNA
<213> ORGANISM: Citrus Yellow Vein associated Virus (CYVaV)
<220> FEATURE:
<221> NAME/KEY: misc_feature
<222> LOCATION: (1)..(34)
<223> OTHER INFORMATION: Polynucleotide Sequence of Recoding Frameshift
      Sites of CYVaV

<400> SEQUENCE: 19
aggucuugga cagucugcgg gcuugggaac gacg                                 34

<210> SEQ ID NO 20
<211> LENGTH: 3132
<212> TYPE: RNA
<213> ORGANISM: Ficus carica
<220> FEATURE:
<221> NAME/KEY: misc_feature
<223> OTHER INFORMATION: Polynucleotide Sequence of Fig Tree iRNA ("iRNA
      relative 1" or "iRNA r1")

<400> SEQUENCE: 20
aaauauggau ucgauaucaa ugcccgucgc cugcugguca aaagccaggc aggucuugcg      60
uacaccagcu aacuuuucca aaggguagu gaaggcugcg uaccgguggg ucaacaugcc     120
cagagccaaa uaugucagag augucuccac gagucuuggc auaguugucg cugagccugu     180
ugcugccgug cgccguuaga ugccuucgau aagcagccuu gcggaggagu ugguaacacg     240
ccagagcguc gacacucugg uggacgauug gugucucgga cuuuccaacc cugacaacaa     300

```
cguggagguu gguugggcac uucgucugag ggaccgcuuu ggucuuccuc ccgccucuga    360
gcccacaagg cucaguggug agagaugggu gcuuaaacaa cucaaugggg uagacccgga    420
gucguggaau guugaucugc aaagcguuuu cgaagacgcu caggaugacu uccaucggga    480
cuacgcccca aggaggaaug cccaaaucgc ucaaauugcg gcaacccuau ggcuuacaaa    540
gaccuuaguc gauaaggcuu uagcacgcca ucaggauuuu cgcaguuugc agugauuggg    600
gucgacgggc uagaggcuaa agcagugccu cuggcugcug gacuccgacu gcuuccgguu    660
ccgcggcccg gacaaagccg acggcugucu caaaccuugc uacucccuac uccccgugcu    720
caauuuguca aucacgcuaa cucagguaau aauuugggc guguuuugac cacacgggug     780
augcaauaca aaggccgaga cccgauacua cccucccagg aagcccugcg caaacuuaac    840
cuucggauag gacaguugua uaagucuaga ccauccacug ucuaucccu gaguuaugau     900 ggguuucuua auuguuauga uggccgacag cguacucgcu acgcucaugc cgucgagcaa    960
uugaugggug ccgcucugac cccaaaagau gcgcgaguug agacguucau uaagaacgag   1020
aaguuugauu gguuguugaa gggagacgag gcugauccuc gugcaaucca accuaggaag   1080
ccgaaauauu uggccgaggu uggucgaugg uucaaaccgu uggagcgaau caucuacaag   1140
gaucucaguu ugcguuugua cggugauaac gcugaaccuu gcauugccaa aggcuuaaau   1200
gcauuggaau caggggcuac guugagacgu aaaugggaaa aguucgcuaa uccuguuugu   1260
guuucauugg augcuucucg uuucgaccug cacguaagug uuggcuuguu aaaguucacg   1320
cauaaauugu acaacuauua cugcaagucu cccacucuuc aacgauaucu caaauggaca   1380
cuccgcaacu ccgguaucgc cuccguaag gaaaaaucau augcguauga gguugaaggc    1440
cguagaauga guggcgacau ggacaccgca uuaggcaacu guaucaucau gagauuauua   1500
acuugguuua ugcuuagcga acuuggcgug cggcaugagc uuuucgauaa ugguaugac    1560 uguuuguuua uuugugaaaa agaagacguu ccuagugcug agguaaucac gaacugguu    1620 acggauuuug gguuuguggu uaagcuagaa ggcgucacgu ccuguuuga gcgcauugag   1680 uucugucaga ccucaccagu auggacgcg aggggauggc ugauguguag aaacaucaag    1740
ucauugagua aagauuuaac gaauguuaau ucgugcacug guucugccgu ugaauacacu   1800
cauugguuga aggcgguggg caagugugga ucuauacuca augcuggugu gcccauauuu   1860
caguccuuuc acaacauguu ggucagguug ggcacgaauu cgcguauaga ucgcggggua   1920
uucuuuaggu guggacuugu uaaucucauu cugggaugga cagacaaccu gaaaguugag   1980
aucacuacuu ccgcucgucu uucuuuugaa guggcauucg ggaucacucc cggcaugcaa   2040
uuggcuauug agcaauuuua ugacucaguc guggcccuc uggguaaaau aaaaucugua    2100
aaauggccaa uagaucuaag aaaggaauac gauuacggaa gcgcgugguu cgaagaccaa   2160
ggcguccuag ggugaacaag gaacucggau uaccgaugac accguucaa acuagaaugg    2220 uucggucaac guugaccaag gagaccaaca uaccuucuac ugcaaauagc ggucgggagg   2280
cuguuugggc uuguuggcca aucaacuuua ugucuuuuc gcaacuagcc ucacucguga   2340
auaaaccguu auacuggcgu guguccagug ugcaaguugc aauggagccg gcgaugucua   2400 cuuccacccca acauugugga guuggucuca guucuucugg ggccuucacu aacggugaug   2460
gguucgguaa cgucuuuaag cucuugcguu cuuguaacua uacgcggcgc ucucccgugg   2520
gaggaaacgu gauggucaaa uggcccaucu gcaugcccuu cauucuuaac gaugaugcgc   2580
acaagaacac aggauuaacc gccgugugua ucauugcagu caccaauacu gguguugcuaa   2640 cugguucaauc uuggacggag auucuuuuga auguggagua uguaguggu gcauagacag     2700
```

```
ucugcgggcu ugggaacgac gccccgcuag caacguacug cucuccuacc ggacugguag    2760
ccguuuaguu aucuuggagc gauagcacug ugagccucac ucaacgcgcg auggacgugg    2820
cgagugcccc ucagagauuu gugaaacucu auagagcuau uucgcgagcc agaagggagg    2880
auggccaccu gguguaagcc agguauccc gggggggcuu uacucggggu cgcauuacug    2940
cuuagaccac aagguagggu ucgcaucuug gaacugaccc uaugaccuug ugggugcccu    3000
aaccggacug guagccguuu aauaucuugg agcgauuagc acgugugagc ccucacucaa    3060
cggcgcgauu ggacguggcg agugcccuc agaguaaucu gcagagcucc ggcagucgug    3120
ggaggcaagg ca                                                        3132

<210> SEQ ID NO 21
<211> LENGTH: 3275
<212> TYPE: RNA
<213> ORGANISM: Ficus carica
<220> FEATURE:
<221> NAME/KEY: misc_feature
<222> LOCATION: (1)..(3275)
<223> OTHER INFORMATION: Polynucleotide Sequence of Fig Tree iRNA ("iRNA
      relative 2" or "iRNA r2")

<400> SEQUENCE: 21
cucccacgac ugccggagcu cugcagaauu ccaccggggg uaccuggcuu acaccaggug     60
gccauccucc cuucuggcuc gcggaauagc ucuauagagu uucacaaauc ucugaggggc    120
acucgccacg uccaucgcgc guugagugag gcucacagug cuaucgcucc cagaauucgg    180
gauaaauaug gaagaaacuu cuuugcccaa agccugcugg aucaaaagcc aggcaggucu    240
ugcguacacc agcuaacuuu uccaaagggg uagugaaggc ugcguaccgg ugggucaaca    300
ugcccagagc caaauauguc agagaugucu ccacgagucu uggcauaguu gucgcugagc    360
cuguugcugc cgugcgccgu cagaugccuu cgauaagcag ccuugcggag gaguugguaa    420
cacgccagag cgucgacacu cugguggacg auuggugucu cggacuuucc aacccugaca    480
acaacgugga gguugguugg gcacuucguc ugagggaccg cuuuggucuc cucccgccu     540 cugagcccac aaggcucagu ggugagagau gggugcuuaa acaacucaau ggaguagacc    600
cggaaucuug gaaugacgac uaugcguucg aagacgcuca ggaggauuuu caacgggaau    660
acgucccggg aaggaaugcc cauauugcug caacugcggc aacucuaugg cugacaaaga    720
ccuuguauga caaggcuuua guucgccauc agggguuucg caguuugcag ugauugggu     780 cgacgggcug gaggcuaaag cagugccucc agcugcugga cuccgacugc uuccgguucc    840
gcggcccgga caaagccgac ggcugucuca gaccuuacua cuuccuacuc cccgugcuac    900
uuuugucaau caugcaaauu caggcaauaa ucuugagcgu guuuugacca cacgggugau    960
gcaauacaaa ggccgagacc cgauacuacc cucccaggaa gcccugcgca aacuuaaccu   1020
ucggauagga caguuguaua agucuagacc auccacuguc uaucccuga guuaugaugg    1080 guuucuuaau uguuaugaug gccgacagcg uacucgcuac gcucaugccg ucgagcaauu   1140
gaugggugcc gcucugaccc caaaagaugc gcgaguugag acguucauua agaacgagaa   1200
guuugauugg uuguugaagg gagacgaggc ugauccucgu gcaauccaac cuaggaagcc   1260
gaaauauuug gccgagguug gucgaugguu caaaccguug gagcgaauca ucuacaagga   1320
ucucaguuug cguuuguacg gugauaacgc ugaaccuugc auugccaaag gcuuaaaugc   1380
auuggaauca ggggcuacgu ugagacguaa augggaaaag uucgcuaauc cuguuugugu   1440
uucauuggau gcuucucguu ucgaccugca cguaaguguu ggcuuguuaa aguucacgca   1500
```

-continued

```
uaaauuguac gacuauuacu gcaagucucc cacucuucaa cgauaucuca aauggacacu      1560
ccgcaacucc gguaucgccu ccuguaagga aaaaucauau gcguaugagg uugaaggccg      1620
uagaaugagu ggcgacaugg acaccgcauu aggcaacugu aucaucauga cgauauuaac      1680
uugguuuaug cuuagcgaac uuggcgugcg gcaugagcuu uucgauaaug gugaugauug      1740
uuuguucauu ugcgaagaaa aagacguacc uagccccgag acgaucauga acugguuugc      1800
ggauuuuggg uuugugguua gguuagaagg cgucgugucc cguguugagc gcauugaguu      1860
cugccaaaca ucgccuauau ggacugaucg agguuggcug auguguagaa acaucaaguc      1920
uuugaguaag gaucuuacga acguuaauuc gugcacuggc uccacuguug aauacaccca      1980
uugguugaaa gcaguuggaa aguguggauc ggugcucaau gcgggugugc cuauauuuca      2040
gucauuucac aacauguuga ugcgauuggg uacgaauucg cguauagauc gcggggauuu      2100
cuuuaggugu ggacuuguua aucucauucg ugggauggac agacaaccug aaguugagau      2160
cacuacuucc gcucgucuuu cuuuugaagu ggcauucggg aucacucccg gcaugcaauu      2220
ggcuauugag caauuuuaug acucagucgu gggcccucug gguaaaauaa aaucuguaaa      2280
auggccaaua gaucuaagaa aggaauacga uuacggaagc gcgugg_uucg aagaccaagg      2340 cguccuaggg ugaacaagga acucggauua ccgaugacac cuguucaaac uagaaugguu      2400
cggucaacgu ugaccaagga gaccaacaua ccuucuacug caaauagcgg ucgggaggcu      2460
guuugggcuu guuggccaau caacuuuagu gucuuuccgc aacuagccuc acucgugaau      2520
aaaccguuau acuggcgugu guccagugug caaguugcaa uggagccugc aaugucuucu      2580
uccacccaac auugugguug uggcucagu ucuucugggg ccuucacaua acggugaugg      2640
guucgguaac gucuuuaagc ucuugcguuc uuguaacuau acgcggcgcu cucccgugggg      2700 aggaaacgug auggucaaau ggccuaucug caugcccuuc auucuuaacg augaugcgca      2760
caagaacaca ggauuaaccg ccugugugau cauugcaguc accaauacug gugugcuaac      2820
uggucaaucu uggacggaga uucuguugaa uguggaguau acgccccgcu agcaucguac      2880
ugcucuccua ccggacuggu agccguuuag uuaucuugga gugauagcac ugugggggcca      2940 cauuugacgc gcauuggacg cagacaaugu cccuccacag auuugugaau ucucuauggag      3000 cuguaaccuc ggucucucua uagcuugucc gaacaggaaa uggacauaaa auaauugcug      3060
uuccaacacg uuguguuggu aaagaaguua uagauguggu gcgccagaca aguggauggc      3120
aaccuggagu aauccaggcg cucugggggg cuuauacucg gagugcauua cugcuuuaga      3180
ccguuaaucu caagaaccau guguucgca uggggaggau uaacggcgcc caauucccuu      3240
guuaguuuag guacgccuug gucuucgaac cacgc                                3275
```

```
<210> SEQ ID NO 22
<211> LENGTH: 2985
<212> TYPE: RNA
<213> ORGANISM: Ficus carica
<220> FEATURE:
<221> NAME/KEY: misc_feature
<222> LOCATION: (1)..(2985)
<223> OTHER INFORMATION: Polynucleotide Sequence of Fig Tree iRNA ("iRNA
      relative 3" or "iRNA r3")

<400> SEQUENCE: 22
```

```
ggggguaaaua uggagaacca gcacacccau guuugcccac ggucguuccu gcgaaccugc       60
agggcgaucc ucgcggcucc agccaacuac ggucgugaug uggucaaaau cgccuacaaa      120
ugggcaucac gaaaccccgc caccgccccc cgaagugucc gagaauccau cggggucguu      180
```

-continued

| | | | | | |
|---|---|---|---|---|---|
| gucggaagcg | cuguggacuu | cuugagcgcu | ccucgcaagc | guuuagaaga | ccgcgcagag | 240 |
| caguugguge | aagacgaccg | ggucgaccgg | aucguccgcg | agugggagcu | aggaaccgcu | 300 |
| gacucccgaa | uuccggaagu | ugaguggca | uaccgucugc | gcgaccgcuu | cggcgucgug | 360 |
| uccgccagcg | agccugcuag | gcaaacuggu | gagaggaguggg | ugcucaagca | acuagaggga | 420 |
| uuggagggg | gggaguuccg | cugcauaccc | auugagccau | ucuuuggug a | ugcaccggcc | 480 |
| cccguccaua | gcccugggag | caacagcgug | auugcugcua | uugcggcgac | ccuuuggaug | 540 |
| acgccuaccc | gccugaccg | ggcguugaga | cgucaccagg | guuuucgcaa | cuagcgguga | 600 |
| ucggagucga | cggagugucu | gcuuuagcgg | ugcaggcauc | uucugaacuc | cgaccgcuac | 660 |
| ggguugggcg | accccgucaa | agucgacguc | guucgugguc | ucgacuaug | ccagcaccca | 720 |
| aguccuguuu | cgugaaccac | gcuaaacucug | accacaaucu | caaaacgguc | auggaaaaca | 780 |
| gggugcucaa | guacaaaggc | caagaacccg | caaagccccg | gguagaagcc | uauaagcagc | 840 |
| ucuaugaaag | gauacgaccg | cgauaucguu | cucuaccuga | cacggucuau | ccucuaucau | 900 |
| augauggcuu | cccucaagugc | uacuccggac | guaggcgaac | acgauacgaa | caggccgucc | 960 |
| aggaguuagu | aaacgcgcca | cucacacccg | aagaugcugu | cguuuccacg | uucaucaaga | 1020 |
| acgagaaauu | cgauuggcuc | caaaagaaag | aacuugcgga | ucccagagcu | auccaaccuc | 1080 |
| ggaaaccgaa | auaccuggcc | gaaguuggga | ggugguucaa | gccucuggag | cacauaaugu | 1140 |
| auaaagacuu | ggcaaaacgg | uuguacgguc | aggaugcguu | gccuugcaua | gcgaaagggc | 1200 |
| ugaacgcuag | agaaacggcu | gaagugcucc | gagccaaaug | ggacaaguuc | gcuucucccg | 1260 |
| uuugcgucuc | gcuggaugcc | agucgguucg | aucugcaugu | aagccugac | gcauugcggu | 1320 |
| uuacgcaccg | ccuguaccac | aaguauugcc | aaagucggca | acuccgcaag | uaccuagaau | 1380 |
| ggacgcugag | aaacgcuggc | gucgccucau | guccugaaag | cgcuuaucag | uaugagguug | 1440 |
| aggggagacg | caugaguggc | gacauggaca | ccgcacucgg | caacugcgua | cuuaugcucu | 1500 |
| gcuugacaug | gaacuuccuc | gaucaacaua | acaucaagca | ugagauaaug | gacaacggag | 1560 |
| augacugcuu | guucaucugu | gaagcugccg | augugccaac | cgacaagcaa | aucauggacu | 1620 |
| acuaccucga | cuuuggguuc | gugguucggu | uggaaggaaa | ggugucgug | uucgagcgaa | 1680 |
| uagaguucug | ucaaaccagu | ccgguguuga | cugcuaaugg | auggcguaug | guuagaaauu | 1740 |
| ugaaguccau | ugcgaaggac | cucugcaaug | ugaacauggc | gacuggguca | cucagugaau | 1800 |
| acacugcgug | gcuuaaagcc | gugggaaucu | gugguagaau | ccugaacgau | ggggguuccaa | 1860 |
| ucuucuccgc | cuuccacaac | augcuggugc | gacauggaac | gaacucacga | auagauagag | 1920 |
| cggguguucug | ggaaugugga | cugacaaacu | ugaucaaagg | caugaguuuc | gagcaacugg | 1980 |
| aaaucacugu | cgcugcgcgc | gaguccuuuu | aucuggcaua | cgguaucaca | ccggcgagac | 2040 |
| aacucgcgau | ugaagaguau | uacgacucac | uccagggccc | ggugggguaaa | auacaacuuc | 2100 |
| augaauggcc | acuacaacuc | aaagaggaau | acgcgugcgg | cgccgagugg | uucgaaggag | 2160 |
| acggcgagcg | ggcuugaggc | ccgcuggcuu | gcccuucgug | cccggcagcu | cucgcacggu | 2220 |
| ucggacugcg | cucguccucg | agaaccacuu | gccgaugucc | ucggcacagu | ugggucaaga | 2280 |
| ggccguugcg | uauucuaucc | cgugcaaugu | ucgaaacaug | ccuacgaucc | ugacucucgc | 2340 |
| caccacuccg | cucuauuggc | guaucaccgc | caucacuguc | gcgauggagc | cugcaaaguc | 2400 |
| cacaucgacc | caaauugccg | gugugggggaa | ugcugauuca | uuucagucug | ccaccuacaa | 2460 |
| cgguuuuggg | aacguguuua | agaaaaugcg | cgcuuugaau | uucgugagac | gcucggcgcc | 2520 |

```
cggaggcaau cuucagguac gcuggccuau caauauggac uggaucuccg cauccgacac    2580
ggacaaggau agcacaaaag ugcccucgcu auucuuugcc gugaccaacc caggugugau    2640
cgaaaccaaa caaggggaca gugaggccug guuggaaugg gaguuggagc uggaguacau    2700
aguuggaggc uaggaacgac ugcccgcuug agaucgacuc ucccgugggug agguaccacc    2760 cacucagcug ugucagccgg uuggagaaac ucggugcga uagcacuguu ggccccugcc    2820
uagcgugugc uguggaaag ccccaacaga uuugugaaac acuggaguug ucgacccgcg    2880
agacgugcgg cucgaguugu cgcuucccg ugaggggggc ugccggggggg uagagaaaua    2940 uucccggaua uuauccgcua agaccuacgc gcgacgaaac uggcg                    2985
```

<210> SEQ ID NO 23
<211> LENGTH: 4252
<212> TYPE: RNA
<213> ORGANISM: Pea Enation Mosaic Virus 2 (PEMV2)

<400> SEQUENCE: 23

```
ggguauuuau agagaucagu augaacugug ucgcuaggau caagcggugg uucacaccug    60
acuucacccc uggcgagggc gugaagucua gagcucaacu ggaaagagag cuggaucccca   120 ccugggcgcu ucucgugugc caagaacgag cgcgucguga ugcugacagu auugcuaaug    180
agugguacga gggcagcaug gagugcaacc uccuuauccc ucggcccaca accgaggaug    240
uauuuggccc cuccaucgcc ccugagccug uggcucuagu ggaggaaacu acccguuccc    300
gcgcgccgug cguggaugau ccugccgagg aguccuguaa gucagcggag auugauccug    360
uugaucucgc caaguucgac ucccuccauc gucgccuguu ggcugaagcc aacccuugca    420
gggaaauggu ucuguggugu ccuccuggcc uaccagcaga gcgcgacguc cugcccaggg    480 cacgugggggu gauaaugauc cccgaagucc cugcccucgc acauaccuug uccgugaagg    540
uuauggaggc ugugcgguug gcacaggaag ucuuggcauc ccuugccaag agggccuuag    600 agaaaaggguc uacaccaacc cuuaccgccc aggcccagcc agaggcuacc cugucggggu    660
gcgacuaccc guaucaggag acuggagcag cagccgcgug gauaacgccu ggcugcauug    720
ccauggagcu cagagccaaa uuuggcgucu gcaaacgcac ccccgcaaac uuagagaugg    780
ggagucgcgu cgcccgcgag cuccugcggg auaacugugu cacuugcagg gagaccacgu    840
gguacaccag ugccauugcu guggaccugu gguugacccc gaccgucgucu gaccuggccu    900 guggccggcg agcggcggau uuuuggguagg ggcugugcug ccucggcugg gggaagacac    960
caguggugcg uuugacaacc ugcaccccag caucgaggua aucaaggcgg cuaggccccg    1020
cccaacccag aggaugucgu uccaaaucga cguugugcgu ccucuuggag auuuugggugu    1080 gcacaacaac uccccuuguua accuagccag gggaauuaau gaaaggggugu ucuacacgga    1140 caaugcuagg acagaacccc uccagccuaa gguucccuuc cccucaucac gggagcuaaa    1200
aaccuucaga gucacccccuu ggaccaugga uaggguugug gagaguuaca cagggguccca   1260 gcgcacucgc uaugcuaacg cgcgggacag cauauuuaucc aacccucuga gucccaaaga    1320 ugcgcgggguc aagacguuug ucaaagcuga aaagauaaau uucacagcca aaccugaccc    1380
cgccccucgu gugauacagc cuagggaucc acgauucaac auuguccugg cuaaauacau    1440
caagccuuug gagccaaugu uguacaaagc acuggggaaa cuuuacaagu accccgcagu    1500
ugcuaagggg uuuaacgcgg uugagacggg ggagaucauc gccggcaagu ggcggugcuu    1560
caaagauccu gucgucgugg gauuagacgc uucccgauuu gaucagcaug uaucugucga    1620
ggcguugcag uucacccacg cgguguacag aggguucauc aagucacggg aguuuaacaa    1680
```

-continued

```
ccuccuacag augauguaca ccaaccgugg ccuagggucc gcuaaggacg gauucguccg   1740
uuacaagguu aaagguagac gcaugagcgg ugacauggac accuccuugg gcaacugugu   1800
gcucaugguu uugcucacca ggaaccuuug caagguucua ggcaucccgc acgagcucuu   1860
caacaauggu gaugauugca ucgucuuuuu cgaucguugc cacuuggaga aguucaacaa   1920
ugcugucaag acuuauuuug cggaccuagg guuuaagaug aaggugggaac cgccgguuga   1980 cguguuggag aaaauagagu ucugccaaac gcagccuauc uaugacgggg agaaguggcg   2040
caccgugcgu ugcaucucga guaucggaaa agauugcuca uccguuauua guugggacca   2100
auuggagggg uggugggaaug ccaucgccca gagguggucug gcugugugug gcggaaugcc   2160
gauauacacg ucguucuacc ggguggcuagc acgggccggu aagagugggga ccaagugucca   2220 gucacacccc uuguggaaaa acgaggggguu gaauugguac aggaugggga uggaccuuuc   2280
ucaugagguu aauguuacccc cucaggcgcg ccugucuuuc uucgcgggguu uuggguauuuc   2340 cccccgaug caggucgcca uugaggcgcu guaugacaag cugccuccac cguccccca   2400 ccaugguccu ccgguuaagg cuguaacaca gcgaguguuc accaauuauu ucacgccgga   2460
aagcgccugu guuagcauga gcacgaauga agacaacaaa ucugacuuug cuguuuacgg   2520
cccugugccu acagugaugu cucuuugugc ucaguguuag gcucuuaaau uuuagcgaug   2580
gcgugacacg guuacacccu gaauugacag gguacagauc aagggaagcc ggggagucac   2640
caacccaccc ugaaucgaca gggcaaaaag ggaagccggg caccgcccac guggaaucga   2700
ccacgucacc uuuucgcguc gacuaugccg ucaacacccu uucggcccgc cagccuagga   2760
caauggcggu agggaaauau augacgauaa ucauuaaugu caauaacgac gagcgcaagc   2820
aaccagaagg agcuacuggc agcucuguac ggcgaggugua caauaaaaga acucgaggaa   2880
acaaaccucg gagucaucac cccgguucgc gcgaacgaaa agguuacaau cacccccucuc   2940 cuacccccaa aaacucaaag cagggucagc uccguacuga agcgguucag gagcacccga   3000
aacacggggg gacugcuuuc cguagagaaa gugguggguag uguucaccccc ucacaucccc   3060 gacgacgugc uaggagaggu ggagauaugg cuccacgaca gcauccucccc ccaccucggg   3120 agcgucggac caagacugaa acucaagcug agcgaagggc ccaagcucuu agcguucuac   3180
ccacccuacu cgauugcauu gggggacucg aucucgggcc agccgagguc cuucuccauu   3240
gucaccgagc uguucgaagg caacuucgca ccgggggugca gcccauucag ccuguuccuc   3300
auguggaguc cacgcaucga agcagugacc cacaacuacu ugagucgucc accacgugcu   3360
cugccaauuu gcagaacgau ggugcgggac gcguuaucgg agguggcauc ccaacagcaa   3420
uaccugaagg gagcgaugu gaacagguau gccaugccuc ucacuacggg ugauggccag   3480
cauagagcca ugaaggggc ucccagugcc cuuccaccaa cgggggugug uacccaggcu   3540
ucuaagugag gcuucgcuuc ccgccggaag accgcggcgg uucuguuccu cccacaggag   3600
uacggcaaca acccaccuug ggaaaguggg gaccccagca cuaacuccuu uaacuaggcg   3660
ggcguguugg uuacaguagg aggggacagu gcgcaucgaa acugagcccc accacaacuc   3720
ucauccacgg ggugguuggg acgcaggugu cggagggauc gccagcccuc aggauaguga   3780
gcucccgcag agggauaagc uaucucccug cgacguagug guagaacacg ugggauaggg   3840
gaugaccuug ucgaccgguu aucggucccc ugcuccuucg agcuggcaag gcgcucacag   3900
guucuacacu gcuacuaaag uuggugguggg augucucgcc caaaaagauc acaaacgcgc   3960
gggacaaggu cccuuccacc uucgccgggu aaggcuagag ucagcgcugc augacuauaa   4020
```
cuugcggccg auccaguugc acgacuggug gucccccuca gugucucggu ugucugccga          4080
gugggcggug gucggauucc accacacccu gccacgaggu gcguggagac uuggccaguc          4140
uaggcucguc guaauuaguu gcagcgacgu uaaucaaccc guccgggcau auaauaggac          4200
cgguugugcu ucuuccuccc uucuuagcca ggugguuacc ucccuggcgc cc                 4252

<210> SEQ ID NO 24
<211> LENGTH: 313
<212> TYPE: RNA
<213> ORGANISM: Pea Enation Mosaic Virus 2 (PEMV2)
<220> FEATURE:
<221> NAME/KEY: misc_feature
<222> LOCATION: (1)..(313)
<223> OTHER INFORMATION: Intergenic Plus Region of PEMV2

<400> SEQUENCE: 24
guuagcauga gcacgaauga agacaacaaa ucugacuuug cuguuuacgg cccugugccu            60
acagugaugu cucuuugugc ucaguguuag gcucuuaaau uuuagcgaug gcgugacacg           120
guuacacccu gaauugacag gguacagauc aagggaagcc ggggagucac caacccaccc           180
ugaaucgaca gggcaaaaag ggaagccggg caccgcccac guggaaucga ccacgucacc           240
uuuucgcguc gacuaugccg ucaacacccu uucggcccgc cagccuagga caauggcggu           300
agggaaauau aug                                                              313

<210> SEQ ID NO 25
<211> LENGTH: 139
<212> TYPE: RNA
<213> ORGANISM: Pea Enation Mosaic Virus 2 (PEMV2)
<220> FEATURE:
<221> NAME/KEY: misc_feature
<222> LOCATION: (1)..(139)
<223> OTHER INFORMATION: Polynucleotide Sequence of Recoding Frameshift
      Sites of PEMV2

<400> SEQUENCE: 25
gaccgucguc gaccuggccu guggccggcg agcggcggau uuuugguagg ggcugugcug            60
ccucggcugg gggaagacac cagugugcgg uuugacaacc ugcaccccag caucgaggua           120
aucaaggcgg cuaggcccc                                                        139

<210> SEQ ID NO 26
<211> LENGTH: 65
<212> TYPE: DNA
<213> ORGANISM: Arabidopsis thaliana
<220> FEATURE:
<221> NAME/KEY: misc_feature
<222> LOCATION: (1)..(65)
<223> OTHER INFORMATION: Sequence of Insertion Region

<400> SEQUENCE: 26
taggcctcga cacgggaagg tagctgtccc ggcactgggt tgcacatatt ccgtgccgac            60
gccac                                                                        65

<210> SEQ ID NO 27
<211> LENGTH: 43
<212> TYPE: DNA
<213> ORGANISM: Arabidopsis thaliana
<220> FEATURE:
<221> NAME/KEY: misc_feature
<222> LOCATION: (1)..(43)
<223> OTHER INFORMATION: Insertion Sequence Region

<400> SEQUENCE: 27

```
ccggcctcga cacgggaagg tagctattcc gtgccgacgc cgt                    43

<210> SEQ ID NO 28

<400> SEQUENCE: 28

000

<210> SEQ ID NO 29

<400> SEQUENCE: 29

000

<210> SEQ ID NO 30
<211> LENGTH: 10
<212> TYPE: RNA
<213> ORGANISM: Citrus Yellow Vein associated Virus (CYVaV)
<220> FEATURE:
<221> NAME/KEY: misc_feature
<222> LOCATION: (1)..(10)
<223> OTHER INFORMATION: Lock and Dock Sequence

<400> SEQUENCE: 30
guccuaaguc                                                         10

<210> SEQ ID NO 31
<211> LENGTH: 14
<212> TYPE: RNA
<213> ORGANISM: Citrus Yellow Vein associated Virus (CYVaV)
<220> FEATURE:
<221> NAME/KEY: misc_feature
<222> LOCATION: (1)..(14)
<223> OTHER INFORMATION: Lock and Dock Sequence

<400> SEQUENCE: 31 cagggggaaac uuug                                                   14

<210> SEQ ID NO 32
<211> LENGTH: 31
<212> TYPE: RNA
<213> ORGANISM: Citrus Yellow Vein associated Virus (CYVaV)
<220> FEATURE:
<221> NAME/KEY: misc_feature
<222> LOCATION: (1)..(31)
<223> OTHER INFORMATION: Scaffold Comprising Docked Tetraloop

<400> SEQUENCE: 32
cauuagcuaa ggaugaaagu cuaugcuaau g                                 31

<210> SEQ ID NO 33
<211> LENGTH: 57
<212> TYPE: RNA
<213> ORGANISM: Citrus Yellow Vein associated Virus (CYVaV)
<220> FEATURE:
<221> NAME/KEY: misc_feature
<222> LOCATION: (1)..(57)
<223> OTHER INFORMATION: Lock and Dock Structure

<400> SEQUENCE: 33
gcaccuaagg cgucaggguc uagacccugc ucaggggaaa cuuugucgcu auggugc      57

<210> SEQ ID NO 34
<211> LENGTH: 47
<212> TYPE: RNA
<213> ORGANISM: Citrus Yellow Vein associated Virus (CYVaV)
<220> FEATURE:
<221> NAME/KEY: misc_feature
```

-continued

```
<222> LOCATION: (1)..(47)
<223> OTHER INFORMATION: Sequence of Insertion into CYVaV

<400> SEQUENCE: 34
ggcuaguuaa ucucauucgu gggauggaca ggcagccuga cguugac                    47

<210> SEQ ID NO 35
<211> LENGTH: 30
<212> TYPE: RNA
<213> ORGANISM: Citrus Yellow Vein associated Virus (CYVaV)
<220> FEATURE:
<221> NAME/KEY: misc_feature
<222> LOCATION: (1)..(30)
<223> OTHER INFORMATION: Sequence of CYVaV Insertion (Unmodified; U at
      Positions 3, 6, 8, 14, 17 and 29)

<400> SEQUENCE: 35
guuaauguag gugucuuucc guaucuaguc                                       30

<210> SEQ ID NO 36
<211> LENGTH: 30
<212> TYPE: RNA
<213> ORGANISM: Citrus Yellow Vein associated Virus (CYVaV)
<220> FEATURE:
<221> NAME/KEY: misc_feature
<222> LOCATION: (1)..(30)
<223> OTHER INFORMATION: Sequence of CYVaV Insertion (Modified; G at
      Positions 3, 6, 8, 14, 17 and 29)

<400> SEQUENCE: 36
gucaacgcag gugccugucc guaucuagcc                                       30
```

PLANT VECTORS, COMPOSITIONS AND USES RELATING THERETO

CROSS-REFERENCE TO RELATED APPLICATIONS

This application is a § 371 National Stage Application of PCT/US2019/060945 (filed Nov. 12, 2019), which application is based on U.S. Provisional Patent Application Ser. No. 62/760,098, entitled "Vectors Useful for Treating Plant Diseases and Method of Using the Same," filed Nov. 13, 2018, which application is incorporated herein by reference in its entirety and to which priority is claimed.

STATEMENT REGARDING FEDERALLY SPONSORED RESEARCH OR DEVELOPMENT

This invention was made with government support under Grant No. AP17PPQS and T00C118 awarded by the United States Department of Agriculture (USDA), and under Grant No. 1411836 awarded by the National Science Foundation (NSF). The United States government has certain rights in this invention.

REFERENCE TO SEQUENCE LISTING

This application includes one or more Sequence Listings pursuant to 37 C.F.R. 1.821 et seq., which are disclosed in computer-readable media (file name: 2105_0071PCT_ST25, created on Nov. 12, 2019, and having a size of 37,755 bytes), which file is herein incorporated by reference in its entirety.

FIELD OF THE INVENTION

The present disclosure relates to a single stranded RNA vector suitable for introducing a therapeutic agent, such as a peptide, a protein or a small RNA, into a host plant, wherein movement thereof is substantially limited to the phloem and targeted to control or manage a plant disease or condition.

BACKGROUND OF THE INVENTION

Both general and highly targeted anti-microbial agents have been developed for animals (e.g., humans) whose circulatory systems provide a delivery system for widespread application throughout the animal. In contrast, much less research has been conducted to develop general or targeted therapeutic agents for non-genetically modified plants since lack of a simplified circulatory system complicates delivery throughout the host plant. This is especially problematic in large, long-lived trees (e.g., citrus), where injection of anti-microbial agents may be rapidly diluted. As a result, few solutions exist for treating systemic plant infections or conditions beyond external application of pesticides, e.g., to control the target insert or other vector during the growing season, foliar applications to strengthen a plant's health in general, or expensive, short-duration injection of agents targeting the pathogen or vector.

Particularly concerning are diseases and conditions affecting the citrus industry. Huanglongbing (HLB), also known as Citrus Greening, is one of the most serious citrus diseases globally. HLB is associated with three species of the bacterium Candidatus Liberibacter spp. (*asiaticus, africanus,* and *americanus*) and is transmitted by two psyllid species, Asian citrus psyllid (ACP) (*Diaphorina citri, Kuwayama*)

and African citrus psyllid (*Trioza erytreae*, Del Guercio). HLB is graft-transmissible and spreads naturally when a bacteria-containing psyllid feeds on a citrus tree and deposits the pathogenic bacteria into the phloem where the bacteria reproduce. Once a tree is infected, there is no cure. While the diseased fruit pose no health threat to humans, HLB has devastated millions of acres of citrus crops throughout the world. In the United States alone, ACP and CL *asiaticus* (CLas) have decimated the Florida citrus industry, causing billions of dollars of crop losses within a very short time span. Moreover, HLB has spread into every citrus producing region in the United States. Most infected trees die within a few years from infection, and fruit develops misshapen and off flavored and thus is unsuitable for consumption. According to the United States Department of Agriculture (USDA), the entire citrus industry is at substantial risk.

Consideration of plant physiology aids in the development and implementation of strategies for managing plant diseases and conditions. The vascular system of plants is the key conduit for sugars and amino acids, as well as signaling molecules such as small ribonucleic acids (RNAs), proteins, peptides and hormones, which are required for a large number of developmental processes and responses to biotic and abiotic stress (FIG. 1) (Lee, J. Y. and Frank, M. (2018), *Plasmodesmata in phloem: different gateways for different cargoes*, Curr Opin Plant Biol 43:119-124; Tugeon, R. and Wolf, S. (2009), *Phloem Transport: Cellular Pathways and Molecular Trafficking*, Ann Rev Plant Biol 60:207-221). Messenger RNAs (mRNAs) comprise a portion of these signaling molecules, and thousands of companion cell mRNAs can be isolated from neighboring enucleated sieve elements, where they are transported bidirectionally by osmotically generated hydrostatic pressure from source (sugar generating) tissue to sink (sugar utilizing) tissue such as roots and shoot tips (Folimonova, S. Y. and Tilsner, J. (2018), *Hitchhikers, highway tools and roadworks: the interactions of plant viruses with the phloem*, Curr Opin Plant Biol 43:82-88; Ham, B. K. and Lucas, W. J. (2017), *Phloem Mobile RNAs as Systemic Signaling Agents*, Annual Rev Plant Biol 68:173-195). As much as 50% of the companion cell transcriptome is believed to be engaged in movement (Kim, G. et al. (2014), *Genomic-scale exchange of mRNA between a parasitic plant and its hosts*, Science 345:808-811; Thieme, C. J. et al. (2015), *Endogenous Arabidopsis messenger RNAs transported to distant tissues*, Nature Plants 1(4):15025; Yang, Y. et al. (2015), *Messenger RNA exchange between scions and rootstocks in grafted grapevines*, BMC Plant Biol 15, 251), which raises various questions with regard to how and why such a substantial subset of mRNAs are moving long-distances. For example, how selective is the process of RNA movement? If there is selection, how is it facilitated? Are transiting RNAs modified (e.g., methylated)? Are transiting RNAs found in any particular subcellular location before exiting into the SE? Are there "zip codes" for transiting RNAs? Are transiting RNAs bound by specific proteins and are there specific interacting sequences? How much of the flow of mRNAs is biologically meaningful and how much is non-selective, since sink cells are presumably capable of transcribing the same mRNAs?

Confusion in the mRNA movement literature is pervasive. Some studies have indicated that the major determinant of RNA mobility is their abundance in companion cells (Kim, G. et al. (2014), *Genomic-scale exchange of mRNA between a parasitic plant and its hosts*, Science 345:808-811; Thieme, C. J. et al. (2015), *Endogenous Arabidopsis mes-*

3 4 senger RNAs transported to distant tissues, Nature Plants 1(4):15025; Yang, Y. et al. (2015), Messenger RNA exchange between scions and rootstocks in grafted grapevines, BMC Plant Biol 15, 251). Mathematical modeling has been used to propose a non-selective, Brownian diffusion model for mRNA movement based mainly on their abundance, with half-life and transcript length also playing roles (Calderwood, A. et al. (2016), Transcript Abundance Explains mRNA Mobility Data in Arabidopsis thaliana, Plant Cell 28:610-615). However, other studies reached opposing conclusions, finding that mRNA abundance in companion cells does not correlate with movement (Xia, C. et al. (2018), Elucidation of the Mechanisms of Long-Distance mRNA Movement in a Nicotiana benthamiana/Tomato Heterograft System, Plant Physiol 177:745-758). In addition, while it is generally assumed that the phloem does not contain RNases that target the transiting RNAs (Morris, R. J. (2018), On the selectivity, specificity and signaling potential of the long-distance movement of messenger RNA, Curr Opin Plant Biol 43:1-7), Xia et al. also found that most mobile mRNAs are degraded and never reach the root or upper stem. Other studies found that the presence of a predicted tRNA-like structure is associated with over 11% of mobile mRNAs (Zhang, W. N. et al. (2016), tRNA Related Sequences Trigger Systemic mRNA Transport in Plants, Plant Cell 28:1237-1249), suggesting that mobile mRNAs might harbor specific "zip-codes". However, other abundant mRNAs containing similar tRNA-like motifs were not mobile (Xia, C. et al. (2018), Elucidation of the Mechanisms of Long-Distance mRNA Movement in a Nicotiana benthamiana/Tomato Heterograft System, Plant Physiol 177:745-758). Thus, prior studies have failed to identify and develop a model system consisting of a highly abundant, mobile RNA whose movement is traceable in living tissue under different cellular conditions.

Plant viruses, many of which move through the plant as a ribonucleoprotein complex (vRNP), have evolved to use the same pathway as used by endogenous RNA movement. Plant viruses can accumulate in substantial amounts, and most initiate infection in epidermal or mesophyll cells and then move cell-to-cell through highly selective intercellular connectors called plasmodesmata, which allow for continuity between the cytoplasm of neighboring cells (FIG. 1; see also Lee, J. Y. and Frank, M. (2018), Plasmodesmata in phloem: different gateways for different cargoes, Curr Opin Plant Biol 43:119-124; Schoelz, J. E. et al. (2011), Intracellular transport of plant viruses: finding the door out of the cell, Mol Plant 4:813-831). Long-distance systemic movement (leaf-to-leaf) requires that the virus enters companion cells, where replication takes place, followed by progeny exit into sieve elements by transiting through the specialized, branched plasmodesmata that connect companion cells and sieve elements. Once tubular sieve elements are reached, viruses move passively with the phloem photoassimilate stream and establish systemic infections upon exiting (Folimonova, S. Y. and Tilsner, J. (2018), Hitchhikers, highway tolls and roadworks: the interactions of plant viruses with the phloem, Curr Opin Plant Biol 43:82-88).

For viruses that transit through the phloem as vRNPs, movement is similar to that of host mRNAs. All plant viruses encode at least one movement protein necessary for movement, which bind to viral RNA and also dilate plasmodesmata. Thus, host mRNA movement also likely requires similar host-encoded movement proteins. Movement proteins are non-specific RNA binding proteins. However, questions remain with regard to how vRNPs load into the phloem and unload in distal tissues, although reprograming companion cell gene expression may be required (Collum, T. D. et al. (2016), Tobacco mosaic virus-directed reprogramming of auxin/indole acetic acid protein transcriptional responses enhances virus phloem loading, Proc Natl Acad Sci USA 113:E2740-E2749). If mRNA trafficking is so widespread and non-specific, it has remained unclear why RNA viruses require their own encoded movement proteins. Some researchers have suggested that RNA viruses require movement proteins if moving as preformed replication complexes that include a large RNA-dependent RNA polymerase (Heinlein, M. (2015), Plant virus replication and movement, Virology 479:657-671), which is beyond the size-exclusion limit (~70 kDa) of companion cell plasmodesmata. It has also remained unclear why and how some viruses are phloem-limited. For example, phloem-limited Closteroviruses have at least 5 movement proteins, and phloem-limitation can be relieved by over-expressing the silencing suppressor and downregulating host defenses (Folimonova, S. Y. and Tilsner, J. (2018), Hitchhikers, highway tolls and roadworks: the interactions of plant viruses with the phloem, Curr Opin Plant Biol 43:82-88), suggesting that phloem-limitation is a complex process for some viruses. Phloem-limitation can also be an active process (as opposed to lack of a cell-to-cell movement protein). For example, altering a domain of the Potato leaf role virus movement protein conferred the ability to exit the phloem (Bendix, C., and Lewis, J. D. (2018), The enemy within: phloem-limited pathogens, Mo Plant Path 19:238-254).

A direct connection between host movement of mRNAs and vRNP movement was established when the origin of plant virus movement proteins was solved. A pumpkin protein (RPB50) related to the Cucumber mosaic virus movement protein was discovered that was capable of transporting its own mRNA, as well as other mRNAs, into the phloem (Xoconostle-Cazares, B. et al. (1999), Plant paralog to viral movement protein that potentiates transport of mRNA into the phloem, Science (New York, N.Y.) 283:94-98; Ham, B. K. et al. (2009), A polypyrimidine tract binding protein, pumpkin RBP50, forms the basis of a phloem-mobile ribonucleoprotein complex, Plant Cell 21:197-215). A complex population of these endogenous movement proteins, known as non-cell-autonomous proteins (NCAPs), have been proposed as being responsible for the long-distance phloem trafficking of mRNAs (Gaupels, F. et al. (2008), Nitric oxide generation in Vicia faba phloem cells reveals them to be sensitive detectors as well as possible systemic transducers of stress signals, New Phytol 178:634-646; Gomez, G. et al. (2005), Identification of translocatable RNA-binding phloem proteins from melon, potential components of the long-distance RNA transport system, Plant J 41:107-116; Kim, M. et al. (2001), Developmental changes due to long-distance movement of a homeobox fusion transcript in tomato, Science (New York, N.Y.) 293:287-289; Pallas, V. and Gomez, G. (2013), Phloem RNA-binding proteins as potential components of the long-distance RNA transport system, Front Plant Sci 4:130; Yoo, B. C. et al. (2004), A systemic small RNA signaling system in plants, Plant Cell 16:1979-2000).

Since their discovery (Deom, C. M. et al. (1987), The 30-kilodalton gene product of tobacco mosaic virus potentiates virus movement, Science (New York, N.Y.) 237:389-394), a number of viral movement proteins have been identified that are responsible for intracellular trafficking of vRNPs to the plasmodesmata, as well as for cell-to-cell and long-distance movement (Tilsner, J. (2014), Techniques for RNA in vivo imaging in plants, J Microscopy 258(1):1-5). For some viruses (e.g., umbraviruses), cell-to-cell and long-distance movement are associated with multiple movement proteins (Ryabov, E. V. et al. (2001), *Umbravirus-encoded proteins both stabilize heterologous viral RNA and mediate its systemic movement in some plant species*, Virology 288:391-400). For example, closteroviruses such as Citrus tristeza virus contain three movement proteins. However, for most viruses, all movement activities are thought to be associated with a single movement protein.

Delivering engineered therapeutic agents into plants for combating diseases, insects or other adverse conditions (e.g., such as HLB and/or the carrier insects) using virus vectors is an established means of introducing traits such as resistance to pathogens or other desired properties into plants for research purposes. Various methods of providing vectors to plants are known in the art. This is often achieved by delivery of the virus vector into a plant cell's nucleus by Agrobacteria tumefactions-mediated "agroinfiltration," which may result in a modification of that cell's genome, or by delivering the virus vector directly into a cell's cytoplasm, which results in infection without a requirement for genomic modification. In the case of agroinfiltration, the cDNA of the viral genome is introduced into T-DNA, which is then provided to the plants. Such T-DNA comprises further regulatory DNA components, which allow transcription of the genome. A DNA insert is attached to a virus cDNA vector that is able to infect the targeted plant. If the virus is an RNA virus, the virus and insert are transcribed into RNA within the plant cells, after which the virus behaves as a normal RNA virus (amplification and movement). Thus, to act as an effective vector, a virus should be engineered to accept inserts without disabling its functionality and to ensure that the engineered virus is able to accumulate systemically in the host to a level sufficient to deliver and in some cases express the insert(s). These inserts, whether open reading frames (ORFs) that will be translated into proteins or RNAs that will be used for a beneficial function, should be delivered into the targeted tissue in a manner that is effective and sufficiently non-toxic to the host or to any downstream consumption of the host or the environment. However, only a limited number of viral vectors exist that meet the above criteria and are available for only certain plants (e.g., Tobacco rattle virus for tobacco). Unfortunately, there is either no known suitable viral vector, or only suboptimal viral vectors, for most plants, particularly for long lived trees and vines.

Thus, the ability to implement RNA or DNA therapies on a broad basis is substantially limited with existing technologies. Over 1,000 plant viruses have been identified with many plants subject to infection by multiple viruses. For example, citrus trees are subject to Citrus leaf blotch virus, Citrus leaf rugose virus, Citrus leprosis virus C, Citrus psorosis virus, Citrus sudden death-associated virus, Citrus tristeza virus (CTV), Citrus variegation virus, Citrus vein enation virus and Citrus yellow mosaic virus, among others. However, CTV, the causal agent of catastrophic citrus diseases such as quick decline and stem pitting, is currently the only virus that has been developed as a vector for delivering agents into citrus phloem.

CTV is a member of the genus Closterovirus. It has a flexuous rod-shaped virion composed of two capsid proteins with dimensions of 2000 nm long and 12 nm in diameter. With a genome of over 19 kb, CTV (and other Closteroviruses) are the largest known RNA viruses that infect plants. It is a virulent pathogen that is responsible for killing or rendering useless millions of citrus trees worldwide, although the engineered vector form is derived from a less virulent strain, at least for Florida citrus trees (still highly virulent in California trees). Prior studies have purportedly demonstrated CTV-based vectors to express engineered inserts in plant cells (U.S. Pat. No. 8,389,804; US 20100017911 A1). However, it has not been commercialized due to its inconsistent ability to accumulate in plants and achieve its targeted beneficial outcome. It is thought that CTV's inability to replicate to sufficiently high levels and heat sensitivity limits its ability to generate a sufficient quantity of RNA for treatment.

Thus, CTV-based vectors have a very limited ability to deliver an effective beneficial payload where needed. Moreover, CTV is difficult to work with due to its large size. CTV is also subject to superinfection exclusion, wherein a CTV-based vector is unable to infect a tree already infected with CTV. CTV is also highly transmissible from plant to plant via several aphid species, a property disliked by regulators concerned with uncontrolled escape into the environment where it might mutate or interact with other hosts in undesirable ways. In addition, strains suitable for one region (e.g., Florida) are unsuitable for varieties of trees in another region (e.g., California). Despite such problems, CTV is the only viral vector platform available for citrus trees.

Accordingly, there is a need for an infectious agent that solves some or all of the above-noted problems, and which is capable of introducing a desirable property and/or delivering a therapeutic agent(s) into a plant, particularly a long-lived plant such as a tree or vine.

SUMMARY

The present disclosure relates to a novel infectious agent(s) capable of delivering an exogenous insert(s) into a plant, compositions comprising a plant infected by the disclosed agent(s), and methods and uses relating thereto. The disclosed agents are sometimes referred to herein as "independently mobile RNAs" or "iRNAs." Despite being infectious single-stranded RNAs, iRNAs are not viruses given they do not code for any movement protein(s) or RNA silencing suppressors, which are key characteristics of all known plant viruses. In addition, unlike virtually all plant RNA viruses, with the exception of umbraviruses, iRNAs also do not encode a coat protein for encapsidating the RNA into virions, which is a requirement for vectored movement of viruses from plant to plant. Despite the lack of movement protein expression, iRNAs are able to move systemically within the phloem in a host plant. As compared to viruses, iRNAs have additional advantageous properties, such as: the ability to accumulate to levels exceeding those of most known plant viruses; relatively small size, e.g., being only about two-thirds the size of the smallest plant RNA virus and thus much easier to work with compared to such conventional plant RNA viruses; and the inability to spread on their own to other plants (given their inability to encode for any coat protein).

In accordance with disclosed embodiments, an infectious agent comprises an iRNA-based vector containing an engineered insert, which triggers in a plant expression of a targeted peptide, protein(s) and/or produces targeted small RNAs that are cleaved from the vector for beneficial application. Aspects of the present disclosure include: an iRNA-based vector for delivery of targeted anti-pathogenic agents; an anti-bacterial enzybiotic targeted at bacteria infecting a plant or bacteria required by the insect vector; an enzybiotic that is generated from the TEV IRES; incorporation of siRNAs into the iRNA genome; incorporation of inserts into a lock and dock structure to stabilize the base of a scaffold that supports the inserts; incorporation of siRNAs from a iRNA genome that has been modified to enhance the stability of the local region to precisely counter the destabilizing effects of the inserts; incorporation of an siRNA that disrupts or kills a targeted insect vector; incorporation of an siRNA that mitigates the negative impacts of a tree's callose production; incorporation of an siRNA that mitigates the plant's recognition of the pathogen; and incorporation of an insert that triggers a particular plant trait (e.g., dwarfism). Thus, the infectious agents and compositions disclosed herein possess superior and advantageous properties as compared to conventional technologies.

The iRNA-based vectors of the present disclosure are suitable for use as a general platform for expression of various proteins and/or delivery of small RNAs into the phloem of citrus and other host plants. In some implementations, a CYVaV-based vector is provided, which accumulates to massive levels in companion cell and phloem parenchyma cell. The vectors of the present disclosure may be utilized to examine the effects of silencing specific gene expression in the phloem of trees. In addition, CYVaV may be developed into a model system for examining long-distance movement of mRNAs through sieve elements. Since CYVaV is capable of infecting virtually all varieties of citrus, with few if any symptoms generated in the infected plants, movement of RNAs within woody plants may be readily examined.

In accordance with disclosed embodiments, the present disclosure is directed to a plus-sense single stranded ribonucleic acid (RNA) vector comprising a replication element(s) and a heterologous segment(s), wherein the RNA vector lacks a functional coat protein(s) open reading frame (ORF) and a functional movement protein(s) ORF. In some implementations, the RNA vector comprises a 3' Cap Independent Translation Enhancer (3' CITE) comprising the nucleic acid sequence(s) of SEQ ID NO: 4 and/or SEQ ID NO: 5. In some embodiments, the 3' CITE comprises the nucleic acid sequence of SEQ ID NO: 3.

In some embodiments, the replication element(s) of the RNA vector comprises one or more conserved polynucleotide sequence(s) having the nucleic acid sequence of: SEQ ID NO: 10, SEQ ID NO: 11, SEQ ID NO: 12, SEQ ID NO: 13, and/or SEQ ID NO: 14. In some implementations, the replication element(s) additionally or alternatively comprises one of more conserved polynucleotide sequence(s) having the nucleic acid sequence of: SEQ ID NO: 15 and/or SEQ ID NO: 16.

In some embodiments, the RNA vector is derived from citrus yellow vein virus (SEQ ID NO:1) or an iRNA relative thereof. The RNA vectors of the present disclosure are capable of systemic and phloem-limited movement and replication within a host plant. The RNA vectors of the present disclosure are functionally stable for replication, movement and/or translation within the host plant for at least one month after infection thereof.

In some embodiments, the heterologous segment(s) of the RNA vector of the present disclosure comprises a polynucleotide that encodes at least one polypeptide selected from the group consisting of a reporter molecule, a peptide, and a protein. In some implementations, the polypeptide is an insecticide, an antibacterial, an antiviral, or an antifungal. In some implementations, the antibacterial is an enzybiotic. In some implementations, the antibacterial targets a bacterium Candidatus Liberibacter species, e.g. Candidatus Liberibacter *asiaticus* (CLas).

In some embodiments, the heterologous segment(s) of the RNA vector of the present disclosure comprises a small non-coding RNA molecule and/or an RNA interfering molecule. In some implementations, the small non-coding RNA molecule and/or the RNA interfering molecule targets an insect vector, a virus, or a fungus. In some implementations, the small non-coding RNA molecule and/or the RNA interfering molecule targets a nucleic acid of the insect vector, the virus, or said fungus. In some implementations, targeted virus is selected from the group consisting of Citrus vein enation virus (CVEV) and Citrus tristeza virus (CTV).

It should be understood that the RNA vector may include multiple heterologous segments, each providing for the same or different functionality. In some embodiments, the heterologous segment(s) is a first heterologous segment, wherein the RNA vector further comprising a second heterologous segment(s), wherein the replication element(s) is intermediate the first and second heterologous segments.

In some embodiments, the heterologous segment(s) of the RNA vector of the present disclosure comprises a polynucleotide that encodes for a protein or peptide that alters a phenotypic trait. In some implementations, the phenotypic trait is selected from the group consisting of pesticide tolerance, herbicide tolerance, insect resistance, reduced callose production, increased growth rate, and dwarfism.

The present disclosure is also directed to a host plant comprising the RNA vector of the present disclosure. The host plant may be a whole plant, a plant organ, a plant tissue, or a plant cell. In some implementations, the host plant is in a genus selected from the group consisting of *citrus, vitis, ficus* and *olea*. In some implementations, the host plant is a citrus tree or a citrus tree graft.

The present disclosure also relates to a composition comprising a plant, a plant organ, a plant tissue, or a plant cell infected with the RNA vector of the present disclosure. In some implementations, the plant is in a genus selected from the group consisting of *citrus, vitis, ficus* and *olea*. In some implementations, the plant is a citrus tree or a citrus tree graft.

The present disclosure also relates to a method for introducing a heterologous segment(s) into a host plant comprising introducing into the host plant the RNA vector of the present disclosure. In some embodiments, the step of introducing the heterologous segment(s) into the host plant comprises grafting a plant organ or plant tissue of a plant that comprises the RNA vector of the present disclosure to a plant organ or plant tissue of another plant that does not comprise the RNA vector prior to said introduction. The RNA vectors of the present disclosure are capable of systemically infecting the host plant.

The present disclosure is also directed to a process of producing in a plant, a plant organ, a plant tissue, or a plant cell a heterologous segment(s), comprising introducing into said plant, said plant tissue or said plant cell the RNA vector of the present disclosure. In some embodiments, the plant is in a genus selected from the group consisting of *citrus, vitis, ficus* and *olea*.

The present disclosure also relates to a kit comprising the RNA vector of the present disclosure.

The present disclosure is also directed to use of the RNA vector(s) of the present disclosure for introducing the heterologous segment(s) into a plant, a plant organ, a plant tissue, or a plant cell. The present disclosure is also directed to use of the host plant(s) of the present disclosure, or use of the composition(s) of the present disclosure, for introducing the RNA vector(s) into a plant organ or plant tissue that does not, prior to said introducing, comprise the RNA vector. In some implementations, the step of introducing the RNA vector comprises grafting a plant organ or plant tissue of a plant that comprises the RNA vector to a plant organ or plant tissue of another plant that does not comprise the RNA vector.

The present disclosure is also directed to a method of making a vector for use with a plant comprising the steps of inserting one or more heterologous segment(s) into an RNA, wherein the RNA is selected from the group consisting of: CYVaV; a relative of CYVaV; other RNA vectors having at least 70% RdRp identity with CYVaV; and another iRNA. The present disclosure also relates to a vector produced by the disclosed method(s).

The present disclosure also relates to the use of an RNA molecule as a vector, wherein the RNA is selected from the group consisting of: CYVaV; a relative of CYVaV; other RNA vectors having at least 70% RdRp identity with CYVaV; and, another iRNA. In some implementations, the RNA is used in the treatment of a plant, for example the treatment of a viral or bacterial infection of a plant, for example the treatment of CTV infection or Citrus greening in a Citrus plant. The RNA is modified with one or more inserted heterologous segment(s), for example an enzybiotic.

The present disclosure is also directed to the use an RNA molecule characterized by being in the manufacture of a medicament to treat a disease or condition of a plant, wherein the RNA is selected from the group consisting of: CYVaV; a relative of CYVaV; other RNA vectors having at least 70% RdRp identity with CYVaV; and, another iRNA. In some implementations, the disease or condition is a viral or bacterial infection of a plant, for example CTV or Citrus greening in a Citrus plant.

The present disclosure is also directed to an RNA molecule for use as a medicament or in the treatment of a disease or condition of a plant, wherein the RNA is selected from the group consisting of: CYVaV; a relative of CYVaV; other RNA vectors having at least 70% RdRp identity with CYVaV; and, another iRNA.

*thamiana* 16C plants were agroinfiltrated with a construct expressing GFP (which is silenced in these plants) and either constructs expressing CYVaV p21 or p81, or constructs expressing known silencing suppressors p19 (from TBSV) or p38 (from TCV). Only p19 and p38 suppress the silencing of GFP, allowing the green fluorescence to be expressed (infiltrated regions identified by circled dashed line in Panel B). Referring to Panel C, northern blot probed with GFP oligonucleotide showed that GFP RNA is still silenced in the presence of p21 or p81.

Figure 14:
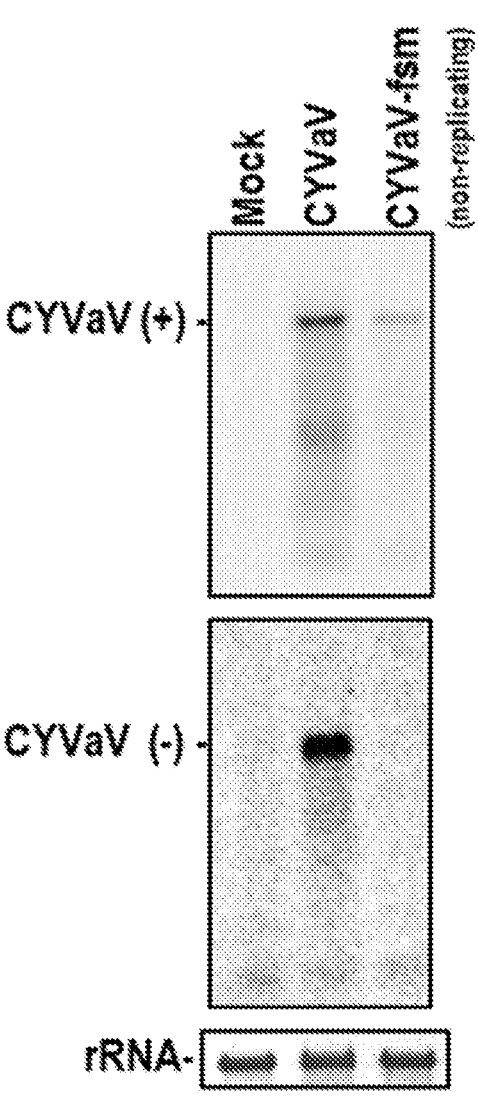

FIG. 14 demonstrates replication of CYVaV in *Arabidopsis* protoplasts. An infectious clone of CYVaV was generated. Wild-type RNA transcripts (CYVaV) or transcripts containing a mutation in the recoding slippery site that eliminates the synthesis of the RdRp (CYVaV-fsm), and thus doesn't replicate, were inoculated onto *Arabidopsis* protoplasts. RNA was extracted and a Northern blot performed 30 hours later. Note that inoculated transcripts of CYVaV-fsm were still present in the protoplasts at 30 hours (whereas in a traditional virus they would be undetectable after 4 hours). Plus strands are shown in Panel A, and minus strand replication intermediate is shown in Panel B.

Figure 15:
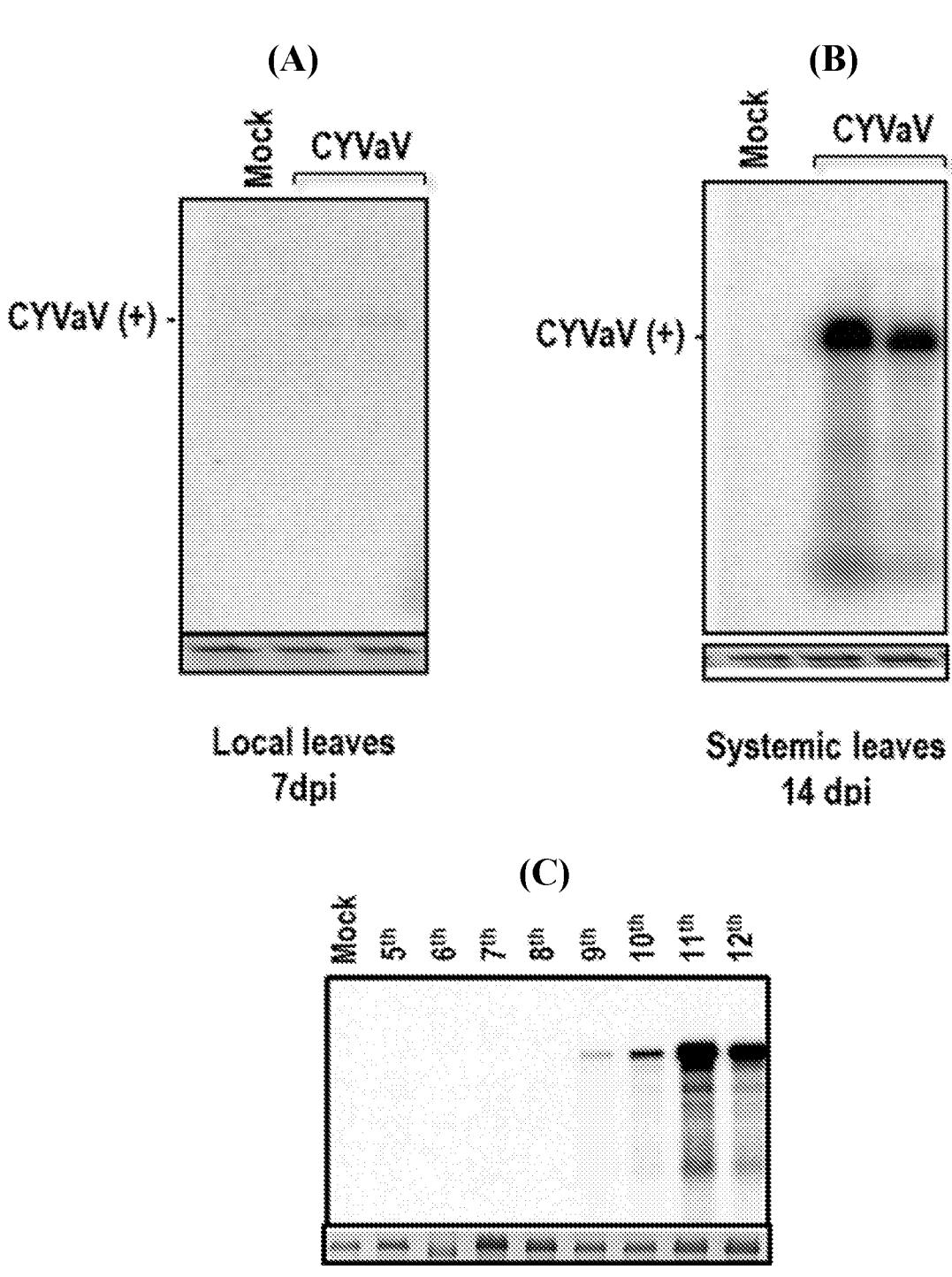

FIG. 15 demonstrates replication of CYVaV in *N. benthamiana*. Referring to Panel A, the level of CYVaV accumulating in the infiltrated leaves of *N. benthamiana* as determined by Northern blot is shown. Referring to Panel B, plants infiltrated with CYVaV sporadically showed systemic symptoms (see FIG. 16). These plants accumulated high levels of CYVaV. Referring to Panel C, the level of CYVaV in individual leaves of a systemically infected plant is shown. Leaves 4 and 5 were agroinfiltrated with CYVaV. Note the substantial accumulation of CYVaV in the youngest leaves.

Figure 16:
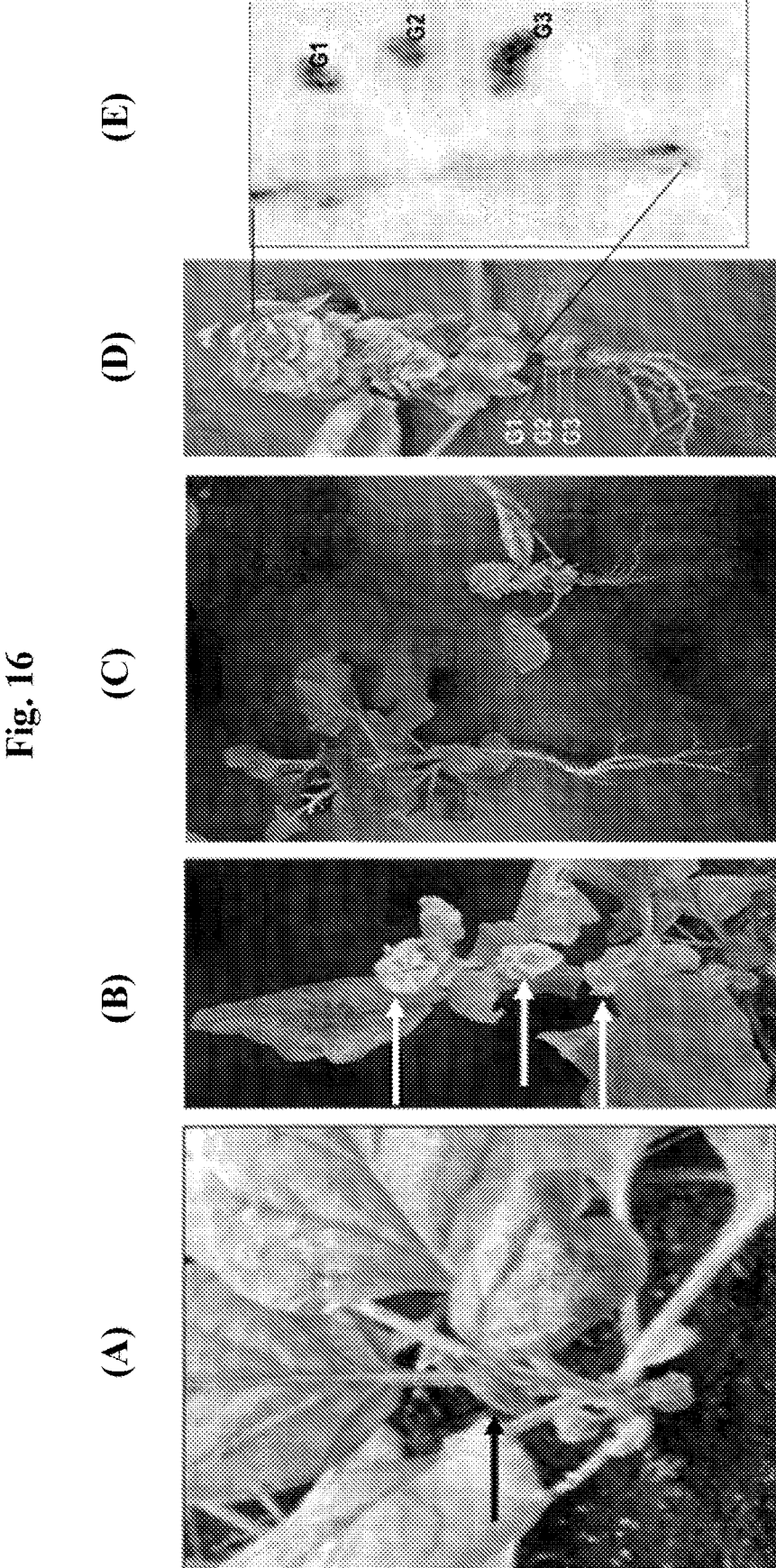

FIG. 16 show symptoms of *N. benthamiana* systemically infected with CYVaV. Leaves 4 and 5 were agroinfiltrated with CYVaV. The first sign of a systemically infected plant is a "cupped" leaf (Panel A), which was nearly always leaf 9. In the following few weeks, leaf galls emerged at the apical meristem and each node of the plant (Panel B). An uninfected plant (Panel C, left) and an infected plant (Panel C, right) of the same age are shown. Systemically infected plants also had root galls (Panel D), containing a substantial amount of CYVaV as evidenced by Northern plant blot (Panel E).

Figure 17:

FIG. 17 is an image of a tomato plant at 53 days post-infection (left) with a plant of the same age (right), and demonstrating the exceptional host range of CYVaV. Sap from a systemically-infected *N. benthamiana* plant was injected into the petiole of a tomato plant. One of four plants showed very strong symptoms and was positive for CYVaV by PCR analysis.

Figure 18:
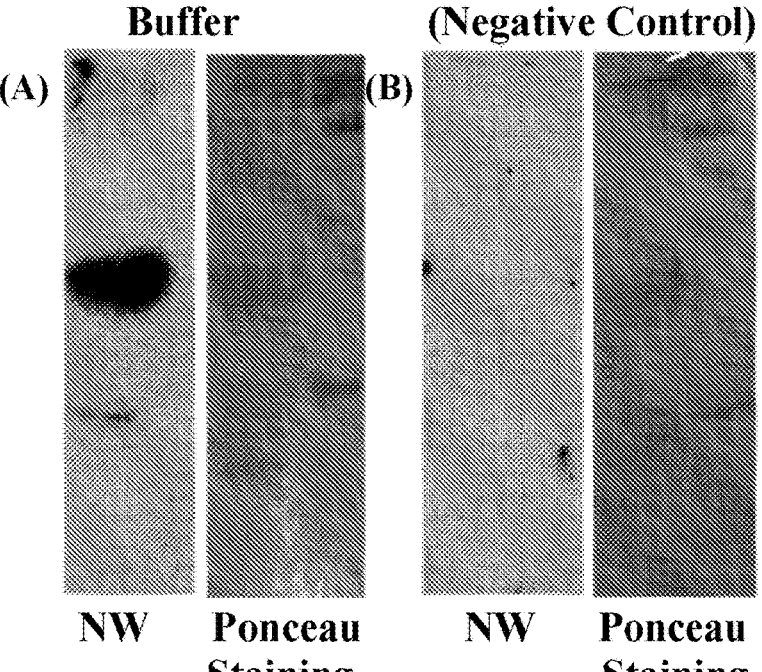

FIG. 18 demonstrates that CYVaV binds to a highly abundant protein extracted from the phloem of cucumber. Referring to Panel A, labeled full-length CYVaV bound to a prominent protein in this northwestern blot. Proteins were renatured after SDS gel electrophoresis. This protein is believed to be a known, highly conserved RNA binding protein containing an RRM motif that is known to chaperone RNAs from companion cells into sieve elements in the phloem of cucumber. Referring to Panel B, no binding was seen when the proteins remained denatured after electrophoresis.

Figure 19:
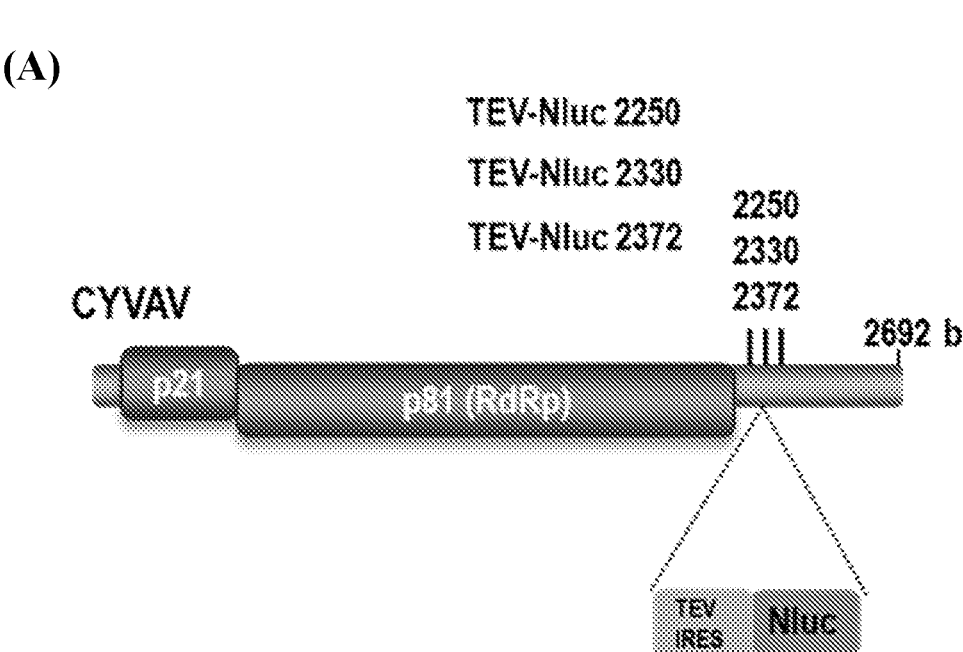
Figure 19:
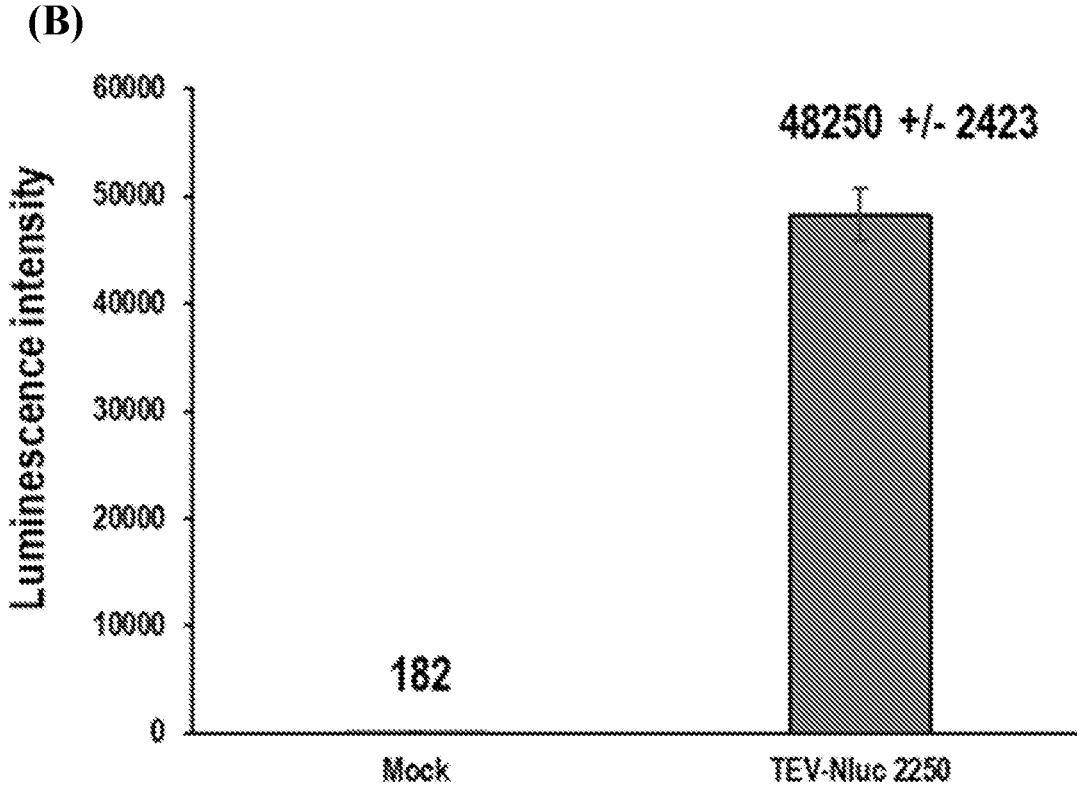
Figure 19:
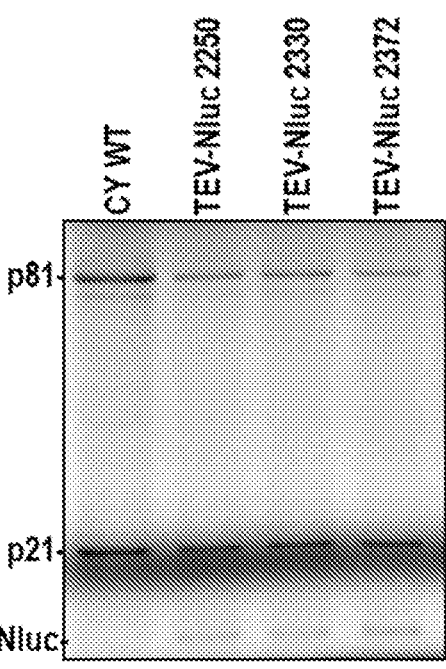

FIG. 19 demonstrates that CYVaV is capable of expressing an extra protein from its 3'UTR using a TEV IRES. The location of three separate inserts (in three separate constructs) of nanoluciferase downstream of the Tobacco etch virus (TEV) internal ribosome entry site (IRES) are shown (Panel A). In vitro translation was measured in wheat germ extracts for the three constructs (Panel B). Note the location of the nanoluciferase protein (Nluc) is near the bottom of the gel. Expression of nanoluciferase was measured in protoplasts in vivo (Panel C). Full-length RNA transcripts of the constructs (Panel A) were transformed into protoplasts; 18 hours later, total protein was extracted and nanoluciferase activity measured in a luminometer.

Figure 20:
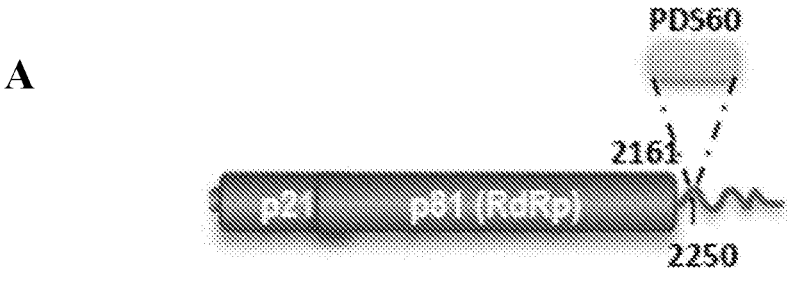
Figure 20:
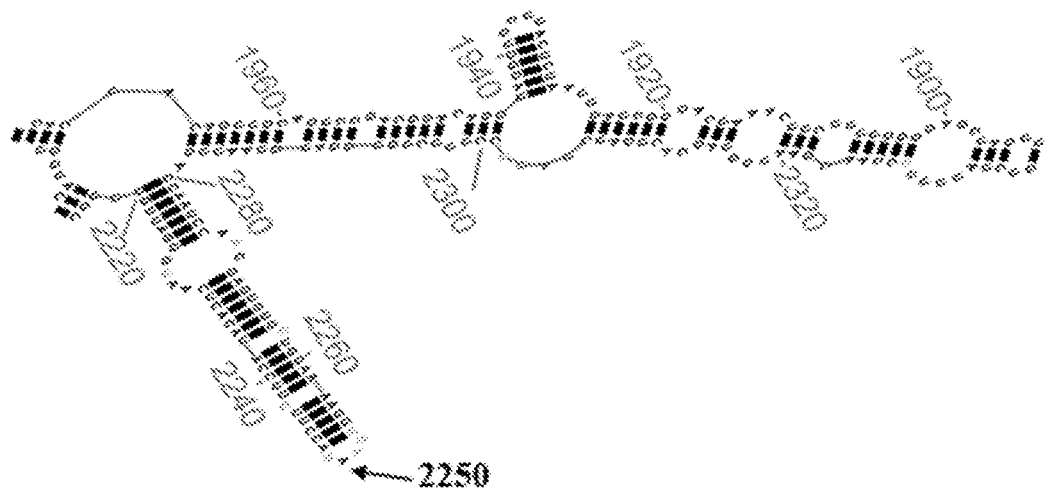
Figure 20:
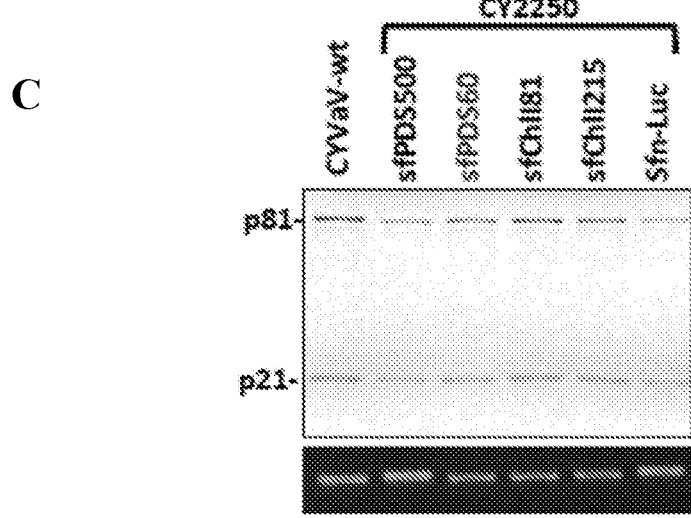
Figure 20:
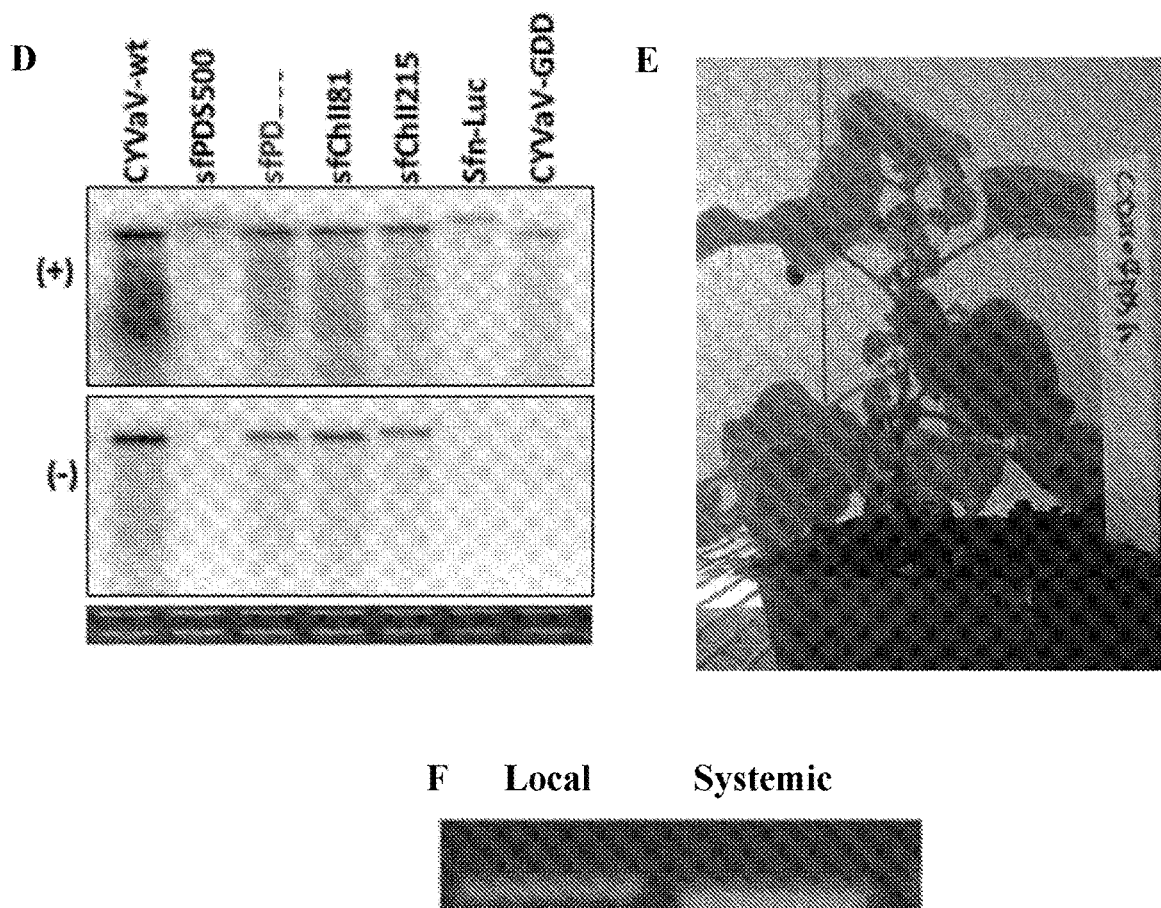

FIG. 20 illustrates a stable hairpin insert at position 2250. A schematic representation of CY2250sfPDS60 is shown in Panel A. The location of the insert in the secondary structure of CYVaV is shown in Panel B, which location corresponds to a region for accommodating inserted hairpins, such as shown by double line box in FIG. 9. Data from wheat germ extract in-vitro translation assay of T7 transcripts from CYVaV-wt, and CYVaV VIGS vectors containing different amounts of sequence at position 2250 are shown in Panel C. For example, construct sfPDS60 demonstrated excellent systemic movement in plants. Northern blot analysis of total RNA isolated from *A. thaliana* protoplasts infected by CYVaV wt and CYVaV VIGS vectors. CYVaV-GDD negative control is shown in Panel D. (+) represents plus-strands and (−) are minus strand replication intermediates. An image of *N. benthamiana* infected by CY2250sfPDS60 is shown in Panel E. RT-PCR products from local leaf and systemic leaf are shown in Panel F. The primer set amplify positions 1963-2654 in the 3' region of CYVaV. The sequence of the insertion region (underlined) of the vector collected from systemic leaf is shown in Panel G, with dashed line boxed sequences on either side of the insert forming the stem of the hairpin.

Figure 21:
Figure 21:
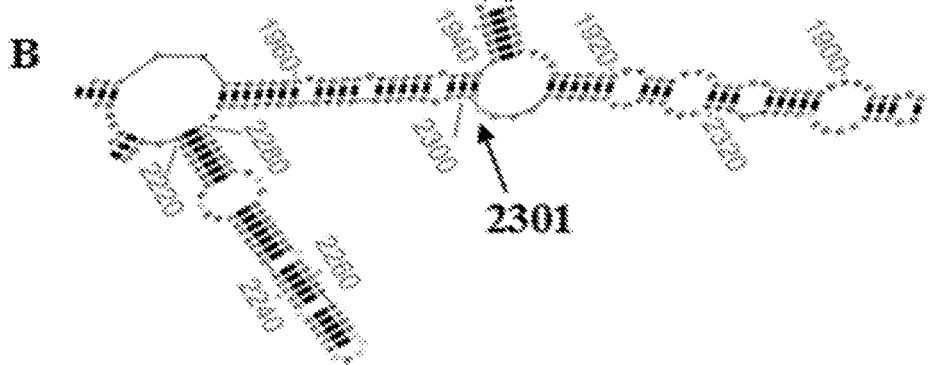
Figure 21:
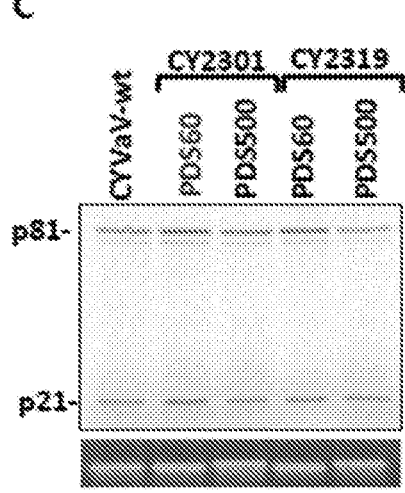
Figure 21:
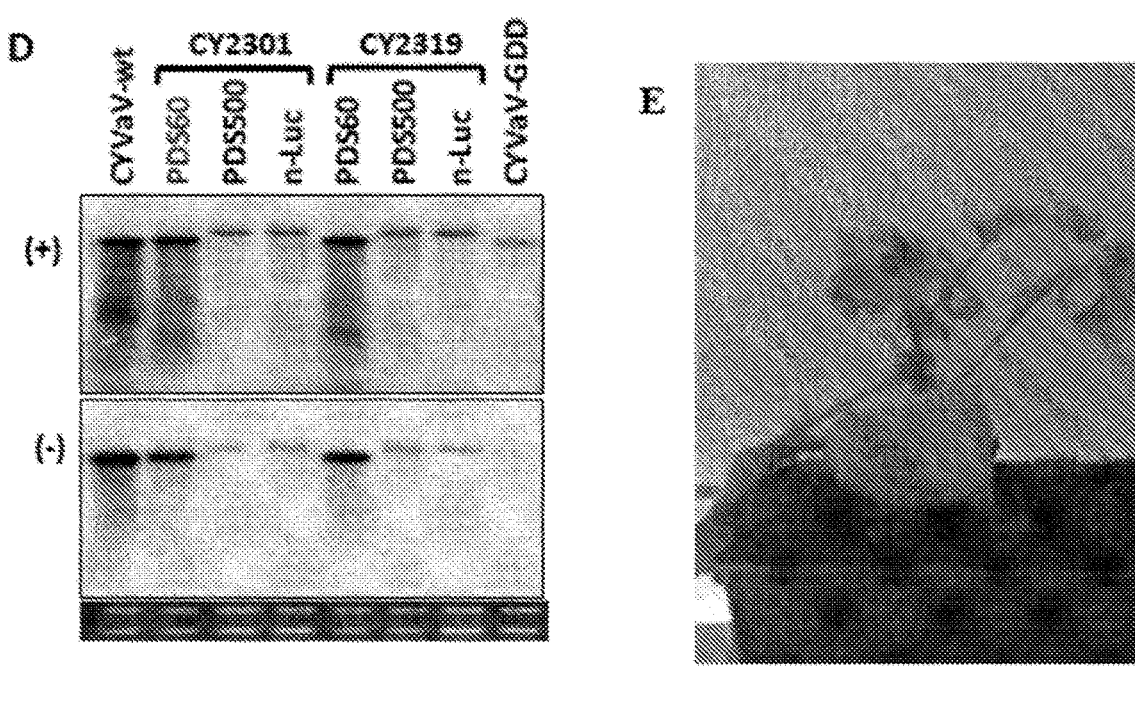

FIG. 21 illustrates a stable hairpin insert at position 2301. A schematic representation of CY2301sfPDS60 is shown in Panel A. The location of the insert in the secondary structure of CYVaV is shown in Panel B, and corresponds to a region for accommodating inserted hairpins, such as shown by double line box in FIG. 9. Data from wheat germ extract in-vitro translation assay of T7 transcripts from CYVaV-wt, and CYVaV VIGS vectors containing different amounts of sequence at positions 2301 and 2319 are shown in Panel C. For example, construct PDS60 demonstrated excellent systemic movement in plants. Northern blot analysis of total RNA isolated from *A. thaliana* protoplasts infected by CYVaV wt and CYVaV VIGS vectors. CYVaV-GDD negative control. is shown in Panel D. (+) represents plus-strands and (−) are minus strand replication intermediates. An image of *N. benthamiana* infected by CY2301sfPDS60 is show in Panel E. RT-PCR products from local leaf and systemic leaf are shown in Panel F. The primer set amplify positions 1963-2654 in the 3' region of CYVaV. The sequence of the insertion region of the virus vector collected from systemic leaf is shown in Panel G, with dashed line boxed sequences forming the stem of the hairpin.

Figure 22:
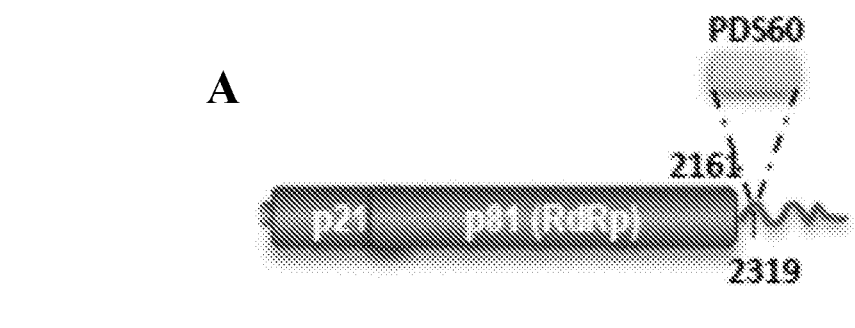
Figure 22:
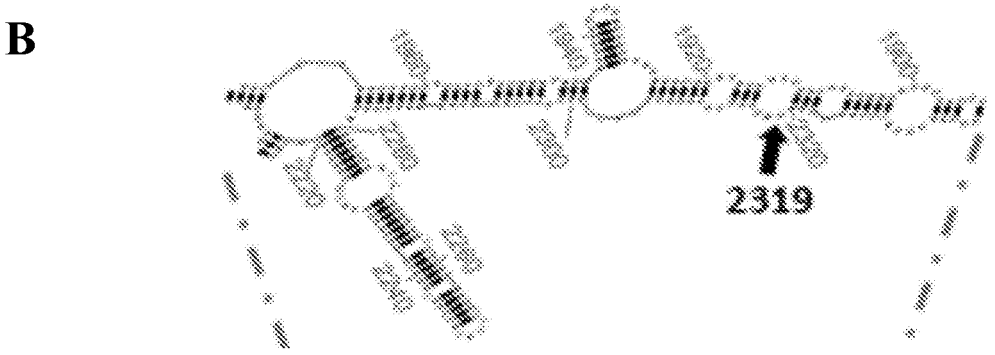
Figure 22:
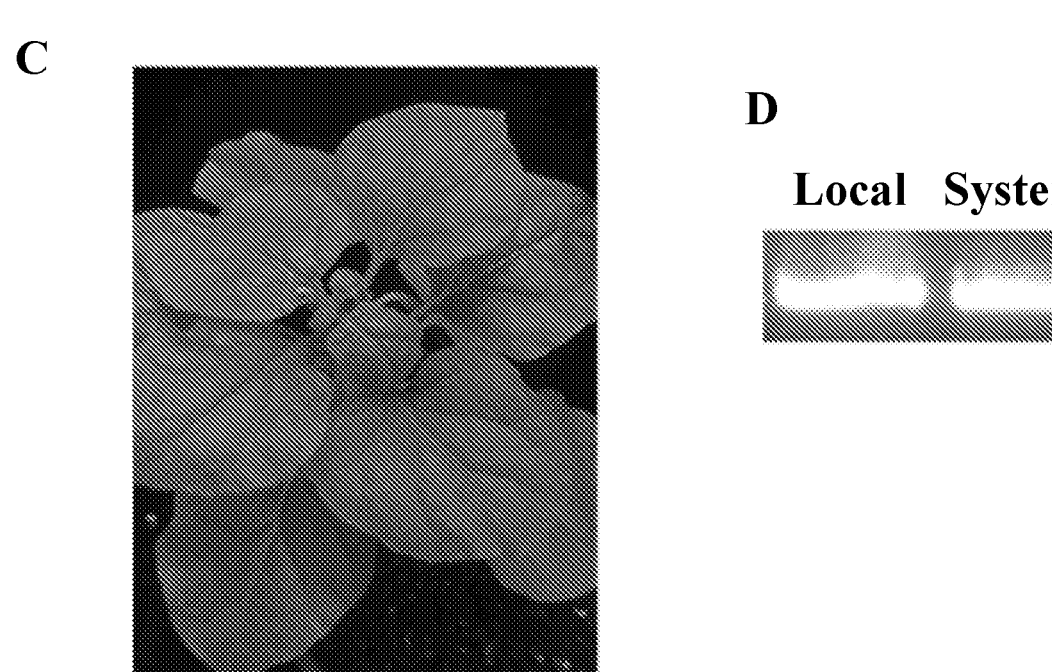

FIG. 22 illustrates a stable hairpin insert at position 2319. A schematic representation of CY2319sfPDS60 is shown in Panel A. The location of the insert in the secondary structure of CYVaV is shown in Panel B, and corresponds to the region for accommodating inserted hairpins shown by double line box in FIG. 9. Data from wheat germ extract in-vitro translation assay of T7 transcripts from CYVaV-wt, and CYVaV VIGS vectors containing different amounts of sequence at position 2301 and 2319 are shown in FIG. 21, Panel C. Northern blot analysis of total RNA isolated from *A. thaliana* protoplasts infected by CYVaV wt and CYVaV VIGS vectors. CYVaV-GDD and negative control is also shown in FIG. 21, Panel D. An image of *N. benthamiana* infected by CY2319sfPDS60 is shown in Panel C. RT-PCR products from local leaf and systemic leaf is shown in Panel D. The primer set amplify positions 1963-2654 in the 3' region of CYVaV.

Figure 23:
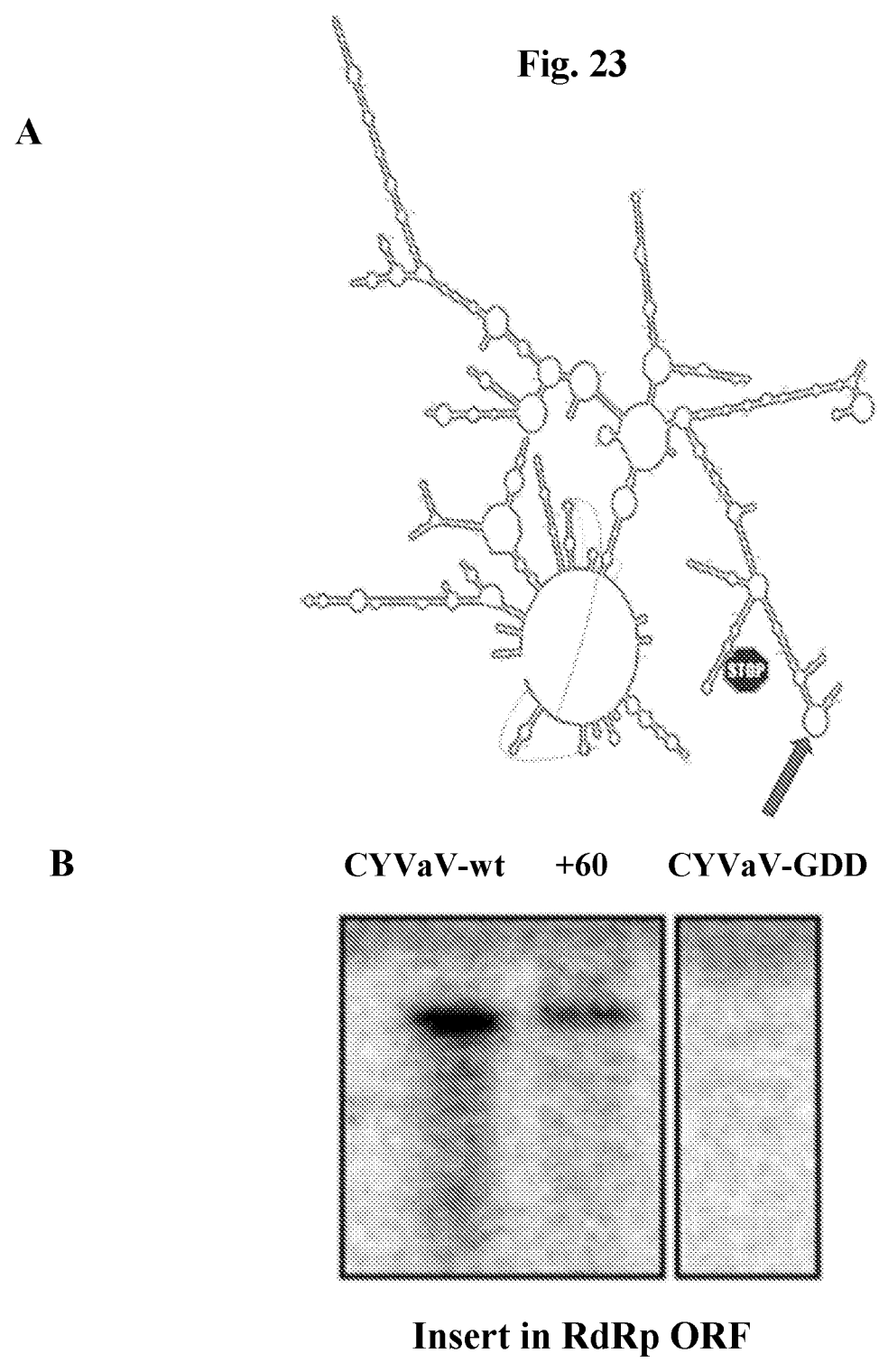

FIG. 23 illustrates the location of a 60 nt insertion (non-hairpin) onto the ORF of the RdRp of CYVaV (Panel A). The location of the insert is indicated by the black arrow. A stop codon, indicated by the black hexagon, was engineered just upstream of the insert to truncate the RdRp. Northern blot of plus-strand RNA levels in *Arabidopsis* protoplasts is shown in Panel B. CYVaV-GDD is a non-replicating control.

Figure 24:
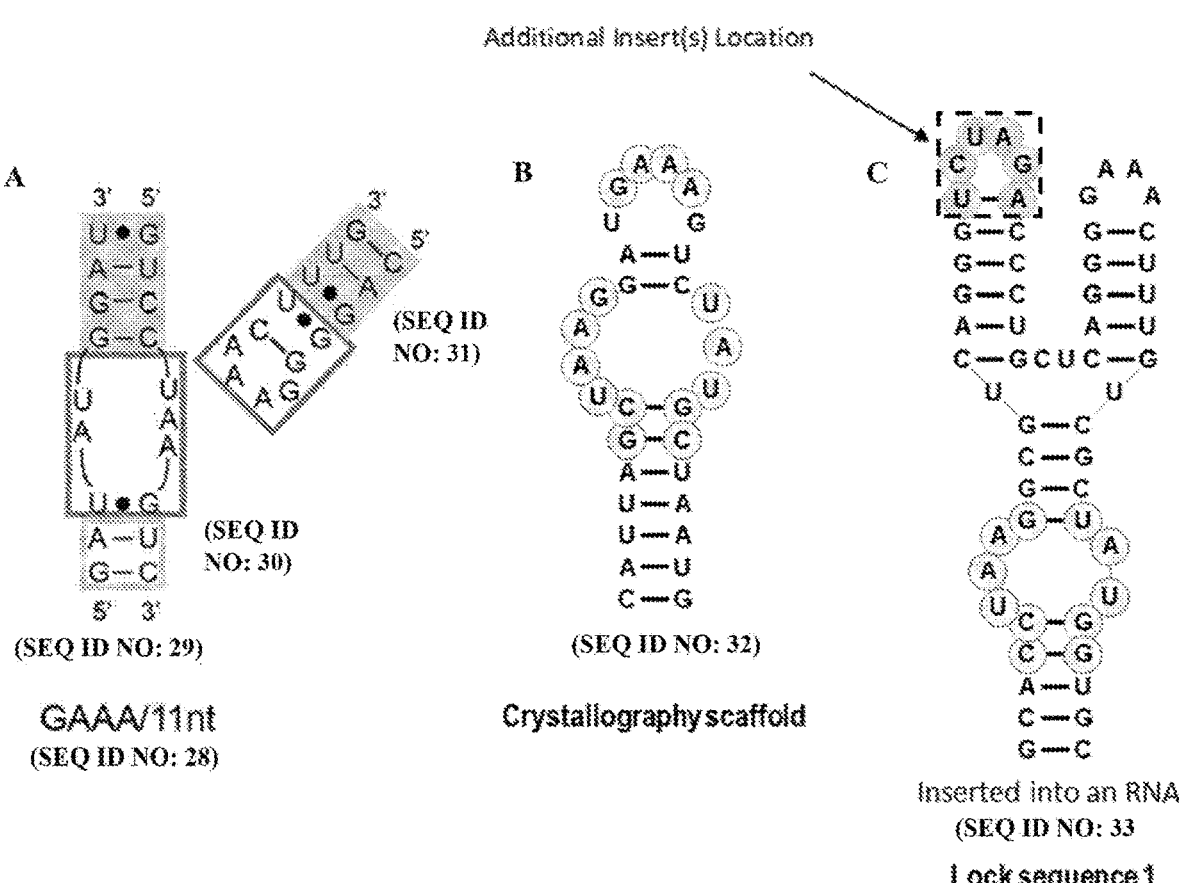

FIG. 24 illustrates a lock and dock sequence for stabilizing the base of inserts. Referring to Panel A, tetraloop GNRA (GAAA) docking with its docking sequence generates an extremely stable structure, and represents a basic lock and dock sequence. Referring to Panel B, use of a scaffold consisting of a docked tetraloop as a crystallography scaffold is shown. Referring to Panel C, a unique lock and dock structure is shown. Inserts (hairpins or non-hairpin sequences) may be added to the restriction site (as identified by dashed line box). Circled bases in the sequences are the docking sequences for the GAAA tetraloop.

Figure 25:
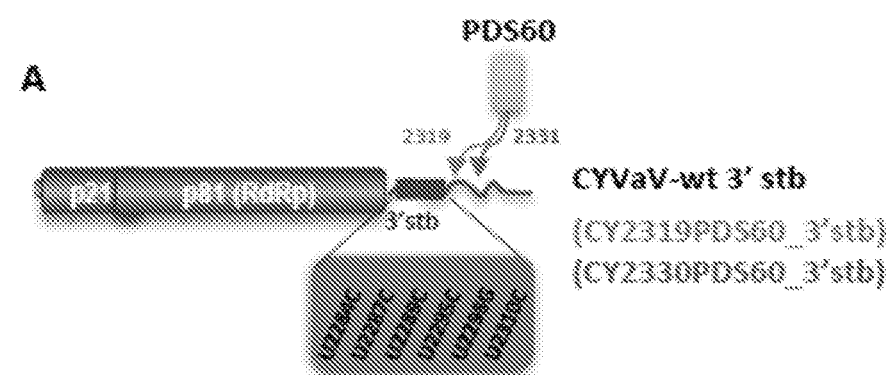
Figure 25:
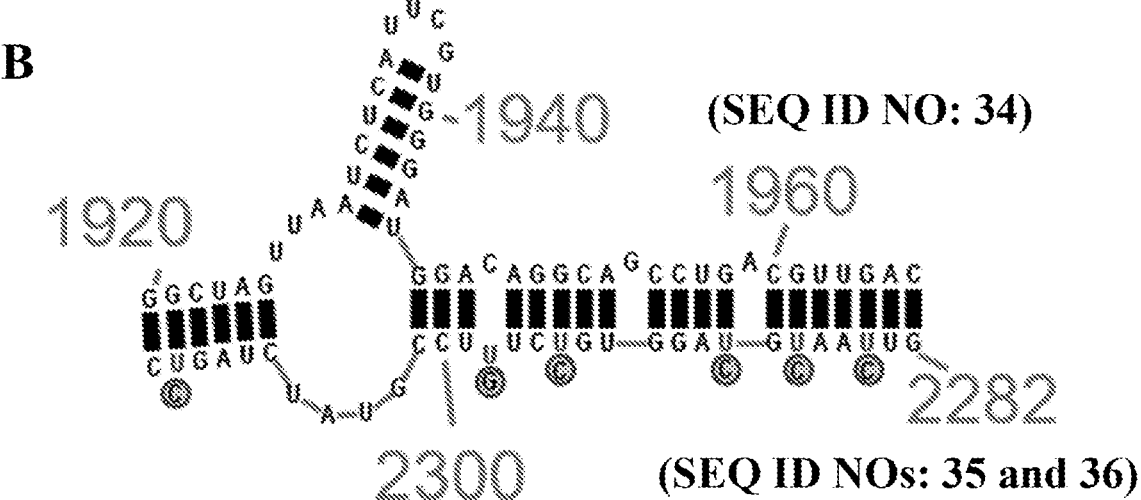
Figure 25:
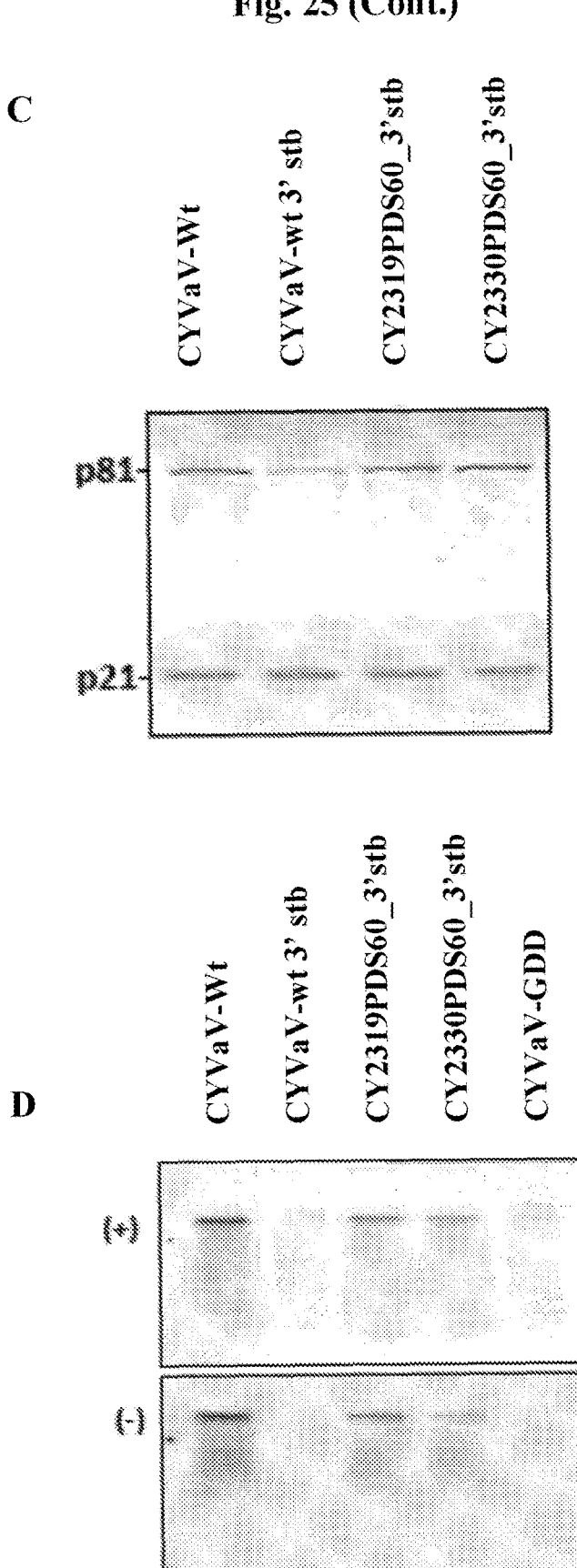

FIG. 25 illustrates that stabilizing the local 3'UTR structure is highly detrimental, but insertion of a destabilizing insert nearby restores viability. Referring to Panel A, a schematic representation of CYVaV-wt. CYVaV-wt 3' stb is the parental stabilized construct containing 6 nt changes converting G:U pairs to G:C pairs. Two insertions of 60 nucleotides were added to the stabilized parental construct at positions 2319 and 2330 forming CY2319PDS60_3'stb and CY2330PDS60_3'stb. Nucleotide changes made to stabilize the structure and generate CYVaV-wt 3'stb are circled in Panel B. Insertion sites are indicated by the arrows for each constructs: left arrow in Panel A indicting insertion site for construct CY2319PDS60_3'stb; right arrow in Panel A indicating insertion site for construct CY2330PDS60_3'stb. Referring to Panel C, data is shown from wheat germ extract in-vitro translation assay of T7 transcripts from the constructs shown in Panel A. Note that p81 levels (the frameshift product) is strongly affected by stabilizing this region. Referring to Panel D, northern blot analysis of total RNA isolated from *A. thaliana* protoplast infected by CYVaV-wt, CYVaV-wt 3'stb, CY2319PDS60_3'stb, CY2330PDS60_3'stb, and CYVaV-GDD (non-replicating control) is shown. (+) represents plus-strands and (−) are minus strand replication intermediates.

DETAILED DESCRIPTION OF EMBODIMENTS

The present disclosure relates to novel infectious agents for use as vectors for plants, compositions comprising a plant infected by the disclosed agent(s), and uses and methods relating thereto. The infectious agents of the present disclosure are sometimes referred to herein as "independently mobile RNAs" or "iRNAs" and exhibit superior characteristics as compared to conventional viral vectors. In accordance with disclosed embodiments, the iRNAs are RNA molecules capable of infecting plants and encoding for an RNA polymerase to sustain their own replication, but lacking the ability to encode for any movement protein or coat protein. In addition, iRNAs do not code for any RNA silencing suppressors.

As used herein, a "host" refers to a cell, tissue or organism capable of being infected by and capable of replicating a nucleic acid. A host may include a whole plant, a plant organ, plant tissue, a plant protoplast, and a plant cell. A plant organ refers to a distinct and visibly differentiated part of a plant, such as root, stem, leaf, seed, graft or scion. Plant tissue refers to any tissue of a plant in whole or in part. Protoplast refers to an isolated cell without cell walls, having the potency for regeneration into cell culture, tissue or whole plant. Plant cell refers to the structural and physiological unit of plants, consisting of a protoplast and the cell wall.

As used herein, "nucleic acid sequence," "polynucleotide," "nucleotide" and "oligonucleotide" are used interchangeably and refer to a polymeric form of nucleotides of any length. Polynucleotides may have any three-dimensional structure, and may perform any function. A "gene" refers to a polynucleotide containing at least one open reading frame that is capable of encoding a particular polypeptide sequence. "Expression" refers to the process by which a polynucleotide is transcribed into mRNA and/or the process by which the transcribed mRNA is translated into peptides, polypeptides, or proteins.

A vector "derived from" a particular molecule means that the vector contains genetic elements or sequence portions from such molecule. In some embodiments, the vector comprises a replicase open reading frame (ORF) from such molecule (e.g., iRNA). One or more heterologous segment(s) may be added as an additional sequence to the vectors of the present disclosure. In some implementations, said heterologous segment(s) is added such that high level expression (e.g., of a particular protein or small RNA) is achieved. The resulting vector is capable of replicating in plant cells by forming further RNA vector molecules by RNA-dependent RNA polymerization using the RNA vector as a template. An iRNA vector may be constructed from the RNA molecule from which it is derived (e.g., CYVaV).

As used herein, an "infection" or "capable of infecting" includes the ability of a vector to transfer or introduce its nucleic acid into a host, such that the nucleic acid or portion(s) thereof is replicated and/or proteins or other agents are synthesized or delivered in the host. Infection also includes the ability of a selected nucleic acid sequence to integrate into a genome of a target host.

As used herein, a "phenotypic trait" refers to an observable, measurable or detectable characteristic or property resulting from the expression or suppression of a gene or genes. Phenotype includes observable traits as well as biochemical processes.

As used herein, "endogenous" refers to a polypeptide, nucleic acid or gene that is expressed by a host. "Heterologous" refers to a polypeptide, nucleic acid or gene that is not naturally expressed by a host. A "functional heterologous ORF" refers to an open reading frame (ORF) that is not present in the respective unmodified or native molecule and which can be expressed to yield a particular agent such as a peptide, protein or small RNA. For being expressible from the vector in a plant, plant tissue or plant cell, the vector comprising a functional heterologous ORF comprises one or more subgenomic promoters or other sequence(s) required for expression.

Various assays are known in the art for determining expression of a particular product, including but not limited to: hybridization assays (e.g. Northern blot analysis), amplification procedures (e.g. RT-PCR), and array-based technologies. Expression may also be determined using techniques known in the art for examining the protein product, including but not limited to: radioimmunoassay, ELISA (enzyme linked immunoradiometric assays), sandwich immunoassays, immunoradiometric assays, in situ immunoassays, western blot analysis, immunoprecipitation assays, immunofluorescent assays, GC-Mass Spec, and SDS-PAGE.

An "exogenous RNA segment" refers to a segment of RNA inserted into a native molecule, whereby the source of the exogenous RNA segment is different from the native molecule. The source may be another virus, a living organism such as a plant, animal, bacteria, virus or fungus, a chemically synthesized material, or a combination thereof. The exogenous RNA segment may provide any function appropriate for a particular application, including but not limited to: a non-coding function RNA, a coding function in which the RNA acts as a messenger RNA encoding a sequence which, translated by the host cell, results in synthesis of a peptide (e.g., a molecule comprising between about 2 and 50 amino acids) or a protein (e.g. a molecule comprising 50 or more amino acid) having useful or desired properties.

As used herein, "movement protein" refers to a protein(s) required for cell-to-cell and/or long distance movement. "Coat protein" refers to protein(s) comprising or building the virus coat.

Similar to umbraviruses, iRNAs do not possess a functional coat protein(s) ORF and/or otherwise encode for any coat protein. In addition, the RNA polymerase of iRNAs is similar to that of umbraviruses. However, unlike umbraviruses, iRNAs do not possess a functional movement protein(s) ORF and/or otherwise encode for any cell-to-cell movement protein(s) or any long-distance movement protein(s) that serves as a stabilization protein for countering nonsense mediated decay.

Conventional viruses lacking coat proteins are generally less stable inside a plant cell given their genomes are vulnerable to the host RNA silencing defense system. However, iRNAs are surprisingly stable in the intracellular environment, which is an important characteristic for an effective vector. iRNAs are also restricted to the inoculated host plant in the absence of a specific helper virus, since without associated virions they are not transmissible by an insect vector. It is believed that iRNAs are encapsidated into virions only when in the presence of a specific helper virus, e.g., such as an enamovirus, including Citrus vein enation virus (CVEV), which is a rarely seen virus in the United States.

In disclosed embodiments, a recombinant plus-sense single stranded RNA vector is provided that comprises a replication element(s) and a heterologous segment(s). The RNA vectors of the present disclosure are capable of accumulating to high levels in phloem, and are capable of delivering a therapeutic agent(s) such as a protein, a peptide, an antibacterial and/or an insecticide (e.g., siRNAs) directly into the plant tissue. In certain implementations, the RNA vector is derived from an iRNA molecule, which lacks the ability to encode for any coat protein(s) or movement protein(s). For example, the vector is derived from and/or includes structural elements of the iRNA molecule known as Citrus yellow vein associated virus (CYVaV), an unclassified molecule associated with yellow-vein disease of citrus.

Thus, disclosed embodiments provide for an iRNA-based vector built on or derived from a plus-sense single-stranded RNA molecule using genetic components from an iRNA molecule, e.g., CYVaV. In addition, the present disclosure is directed to kits and/or mixtures comprising an iRNA-based (e.g. a CYVaV-based) vector(s). Such mixtures may be in a solid form, such as a dried or freeze-dried solid, or in a liquid, e.g. as aqueous solution, suspension or dispersion, or as gels. Such mixtures can be used to infect a plant, plant tissue or plant cell. Such kits and mixtures may be used for successfully infecting a plant(s) or plant cell(s) with the iRNA-based vectors of the present disclosure and/or for expression of heterologous proteins or delivery of other therapeutic agents to such plant or plant cell(s).

The present disclosure also relates to a plant, plant tissue, or plant cell comprising said iRNA-based vector as disclosed herein, and/or a plant, plant tissue, or plant cell comprising a therapeutic agent or heterologous polypeptide encoded or delivered by said vector. The present disclosure also provides for methods of isolating such heterologous polypeptide from the plant, plant tissue, or plant cell. Methods for isolating proteins from a plant, plant tissue or plant cell are well known to those of ordinary skill in the art.

CYVaV was found in four limequat trees in the 1950s independent of any helper virus (Weathers, L. (1957), *A vein-yellowing disease of citrus caused by a graft-transmissible virus*, Plant Disease Reporter 41:741-742; Weathers, L. G. (1960), *Yellow-vein disease of citrus and studies of interactions between yellow-vein and other viruses of citrus*, Virology 11:753-764; Weathers, L. G. (1963), *Use of synergy in identification of strain of Citrus yellow vein virus*, Nature 200:812-813). Further analysis and sequencing of CYVaV was conducted years later by Georgios Vidalakis (University of California, Davis, Calif.; GenBank: JX101610). Dr. Vidalakis's lab conducted analysis on samples collected from previously established tree sources (Weathers, L. G. (1963), *Use of synergy in identification of strain of Citrus yellow vein virus*, Nature 200:812-813) and maintained in the disease bank of the Citrus Clonal Protection Program (CCPP). Studies by the Vidalakis lab to characterize CYVaV were inconclusive. However, many of the infected samples containing CYVaV also contained the enamovirus citrus vein enation virus (CVEV); it was relatively common in the 1950s through 1980s for CCPP personnel to mix infect plants with yellow-vein and vein enation for symptom enhancement.

CYVaV is a small (~2.7 kb) iRNA molecule composed of a single, positive sense strand of RNA. It replicates to extremely high levels, is very stable, is limited to the phloem, and has no known mechanism of natural spread. As such, CYVaV is ideal as a vector platform for introducing an agent(s) into a plant host, e.g., such as a small RNA (e.g., non-coding RNA molecule of about 50 to about 250 nt in length) and/or proteins for disease and/or pest management. The production of proteins that bolster (or silence) defenses, antimicrobial peptides that target bacterium, and/or small RNAs that target plant gene expression or the insect vectors of disease agents provide an effective management strategy. To be efficacious, the proteins and small RNAs should be produced in sufficient quantities and accumulate to sufficient levels in the phloem, particularly small RNAs designed to be taken up by targeted insects or fungal pathogens.

CYVaV is only transmissible from tree to tree by grafting, but has been shown to infect nearly all varieties of citrus with the exception of hearty orange, including but not limited to infecting citron, rough lemon, calamondin, sweet orange, sour orange, grapefruit, Rangpur and West Indian lime, lemon, varieties of mandarin, varieties of tangelo, and kumquat. It produces a yellowing of leaf veins in the indicator citron tree and has no or very mild yellow vein symptoms in sweet orange and other citrus with no reported impact on fruit quality, or otherwise causing harm to trees.

The polynucleotide sequence (bases 1 to 2692) of CYVaV
is presented below (SEQ ID NO: 1):

```
ggguaaauau ggauccuuca ucuuugcccc gugccuguug gcaucaugcc      50
agacaggugu uucgagcauc aacuagcuuc ucaagagagg ugguucgcgc     100
ugcucguaga uggguuacca ugcccaccag ucgccaugca uaugacuuuu     150
caacgagucu aggcauugug auugcugagc cugcagcucg uuuacgacgc     200
cgucugcccu cuguacgaaa gugcgcagag aaguuaguag uccacaagca     250
agucgacacu uugguggacg aauggugcuc uggaauuccc aacccugaua     300
ucguagaagu ugguugggca cuccgucuga gggaccguuu cggucuuccu     350
cccgcuucug agccuacccg gcucaguggu gagagauggg ugcucaaaca     400
acucaauggg guagauccug agucauggaa ugcugaucuu gguaggucag     450
uucauaucca aggagacuac gccccaggga ggaaugccca uaucgcucag     500
gucgcggcga ccuugugguu aacuaggacc uugcaugaca aggccuuggc     550
ucgccaccag gguuuucgcg auuugcagug auuggggucg acgggcuaga     600
ggcaaaagca gugccucuag cuucuggacu ccgacugcuu ccgguuccgc     650
gaccgggaca aagucgacga cugucucaga ccuuguuacu uccaacaccu     700
cgugcucaau ucgugaauca cgcgugcucg gcuaacaacc uuggacgugu     750
gaugaccaca cguguguugc aguacaaggg ccgagauccg auccuucccu     800
cuucugaagc ccuucaccga cuuaaccuuc ggauagcuga gcuauauagg     850
ucuagaccuu cuaccgucua uccauuaagu uaugaagggu uucucaauug     900
cuaugaaggc cgacagcgua cucguuacgc ccaagccguc gagcaguuga     950
ugcgguccac ucuugagccg aaagaugcgc gaguugaaac guucauuaag    1000
aacgagaaau uugacugggc guugaaaggg gaggaggcug auccucgagc    1050
aauccaacca aggaagccga aauauuuggc ugagguugga cggugguuca    1100
aaccuuugga gcgaaucauc uacaaggauc ucaguaaaag guuguauggu    1150
gagggugcug agccguguau cgccaaaggc cuaaaugcau uagaaucugg    1200
agcgacuuug aggcgcaaau gggagaaguu uucuucucca guuugcguuu    1250
cucucgacgc uuccagguuc gaccugcaug uaagcguugg caugcuaaag    1300
uucacacaca agcuauauga cuauuacugu aagucuccca cucuccagcg    1350
cuaucucaaa uggacacucc gcaaccaugg cgucgccucc ugcaaagaau    1400
ugucauauga guaugagguu guuggccgga gaaugagugg ugacauggac    1450
acugcauugg gcaacugcgu cauuaugucg auacuuacau gguuuaugcu    1500
uagugaacuu ggcauuaagc augaauuauu cgauaauggu gacgauuguu    1550
uguucauuug cgagcucac gacgucccca gccccgaggu aauuacaaac    1600
ugguuuucgg acuuuggguu ugugguuagg uuggaaggcg ucacguccgu    1650
guuugagcgu auugaguuuu gccaaacuuc cccaguaugg acugagaggg    1700
guuggcugau guguaggaau auuaagucau ugaguaaaga ccuuacgaau    1750
guuaauucgu gcacgggcuc cacgauugaa uauacccacu gguugaaagc    1800 aguggggaaag ugcgggucaa uacucaaugc ugguguaccu auauuucagu    1850
ccuuucacaa caugcuggaa aggcuuggca cuaacucucg uauugaucga    1900 ggggguuuucu ucaaaucagg gcuaguuaau cucauucgug ggauggacag    1950
```

-continued

```
gcagccugac guugacauca cuacuuccgc ucggcuuucu uucgaagugg    2000
cauucgggau aacacccggg augcaauugg cuauugaacg guacuaugac    2050
ucugucaugg gcucgcugag uaaaauagaa acaacuaagu ggccaauuga    2100
acuaagaaag gaauacgaac acggaaguga gugguacgag gacuuaggcg    2150
uccuaggaug aauaggguca uugguuuacc gaugauaccu guucagaaua    2200
ggauugcucg agcuucguug guuaggguaa cucacauacc uucuuccaua    2250
acuggaaaag gucgugugag caaccuaacc aguuaaugua ggugucuuuc    2300
cguaucuagu cacgauggua agcaacccgu uuaucuguac ggcgcucacc    2350
cguggguagg aaggugaagg uuuuguaucc uuuaggucuu ggacagucug    2400
cgggcuuggg aacgacgccc cgcuagcaac guacugcucu ccuaccggac    2450
ugguagcuua auugucaucu uggagcgaua gcacguggg ccucacccuu     2500 cgcgcguugg acguguugcg ugccccccac agauuuguga aacucuaugg    2550
agcaguuccg cgagccagaa gggaggaugg ccgccuggcg uaauccagga    2600
gcucuggggg gcuuguacuc agaguagcau ucugcuuuag acuguuaacu    2650
uuaugaacca cgcgugucac guggggagag uuaacagcgc cc            2692
```

Figure 1:
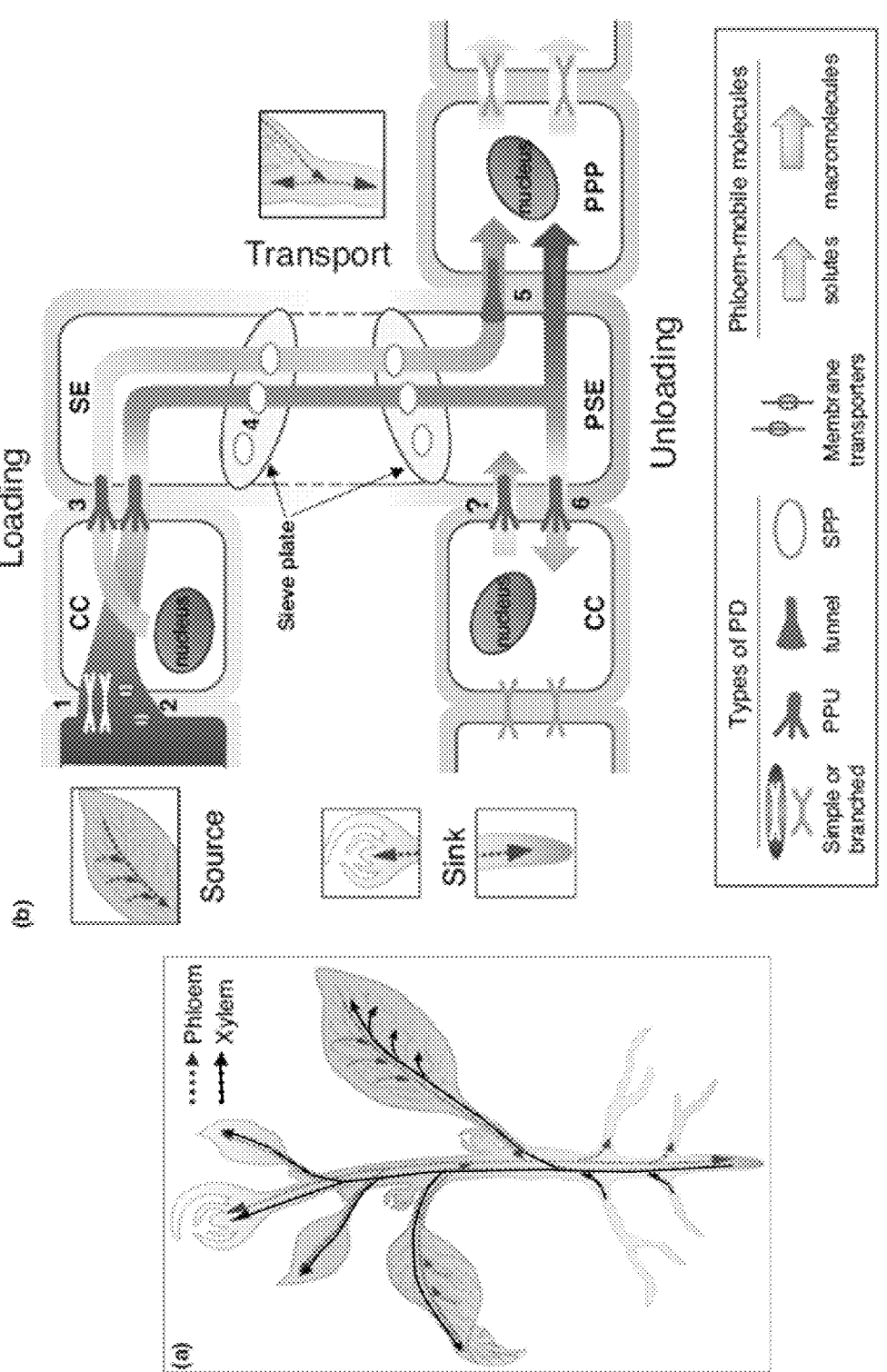
FIG. 1 illustrates schematically the movement pathways through the vascular system of plants (Lee, J. Y. and Frank, M. (2018), *Plasmodesmata in phloem: different gateways for different cargoes*, Curr Opin Plant Biol 43:119-124).
Figure 2:
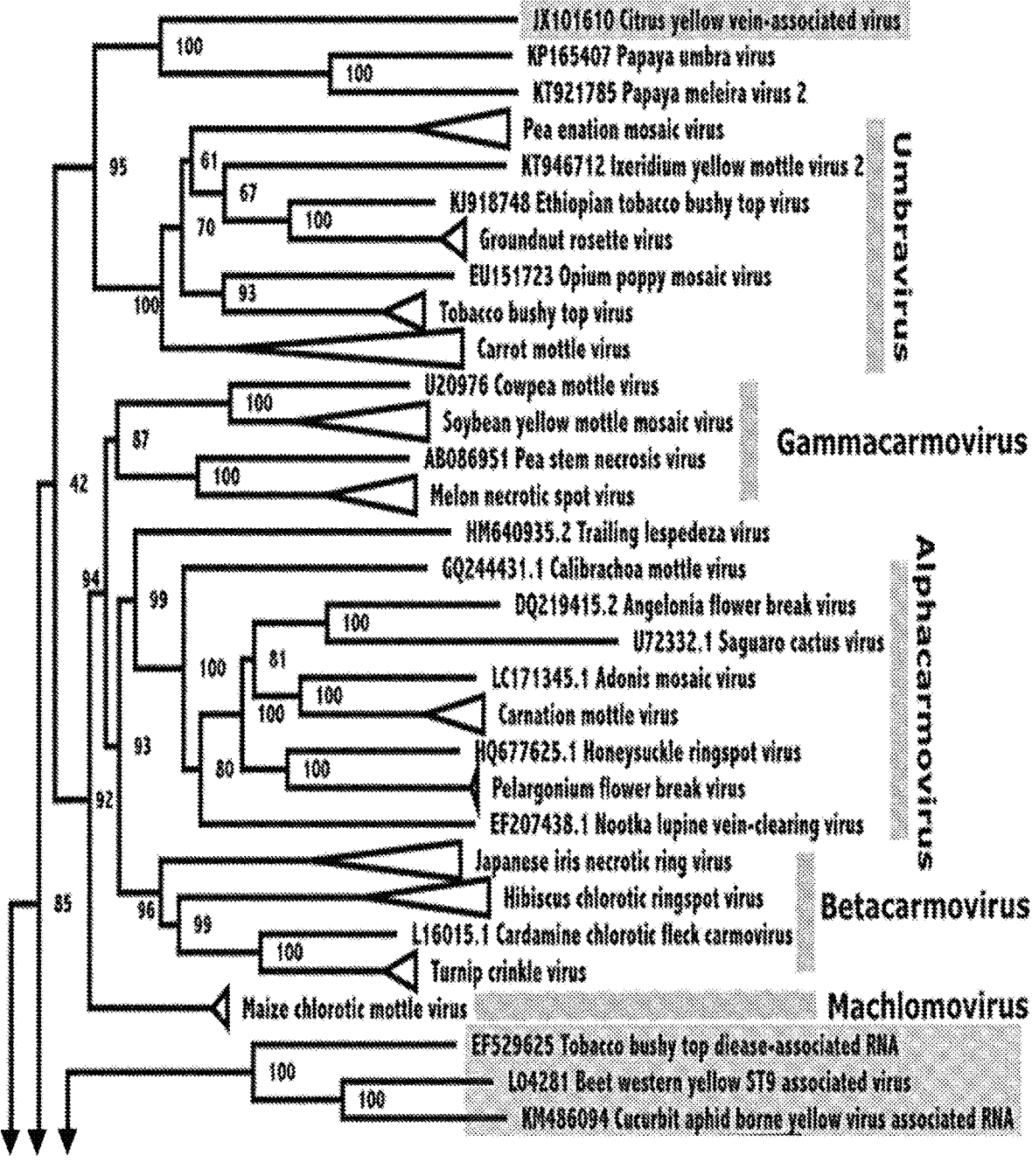
FIG. 2 is a phylogenic tree showing relatedness of the CYVaV with some viruses in the family Tombusviridae.
Figure 2:
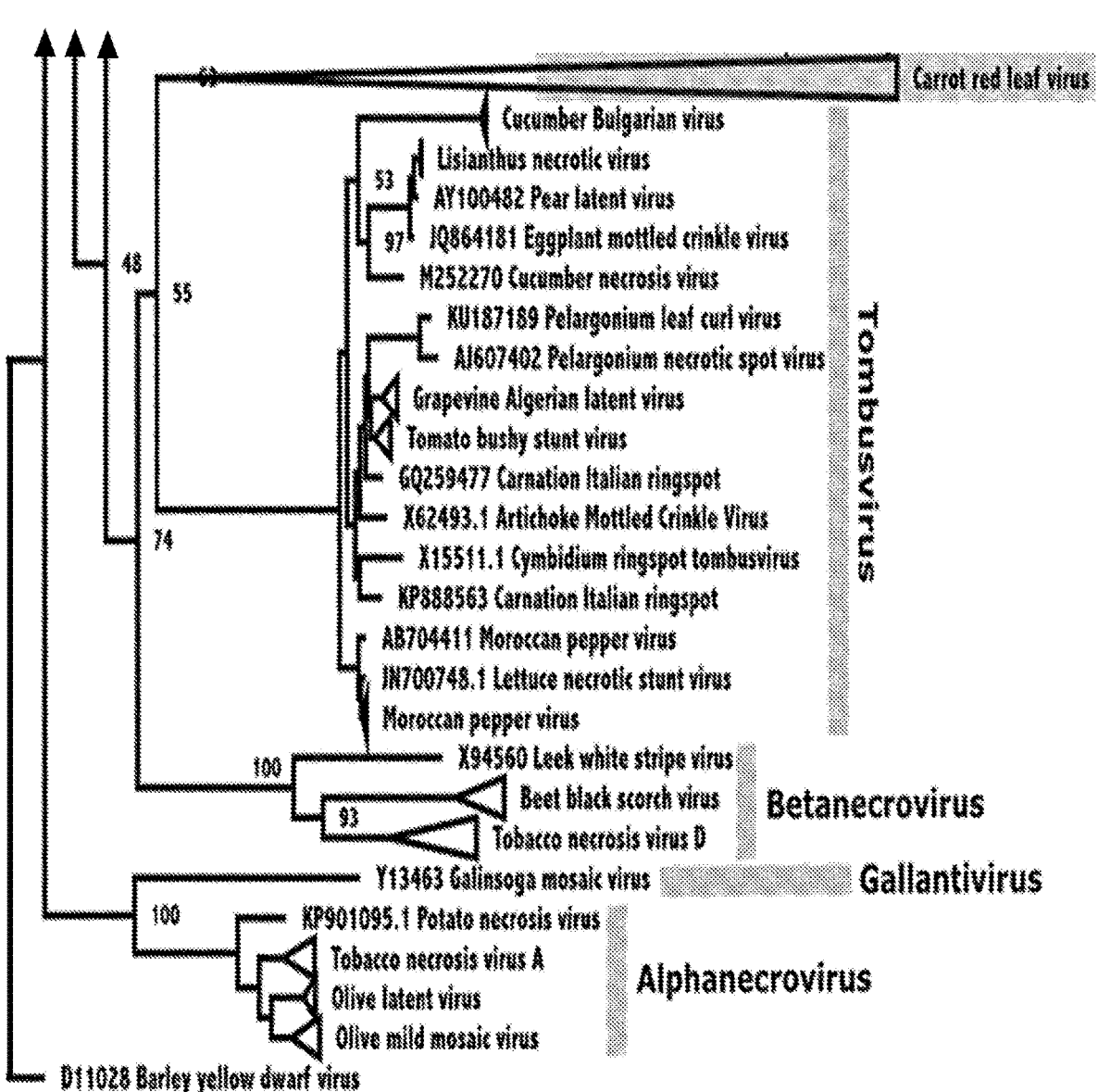
Figure 3:
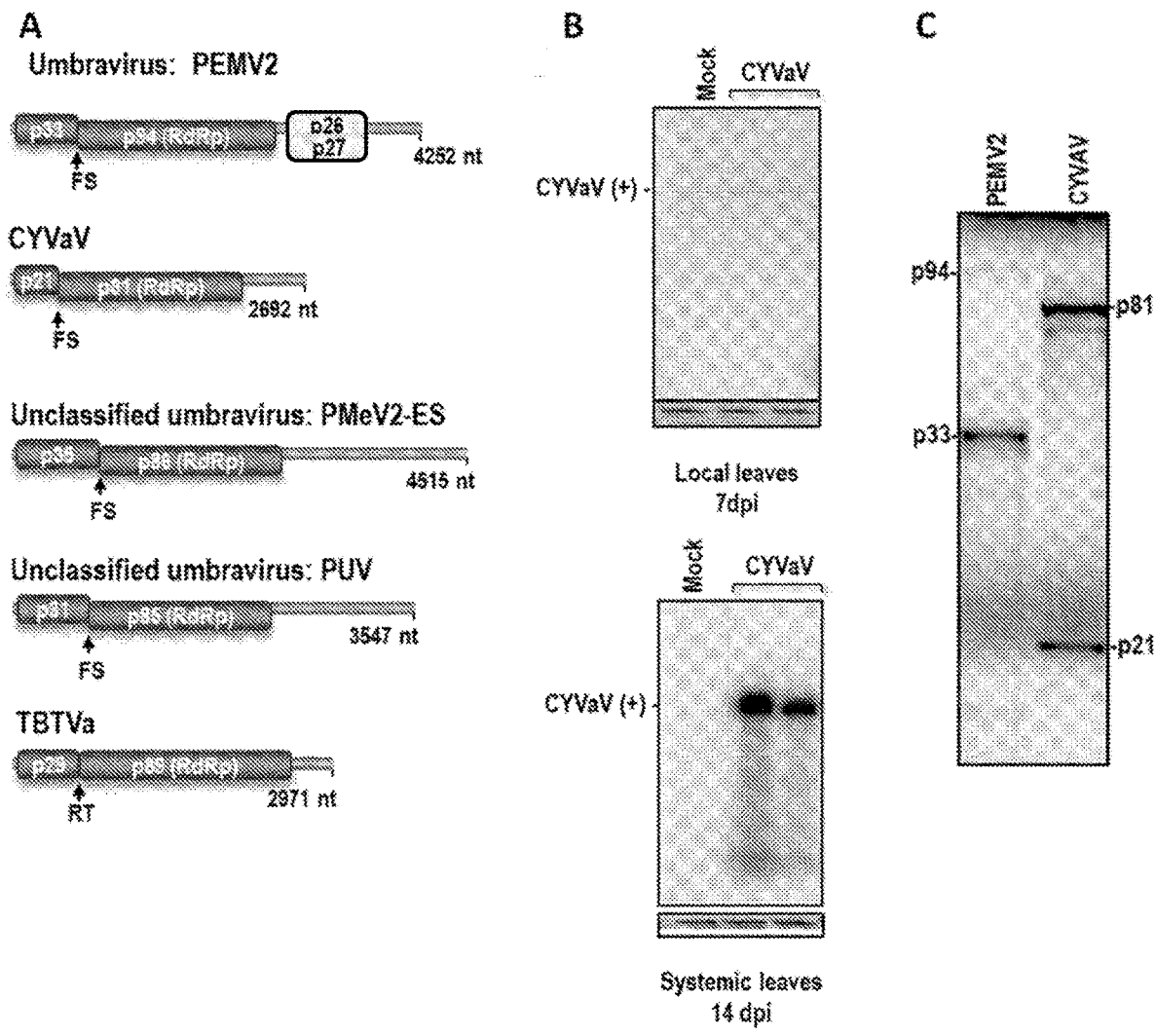
FIG. 3 illustrates schematically the genome organization of CYVaV and similar RNA molecules (Panel A). ORFs encoding for proteins involved in replication are identified in darker grey (p33 and p94 for PEMV2; p21 and p81 for CYVaV; p35 and p86 for PMeV2-ES; p31 and p85 for PUV; p29 and p89 for TBTVa). Umbravirus PEMV2 also possesses ORFs encoding for proteins p26 and p27 involved in movement (identified in light grey boxes). Frameshifting ribosome recording site (FS) and readthrough ribosome recoding site (RT) are also identified. Levels of CYVaV plus (+) strands in infiltrated *N. benthamiana* leaves (Panel B, top) and systemic leaves (Panel B, bottom) are shown. Levels of the RNA-dependent RNA polymerase (RdRp) synthesized by frameshifting in vitro in wheat germ extracts of full-length CYVaV and PEMV2 are shown (Panel C). The difference in levels of p94 from PEMV2 as compared to p81 polymerase produced by CYVaV is significant. The frameshifting site of CYVaV is one of the strongest known in virology and believed to be responsible for its exceptionally high accumulation.

Relatedness of CYVaV with other viruses including Tombusviridae viruses is shown in FIG. 2. Genome organization of CYVaV and similar RNA molecules is illustrated in FIG. 3, Panel A, including PEMV2, PMeV2-ES (GenBank: KT921785), PUV (GenBank: KP165407.1), and TBTVa (GenBank: EF529625.1). The RdRp of CYVaV is most closely related to the umbravirus Pea enation mosaic virus RNA2 (PEMV2). Examination of 5' and 3' sequences of CYVaV revealed considerable similarity to those of umbraviruses, confirming that CYVaV is indeed a complete infectious agent. CYVaV has a plus-sense single stranded RNA genome that only encodes two proteins involved in replication: p21, a replicase-associated protein in related molecules; and p81, the RNA-dependent RNA polymerase (RdRp) that is synthesized by a ribosome recoding (frameshift) event (FIG. 3, Panel A). Levels of the RNA-dependent RNA polymerase (RdRp) synthesized by frameshifting in vitro are shown for PEMV2 and CYVaV. The difference in levels of p94 (RdRp) from PEMV2 as compared to p81 from CYVaV is significant (FIG. 3, Panel C). The frameshifting site of CYVaV is one of the strongest known in virology and believed to be responsible for its exceptionally high accumulation.

The polynucleotide sequence of the 3' end of CYVaV (bases 2468 to 2692) is presented below (SEQ ID NO: 2):

```
ucu uggagcgaua gcacguggg ccucacccuu cgcgcguugg acguguugcg ugccccccac agauuuguga aacucuaugg agcaguuccg cgagccagaa gggaggaugg ccgccuggcg uaauccagga gcucuggggg gcuuguacuc agaguagcau ucugcuuuag acuguuaacu uuaugaacca cgcgugucac guggggagag uuaacagcgc cc
```

The polynucleotide sequence of the 3' Cap Independent Translation Enhancer (3' CITE) of CYVaV (bases 2468 to 2551) is presented below (SEQ ID NO: 3):

```
ucu uggagcgaua gcacguggg ccucacccuuc gcgcguugg acguguugcg ugccccccac agauuuguga aacucuaugg a
```

The 3' end (and 3' CITE) of CYVaV comprises the following conserved polynucleotide sequence(s) (bolded and underlined above):

```
                                                (SEQ ID NO: 4)
auagcacug;
and/or (SEQ ID NO: 5)
gauuuguga.
```

The polynucleotide sequence of CYVaV that encodes for protein p21 (bases 9 to 578) is presented below (SEQ ID NO: 6):

```
         au ggauccuuca ucuuugcccc gugccuguug gcaucaugcc agacaggugu uucgagcauc aacuagcuuc ucaagagagg ugguucgcgc ugcucguaga uggguuacca ugcccaccag ucgccaugca uaugacuuuu caacgagucu aggcauugug auugcugagc cugcagcucg uuuacgacgc cgucugcccu cguguacgaaa gugcgcagag aaguuaguag uccacaagca agucgacacu uggguggacg aauggugcuc uggaauuccc aacccugaua ucguagaagu ugguugggca cuccgucuga gggaccguuu cggucuuccu cccgcuucug agccuacccg gcucaguggu gagagaugg ugcucaaaca acucaauggg guagauccug agucauggaa ugcugaucuu gguaggucag uucauaucca aggagacuac gccccaggga ggaaugccca uaucgcucag gucgcggcga ccuugugguu
```

-continued

```
aacuaggacc uugcaugaca aggccuuggc ucgccaccag gguuuucgcg auuugcag
```

The amino acid sequence of protein p21 is presented below (SEQ ID NO:7):

```
MDPSSLPRACWHHARQVFRASTSFSREVVRAARRWVTMPTSRHAYDFSTSL

GIVIAEPAARLRRRLPSVRKCAEKLVVHKQVDTLVDEWCSGIPNPDIVEVG

WALRLRDRFGLPPASEPTRLSGERWVLKQLNGVDPESWNADLGRSVHIQGD

YAPGRNAHIAQVAATLWLTRTLHDKALARHQGFRDLQ
```

The polynucleotide sequence of CYVaV that encodes for protein p81 (bases 752 to 2158) is presented below (SEQ ID NO: 8):

```
                                       augaccaca cgugugUUgc aguacaaggg ccgagauccg auccuucccu cuucugaagc ccuucaccga cuuaaccuuc ggauagcuga gcuauauagg ucuagaccuu cuaccgucua uccauuaagu uaugaagggu uucucaauug cuaugaaggc cgacagcgua cucgUUacgc ccaagccguc gagcaguuga ugcgguccac ucuugagccg aaagaugcgc gaguugaaac guucauuaag aacgagaaau uugacugggc guugaaaggg gaggaggcug auccucgagc aauccaacca aggaagccga aauauuuggc ugagguugga cggugguuca aaccuuugga gcgaaucauc uacaaggauc ucaguaaaag guuguauggu gagggugcug agccguguau cgccaaaggc cuaaaugcau uagaaucugg agcgacuuug aggcgcaaau gggagaaguu uucuucucca guuugcguuu cucucgacgc uuccagguuc gaccugcaug uaagcguugg caugcuaaag uucacacaca agcuauauga cuauuacugu aagucuccca cucuccagcg cuaucucaaa uggacacucc gcaaccaugg cgucgccucc ugcaaagaau ugucauauga guaugagguu guuggccgga gaaugagugg ugacauggac acugcauugg gcaacugcgu cauuaugucg auacuuacau gguuuaugcu uagugaacuu ggcauuaagc augaauuauu cgauaauggu gacgauuguu uguucauuug cgagucucac gacgucccca gccccgaggu aauuacaaac ugguuuucgg acuuuggguu ugugguuagg uuggaaggcg ucacguccgu guuugagcgu auugaguuuu gccaaacuuc cccaguaugg acugagaggg guuggcugau guguaggaau auuaagucau ugaguaaaga ccuuacgaau guuaauucgu gcacgggcuc cacgauugaa uauacccacu gguugaaagc aguggggaaag ugcgggucaa uacucaaugc ugguguaccu auauuucagu ccuuucacaa caugcuggaa aggcuuggca
```

```
cuaacucucg uauugaucga gggguuuucu ucaaaucagg gcuaguuaau cucauucgug ggaaggacag gcagccugac guugacauca cuacuuccgc ucggcuuucu uucgaagugg cauucgggau aacacccggg augcaauugg cuauugaacg guacuaugac ucugucaugg gcucgcugag uaaaauagaa acaacuaagu ggccaauuga acuaagaaag gaauacgaac acggaaguga gugguacgag gacuuaggcg uccuagga
```

The amino acid sequence of protein p81 is presented below (SEQ ID NO:9):

```
MTTRVLQYKGRDPILPSSEALHRLNLRIAELYRSRPSTVYPLSYEGFLNCY

EGRQRTRYAQAVEQLMRSTLEPKDARVETFIKNEKFDWALKGEEADPRAIQ

PRKPKYLAEVGRWFKPLERIIYKDLSKRLYGEGAEPCIAKGLNALESGATL

RRKWEKFSSPVCVSLDASRFDLHVSVGMLKFTHKLYDYYCKSPTLQRYLKW

TLRNHGVASCKELSYEYEVVGRRMSGDMDTALGNCVIMSILTWFMLSELGI

KHELFDNGDDCLFICESHDVPSPEVITNWFSDFGFVVRLEGVTSVFERIEF

CQTSPVWTERGWLMCRNIKSLSKDLTNVNSCTGSTIEYTHWLKAVGKCGSI

LNAGVPIFQSFHNMLERLGTNSRIDRGVFFKSGLVNLIRGMDRQPDVDITT

SARLSFEVAFGITPGMQLAIERYYDSVMGSLSKIETTKWPIELRKEYEHGS

EWYEDLGVLG
```

The replication element of CYVaV (e.g., that encodes for protein p81) comprises the following conserved polynucleotide sequence(s) (highlighted and underlined above):

```
                                    (SEQ ID NO: 10)
          cguuc;

(SEQ ID NO: 11)
          gaacg;

(SEQ ID NO: 12)
          gguuca;

(SEQ ID NO: 13)
          ggag;
          and/or (SEQ ID NO: 14)
          aaauggga.
```

In addition, CYVaV may additionally comprise the following conserved polynucleotide sequence(s) (highlighted and underlined above):

```
                                    (SEQ ID NO: 15)
          ucgacg;
          and/or (SEQ ID NO: 16)
          cuccga.
```

Figure 10:
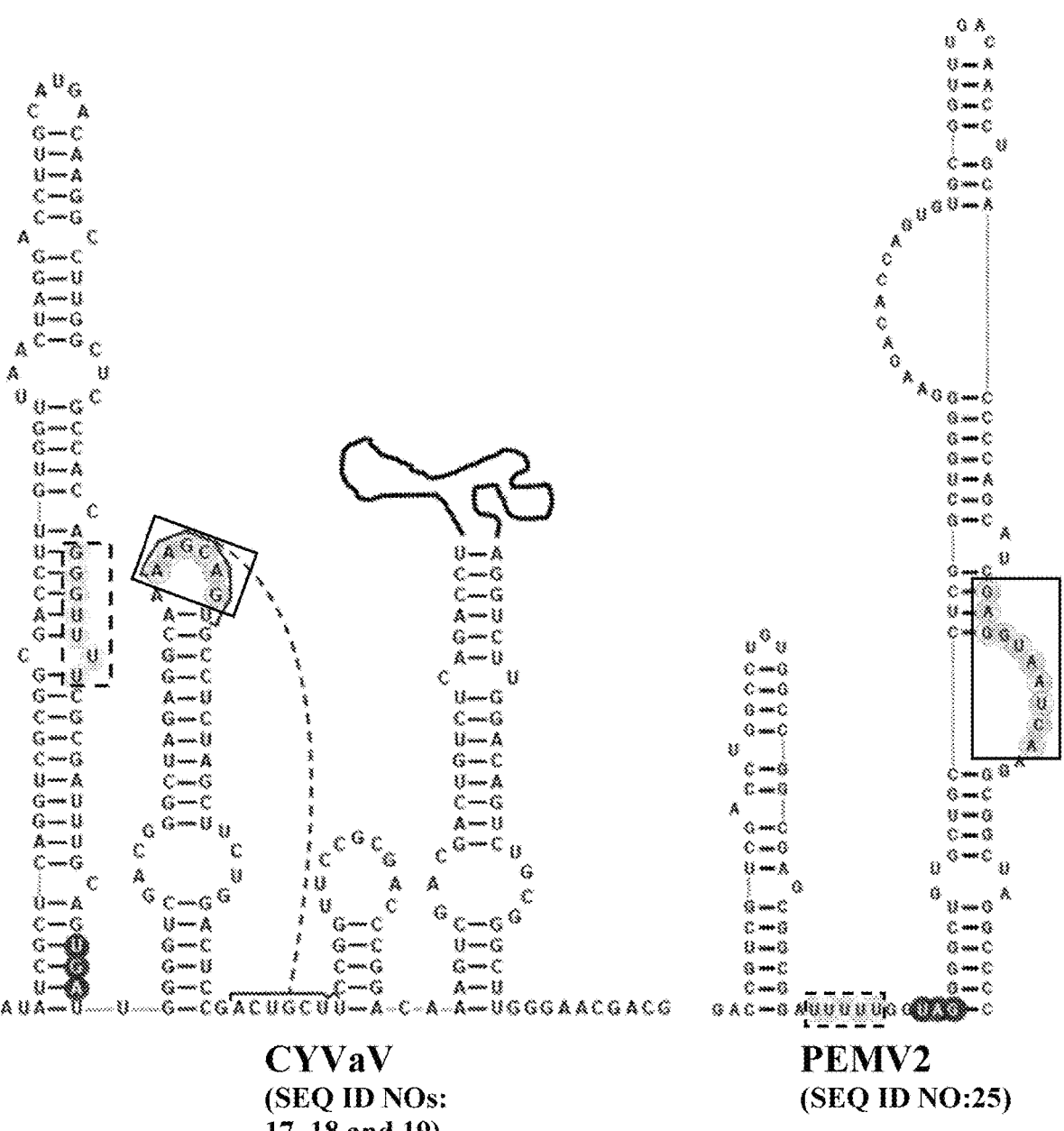
FIG. 10 illustrates schematically the structure of the recoding frameshift sites in CYVaV and PEMV2 (Panel A). CYVaV has multiple conformations of the structures in this region (see FIG. 9) with only one shown. Slippery site is identified by boxed dashed line, and stop codon bases are in black circles. Bases identified by boxed solid line engage in long-distance interaction with the 3' end.

The polynucleotide sequences of recoding frameshift sites of CYVaV (see also FIG. 10) is presented below:

```
                                      (SEQ ID NO: 17)
ucgcucaggucgcggcgaccuuguggguuaacuaggaccuugcaugacaagg ccuuggcucgccaccagggguuuucgcgauuugcagugauuggggucgacgg gcuagaggcaaaagcagugccucuagcuucuggacuccgacugcuuccggu uccgcgacccgga
```

```
                                      (SEQ ID NO: 18)
caaagucgacgacugucucagaccu
```

```
                                      (SEQ ID NO: 19)
aggucuuggacagucugcgggcuugggaacgacg
```

Figure 4:
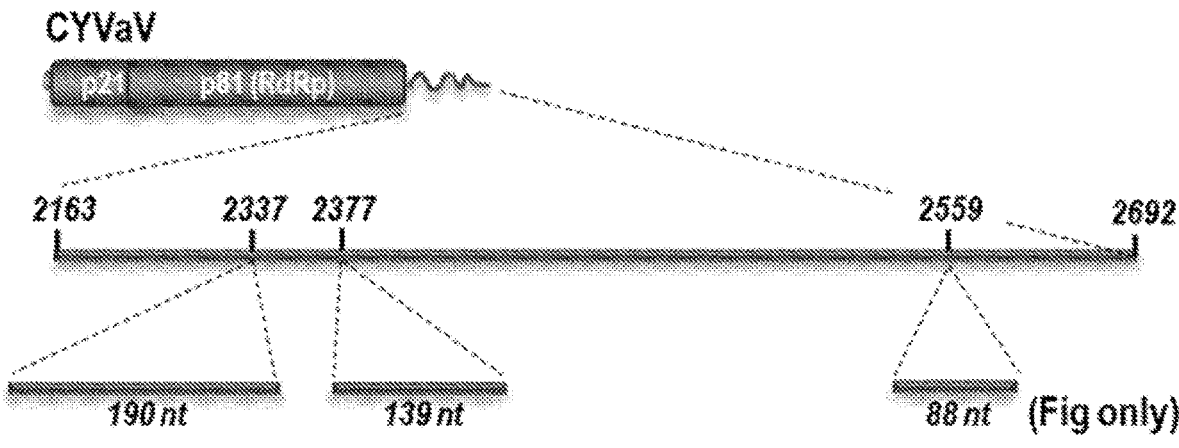
FIG. 4 illustrates schematically the genome organization of additional iRNAs and close relatives of CYVaV identified in Opuntia, Fig trees, and Ethiopian corn. The iRNA relatives all have inserts in the 3'UTR and other nucleotide changes that result in the generation of an ORF that encodes for a protein (p21.2) of unknown function.
Figure 4:
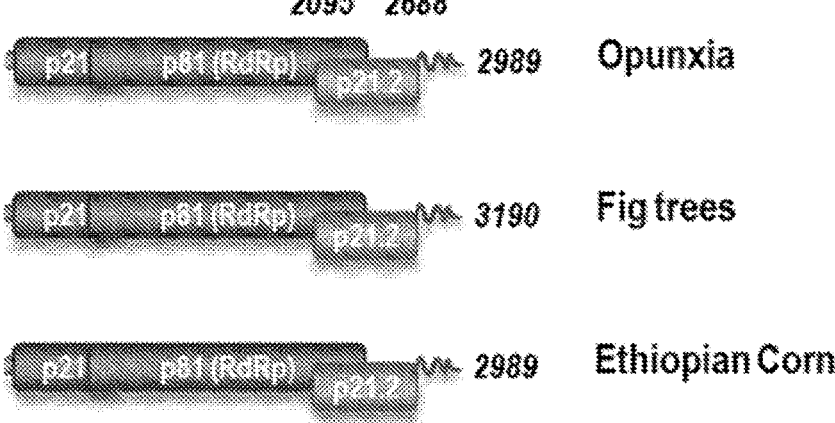

Highly similar iRNAs have also been found in Opuntia (GenBank: MH579715), fig trees, and Ethiopian corn (FIG. 4), suggesting an unusually large or possibly even unlimited host range for the RNA vectors disclosed herein.

The polynucleotide sequence of a similar iRNA identified in a fig tree (sometimes referred to herein as "iRNA relative 1" or "iRNA r1") is presented below (SEQ ID NO: 20):

```
aaauauggauucgauaucaaugcccgucgccugcuggucaaaagccaggca ggucuugcguacaccagcuaacuuuuccaaaggggguagugaaggcugcgua ccggugggucaacaugcccagagccaaauaugucagagaugucuccacgag ucuuggcauaguugucgcugagccuguugcugccgugcgccguuagaugcc uucgauaagcagccuugcggaggaguugguaacacgccagagcgucgacac ucuggguggacgauuggugucucggacuuuccaacccugacaacaacgugga gguugguugggcacuucgucugagggaccgcuuuggucuuccucccgccuc ugagcccacaaggcucagguggugagaugagauggggugcuuaaacaacucaaugg gguagacccggagucguggaauguugaucugcaaagcguuuucgaagacgc ucaggaugacuuccaucgggacuacgcccaaggaggaaugcccaaaucgc ucaaauugcggcaacccuauggcuuacaaagaccuuagucgauaaggcuuu agcacgccaucaggauuuucgcaguuugcagugauuggggucgacgggcua gaggcuaaagcagugccucuggcugcuggacuccgacugcuuccgguuccg cggcccggacaaagccgacggcugucucaaaccuugcuacucccuacuccc cgugcucaauuugucaaucacgcuaacucagguaauaauuugggggcuguu uugaccacacgggugaugcaauacaaaggccgagacccgauacuacccucc caggaagcccugcgcaaacuuaaccuucggauaggacaguuguauaagucu agaccauccacugucuauccccugaguuaugaugggguuucuuaauuguuau gauggccgacagcguacucgcuacgcucaugccgucgagcaauugaugggu gccgcucugaccccaaaagaugcgcgaguugagacguucauuaagaacgag aaguuugauugguuguugaaggggagacgaggcugauccucgugcaauccaa ccuaggaagccgaaauauuuggccgagguuggucgaugguucaaaccguug gagcgaaucaucuacaaggaucucaguuugcguuuguacggugauaacgcu gaaccuugcauugccaaaggcuuaaaugcauuggaaucagggggcuacguug agacguaaaugggaaaaguucgcuaauccuguuugugguuucauuggaugcu ucucguuucgaccugcacguaaguguuggcuuguuaaaguucacgcauaaa
```

25

The polynucleotide sequence of an iRNA identified in another fig tree (sometimes referred to herein as "iRNA relative 2" or "iRNA r2") is presented below (SEQ ID NO: 21):

cucccacgacugccggagcucugcagaauuccaccgggggguaccuggcuua caccaggguggccauccuccccuucuggcucgcggaauagcucuauagaguuu cacaaaucucugagggggcacucgccacguccaucgcgcguugagugaggcu cacagugcuaucgcucccagaauucgggauaaauauggaagaaacuucuuu gcccaaagccugcuggaucaaaagccaggcaggucuugcguacaccagcua acuuuuccaaaggggguagugaaggcugcguaccgguggucaacaugccca gagccaaauaugucagagaugucuccacgagucuuggcauaguugucgcug agccuguugcugccgugcgccgucagaugccuucgauaagcagccuugcgg aggaguugguaacacgccagagcgucgacacucugguggacgauuggguc ucggacuuuccaacccugacaacaacguggagguugguugggcacuucguc ugagggaccgcuuuggucucccucccgccucugagcccacaaggcucagug gugagagaugggugcuuaaacaacucaauggaguagaccccgaaucuugga augacgacuaugcguucgaagacgcucaggaggauuuucaacgggaauacg ucccgggaaggaaugcccauauugcugcaacugcggcaacucuauggcuga caaagaccuuguaugacaaggcuuuaguucgccaucaggguuuucgcaguu ugcagugauuggggucgacgggcuggaggcuaaagcagugcuccagcgc uggacuccgacugcuuccgguuccgcggcccggacaaagccgacggcuguc ucagaccuuacuacuuccuacuccccgugcuacuuuugucaaucaugcaaa uucaggcaauaaucuugagcguguuuugaccacacgggugaugcaauacaa aggccgagacccgauacuacccucccaggaagcccugcgcaaacuuaaccu ucggauaggacaguuguauaagucuagaccauccacugucuauccccugag uuaugaggguuucuuaaauuguuaugauggccgacagcguacucgcuacgc ucaugccgucgagcaauugaugggugccgcucugacccaaaagaugcgcg aguugagacguucauuaagaacgagaaguuugauugguuguugaagggaga cgaggcugauccucgugcaauccaaccuaggaagccgaaauauuuggccga gguuggucgaugguucaaaccguuggagcgaaucaucuacaaggaucucag uuugcguuuguacggugauaacgcugaaccuugcauugccaaaggcuuaaa ugcauuggaaucaggggcuacguugagacguaaaugggaaaaguucgcuaa uccuguuugugucauuggaugcuucucguuucgaccugcacguaagugu uggcuuguuaaaguucacgcauaaauuguacgacuauuacugcaagucucc cacucucaacgauaucucaaaauggacacuccgcaacuccgguaucgccuc cguuaaggaaaaaucauaugcguaugagguugaaggccguagaaugagugg cgacauggacaccgcauuaggcaacuguaucaucaugacgauauuaacuug guuuaugcuuagcgaacuuggcgugcggcaugagcuuuucgauaauggua ugauuguuuguucauuugcgaagaaaaagacguaccuagccccgagacgau caugaacugguuugcggauuuuggguuugugguuagguuagaaggcgucgu guccguguuugagcgcauugaguucugccaaacaucgccuauauggacuga ucgagguuggcugaugugguagaaacaucaagucuuugaguaaggaucuuac

26 gaacguuaauucgugcacuggcuccacuguugaauacacccauugguugaa agcaguuggaaagugguggaucggugcucaaugcgggugugccuauauuuca gucauuucacaacauguugaugcgauugggauacgaauucgcguauagaucg cgggguauucuuuaggguguggacuuguuaaucucauucgugggauggacag acaaccugaaguugagaucacuacuuccgcucgucuuucuuuugaagguggc auucgggaucacuccecggcaugcaauuggcuauugagcaauuuuaugacuc agucgugggcccucuggguaaaauaaaaucuguaaaauggccaauagaucu aagaaaggaauacgauuacggaagcgcguгguucgaagaccaaggcguccu agggugaacaaggaacucggauuaccgaugacaccuguucaaacuagaaug guucgggucaacguugaccaaggagaccaacauaccuucuacugcaaauagc ggucgggaggcuguuugggcuuguuggccaaucaacuuuagugucuuuccg caacuagccucacucgugaauaaaccguuauacuggcgugugucuccagugug caaguugcaauggagccugcaaugucuucuuccacccaacauuguggugu ggcucaguucuucuggggccuucacauaacggugaugggguucgguaacgu cuuuaagcucuugcguucuuguaacuauacgcggcgcucucccgugggagg aaacgugauggucaaauggccuaucugcaugcccuucauucuuaacgauga ugcgcacaagaacacaggauuaaccgccugugugaucauugcagucaccaa uacuggugugcuaacuggucaaucuuggacggagauucuguugaaugugga guauacgccccgcuagcaucguacugcucuccuaccggacugguagccguu uaguuaucuuggagugauagcacugugggcgccacauuugacgcgcauugga cgcagacaaugucccuccacagauuugugaaucucuauggagcguaaccu cggucucucuauagcuuguccgaacaggaaauggacauaaaauaauugcug uuccaacacguugugugugguaaagaaguuauagauguggugcgccagacaa guggauggcaaccuggaguaauccaggcgcucuggggggcuuauacucgga gugcauuacugcuuuagaccguuaaucucaagaaccaugugugucgcaugg ggaggauuaacggcgcccaauucccuuguuaguuuagguacgccuuggucu ucgaaccacgc The polynucleotide sequence of an iRNA identified in maize (sometimes referred to herein as "iRNA relative 3" or "iRNA r3") is presented below (SEQ ID NO: 22):

gggguaaauauggagaaccagcacacccauguuugcccacggucguuccug cgaaccugcagggcgauccucgcggcuccagccaacuacggucgugaugug gucaaaaucgccuacaaaugggcaucacgaaaccccgccaccgcccccccga agugccgagaauccaucggggucguugucggaagcgcuguggacuucuug agcgcuccucgcaagcguuuagaagaccgcgcagagcaguuggugcaagac gaccggggucgaccggaucguccgcgaguggggagcuaggaaccgcugacucc cgaauuccggaaguugaguggcauaccgucugcgcgaccgcuucggcguc guguccgccagcgagccugcuaggcaaacuggugagaggugggggcucaag caacuagagggauuggagggggggaguuccgcugcauacccauugagcca uucuuuggugaugcaccggcccccguccauagcccugggagcaacagcgug -continued auugcugcuauugcggcgacccuuuggaugacgccuacccgccuugaccgg gcguugagacgucaccagggguuuucgcaacuagcggugaucggagucgacg gagugucugcuuuagcggugcaggcaucuucugaacuccgaccgcuacggg uuggggcgaccccgucaaagucgacgucguucguggucucugacuaugccag cacccaaguccuguuucgugaaccacgcuaacucugaccacaaucucaaaa cggucauggaaaacagggugcucaaguacaaaggccaagaacccgcaaagc cccggguagaagccuauaagcagcucuaugaaaggauacgaccgcgauauc guucucuaccugacacggucuauccucuaucauaugauggcuuccucaagu gcuacuccggacguaggcgaacacgauacgaacaggccguccaggaguuga gaaacgcgccacucacacccgaagaugcugucguuuccacguucaucaaga acgagaaauucgauuggcuccaaaagaaagaacuugcggaucccagagcua uccaaccucggaaaccgaaauaccuggccgaaguugggaggugguucaagc cucuggagcacauaauguauaaagacuuggcaaaacgguuguacggucagg augcguugccuugcauagcgaaagggcugaacgcuagagaaacggcugaag ugcuccgagccaaaugggacaaguucgcuucucccguuugcgucucgcugg augccagucgguucgaucugcauguaaguccugacgcauugcgguuuacgc accgccuguaccacaaguauugccaaagucggcaacuccgcaaguaccuag aauggacgcugagaaacgcuggcgucgccucaugucugaaagcgcuuauc aguaugagguugaggggagacgcaugaguggcgacauggacaccgcacucg gcaacugcuacuuaugcucugcuugacauggaacuuccucgaucaacaua acaucaagcaugagauaauggacaacggagaugacugcuuguucaucugug aagcugccgaugugccaaccgacaagcaaaucauggacuacuaccucgacu uuggguucgugguucgguuggaaggaaaggugucuguguucgagcgaauag aguucugucaaaccaguccggguguugacugcuaauggauggcguaugguua gaaauuugaaguccauugcgaaggaccucugcaaugugaacauggcgacug ggucacucagugaauacacgcguggcuuaaagccguggggaaucuguggua gaauccugaacgauggggguuccaaucuucuccgccuuccacaacaugcugg ugcgacauggaacgaacucacgaauagauagagcgguguucugggaaugug gacugacaaacuugaucaaaggcaugaguuucgagcaacuggaaaucacug ucgcugcgcgcgaguccuuuuaucuggcauacgguaucacaccggcgagac aacucgcgauugaagaguauuacgacucacuccagggcccggugggguaaaa uacaacuucaugaauggccacuacaacucaaagaggaauacgcgugcggcg ccgagugguucgaaggagacggcgagcgggcuugaggcccgcuggcuugcc cuucgugcccggcagcucucgcacgguucggacugcgcucguccucgagaa ccacuugccgauguccucggcacaguuggggucaagaggccguugcguauuc uaucccgugcaaguuugaaacaugccuacgauccugacucucgccaccac uccgcucuauuggcguaucaccgccaucacugucgcgauggagccugcaaa guccacaucgacccaaauugccggugugggggaaugcugauucauuucaguc ugccaccacaacgguuuugggaacguguuuaagaaaaugcgcgcuuugaa uuucgugagacgcucggcgcccggaggcaaucuucagguacgcuggccuau caauauggacuggaucuccgcauccgacacggacaaggauagcacaaaagu -continued gcccucgcuauucuuugccgugaccaacccaggugugaucgaaaccaaaca aggggacagugaggccugguuggaaugggaguuggagcuggaguacauagu uggaggcuaggaacgacugcccgcuugagaucgacucucccguggugaggu accacccacucagcugugucagccgguuggagaaacucguggugcauagca cuguuggccccugccuagcgugugcugugggaaagccccaacagauuugug aaacacuggaguugucgacccgcgagacgugcggcucgaguugucgcuucc ccgugaggggggcugccgggggguagagaaauauucccgguauuuauccgc uaagaccuacgcgcgacgaaacuggcg Note that iRNA relatives (e.g., iRNA r1, iRNA r2, and iRNA r3) may comprise conserved polynucleotide sequence(s) (bolded and underlined above): auagcacug (SEQ ID NO: 4); and/or gauuuguga (SEQ ID NO: 5). For example, the iRNA molecule comprises both of conserved polynucleotide sequence(s): auagcacug (SEQ ID NO: 4); and gauuuguga (SEQ ID NO: 5).

In addition, iRNA relatives (e.g., iRNA r1, iRNA r2, and iRNA r3) may comprise conserved polynucleotide sequence(s) (bolded and underlined above): cguuc (SEQ ID NO: 10); gaacg (SEQ ID NO: 11); gguuca (SEQ ID NO: 12); ggag (SEQ ID NO: 13); and/or aaauggga (SEQ ID NO: 14). For example, the iRNA molecule comprises all of conserved polynucleotide sequence(s): cguuc (SEQ ID NO: 10); gaacg (SEQ ID NO: 11); gguuca (SEQ ID NO: 12); ggag (SEQ ID NO: 13); and aaauggga (SEQ ID NO: 14).

Further, iRNA relatives (e.g., iRNA r1, iRNA r2, and iRNA r3) may comprise conserved polynucleotide sequence(s) (bolded and underlined above): ucgacg (SEQ ID NO: 15); and/or cuccga (SEQ ID NO: 16). The iRNA molecule may comprise both conserved polynucleotide sequence(s): ucgacg (SEQ ID NO: 15); and cuccga (SEQ ID NO: 16). In some embodiments, the iRNA molecule are highly related to CYVaV (or to iRNA r1, iRNA r2, or iRNA r3), and comprise a polynucleotide sequence having 70% or more identity for the recoding site for synthesis of RdRp thereof, e.g., 75% or 85% or 90% or 95% or 98% identify of the RdRp of CYVaV (or of iRNA r1, iRNA r2, or iRNA r3).

Thus, in accordance with disclosed embodiments, an RNA vector (e.g., derived from an iRNA molecule) comprises a frameshift ribosome recoding site for synthesis of the RNA-dependent RNA polymerase (RdRp). In addition, the RNA vector may include a 3' end comprising a polynucleotide sequence that terminates with three cytidylates ( . . . CCC). The penultimate 3' end hairpin may also contains three guanylates in the terminal loop ( . . . GGG . . . ). Further, the 3' CITE includes an extended hairpin or portion thereof that binds to Eukaryotic translation initiation factor 4 G (eIF4G) and/or Eukaryotic initiation factor 4F (eIF4F).

In certain embodiments, an RNA vector comprises a 3'CITE comprising conserved sequences auagcacug (SEQ ID NO: 4) and gauuuguga (SEQ ID NO: 5). The RNA vector may also comprise one or more of the following polynucleotide sequences (conserved sequences of identified iRNA molecules): cguuc (SEQ ID NO: 10) and gaacg (SEQ ID NO: 11); and/or gguuca (SEQ ID NO: 12) and ggag (SEQ ID NO: 13); and/or aaauggga (SEQ ID NO: 14). Alternatively, or in addition, the RNA vector may comprise one or both of the following polynucleotide sequences (conserved sequences of identified iRNA molecules): ucgacg (SEQ ID NO: 15) and cuccga (SEQ ID NO: 16).

Identified iRNA relatives all have inserts in the 3'UTR and other nucleotide changes that result in the generation of an ORF that encodes a protein (p21.2) of unknown function. One differentiating characteristic of iRNAs such as CYVaV from any plant virus (FIG. 2) is that iRNAs do not encode any movement protein(s), which is characteristic of all known plant viruses including umbraviruses. Nor do iRNAs such as CYVaV require any helper virus for systemic movement through plants, including tested citrus and *Nicotiana benthamiana* (a laboratory model plant).

In contrast, PEMV2, as with all umbraviruses, encodes for two movement proteins: p26 (long-distance movement) and p27 (cell-to-cell movement) (FIG. 3, Panel A). p26 is also a stabilization protein that protects the genome from nonsense mediated decay, and is required for accumulation at detectable levels of PEMV2 in single cell protoplasts (Gao, F. and Simon, A. E. (2017), *Differential use of 3' CITEs by the subgenomic RNA of Pea enation mosaic virus 2*, Virology 510:194-204). Umbraviruses are unusual viruses as they do not encode a coat protein or RNA silencing suppressor, but rather rely on a helper virus for these functions. For PEMV2, the helper virus is the enamovirus PEMV1.

The polynucleotide sequence of PEMV2 is presented below (SEQ ID NO:23):

```
ggguauuuau agagaucagu augaacugug ucgcuaggau caagcggugg uucacaccug acuucacccc uggcgagggc gugaagucua gagcucaacu ggaaagagag cuggauccca ccugggcgcu ucucgugugc caagaacgag cgcgucguga ugcugacagu auugcuaaug agugguacga gggcagcaug gagugcaacc uccuuauccc ucggcccaca accgaggaug uauuuggccc cuccaucgcc ccugagccug uggcucuagu ggaggaaacu acccguuccc gcgcgccgug cguggauguc ccugccgagg aguccuguaa gucagcggag auugauccug uugaucucgc caaguucgac ucccuccauc gucgccuguu ggcugaagcc aacccuugca gggaaauggu ucuguggguug ccuccuggcc uaccagcaga gcgcgacguc cugcccaggg cacgugggu gauaaugauc cccgaaguc cugcccucugc acauaccuug uccgugaagg uuauggaggc ugugcgguug gcacaggaag ucuuggcauc ccuugccaag agggccuuag agaaaagguc uacaccaacc cuuaccgccc aggcccagcc agaggcuacc cugucggggu gcgacuaccc guaucaggag acuggagcag cagccgcgug gauaacgccu ggcugcauug ccauggagcu cagagccaaa uuuggcgucu gcaaacgcac ccccgcaaac uuagagaugg ggagucgcgu cgcccgcgag cuccugcggg auaacugugu cacuugcagg gagaccacgu gguacaccag ugccauugcu guggaccugu gguugacccc gaccgucguc gaccuggccu guggccggcg agcggcggau uuuugguagg ggcugugcug ccucggcugg gggaagacac
```

-continued

```
cagugugcgg uuugacaacc ugcaccccag caucgaggua aucaaggcgg cuaggccccg cccaacccag aggaugucgu uccaaaucga cguugugcgu ccucuuggag auuuugggugu gcacaacaac ucccuuguua accuagccag gggaauuaau gaaagggugu ucuacacgga caaugcuagg acagaacccc uccagccuaa gguucccuuc cccucaucac gggagcuaaa aaccuucaga gucacccuu ggaccaugga uaggguugug gagaguuaca cagggucca gcgcacucgc uaugcuaacg cgcgggacag cauauuaucc aacccucuga gucccaaaga ugcgcggguc aagacguuug ucaaagcuga aaagauaaau uucacagcca aaccugaccc cgccccucgu gugauacagc cuagggaucc acgauucaac auuguccugg cuaaauacau caagccuuug gagccaaugu uguacaaagc acuggggaaa cuuuacaagu accccgcagu ugcuaagggg uuuaacgcgg uugagacggg ggagaucauc gccggcaagu ggcggugcuu caaagauccu gucgucgugg gauuagacgc uucccgauuu gaucagcaug uaucugucga ggcguugcag uucacccacg cgguguacag aggguucauc aagucacggg aguuuaacaa ccuccuacag augauguaca ccaaccgugg ccuagggucc gcuaaggacg gauucguccg uuacaagguu aaagguagac gcaugagcgg ugacauggac accuccuugg gcaacugugu gcucauggug uugcucacca ggaaccuuug caagguucua ggcaucccgc acgagcucuu caacaauggu gaugauugca ucgucuuuuu cgaucguugc cacuuggaga aguucaacaa ugcugucaag acuuauuuug cggaccuagg guuuaagaug aagguggaac cgccgguuga cguguuggag aaaauagagu ucugccaaac gcagccuauc uaugacgggg agaaguggcg caccgugcgu ugcaucucga guaucggaaa agauugcuca uccguuauua guugggacca auuggagggg uggguggaaug ccaucgccca gaguggucug gcuguguugug gcggaaugcc gauauacacg ucguucuacc gguggcuagc acgggccggu aagaguggga ccaaguguca gucacacccc uuguggaaaa acgagggguu gaauugguac aggaugggga uggaccuuuc ucaugagguu aauguuaccc cucaggcgcg ccugucuuuc uucgcggguu uugguauuuc ccccccgaug caggucgcca uugaggcgcu guaugacaag cugccuccac cgucccccca ccaugguccu ccgguuaagg cuguaacaca gcgaguguuc accaauuauu ucacgccgga aagcgccugu guuagcauga gcacgaauga agacaacaaa ucugacuuug cuguuuacgg cccugugccu acagugaugu cucuuugugc ucaguguuag gcucuuaaau uuuagcgaug gcgugacacg guuacacccu
```

-continued

```
gaauugacag gguacagauc aagggaagcc ggggagucac caacccaccc ugaaucgaca gggcaaaaag ggaagccggg caccgcccac guggaaucga ccacgucacc uuuucgcguc gacuaugccg ucaacacccu uucggcccgc cagccuagga caauggcggu agggaaauau augacgauaa ucauuaaugu caauaacgac gagcgcaagc aaccagaagg agcuacuggc agcucuguac ggcgagguga caauaaaaga acucgaggaa acaaaccucg gagucaucac cccgguucgc gcgaacgaaa agguuacaau caccccucuc cuacccccaa aaacucaaag cagggucagc uccguacuga agcgguucag gagcacccga aacacggggg gacugcuuuc cguagagaaa guggugguag uguucacccc ucacaucccc gacgacgugc uaggagaggu ggagauaugg cuccacgaca gcauccuccc ccaccucggg agcgucggac caagacugaa acucaagcug agcgaagggc ccaagcucuu agcguucuac ccacccuacu cgauugcauu gggggacucg aucucgggcc agccgagguc cuucuccauu gucaccgagc uguucgaagg caacuucgca ccggggugca gcccauucag ccuguuccuc auguggaguc cacgcaucga agcagugacc cacaacuacu ugagucgucc accacgugcu cugccaauuu gcagaacgau ggugcgggac gcguuaucgg agguggcauc ccaacagcaa uaccugaagg gagcgauguc gaacaggnau gccaugccuc ucacuacggg ugauggccag cauagagcca ugaagggggc ucccagugcc cuuccaccaa cgggggugug uacccaggcu ucuaagugag gcuucgcuuc ccgccggaag accgcggcgg uucuguuccu cccacaggag uacggcaaca acccaccuug ggaaaguggg gaccccagca cuaacuccuu uaacuaggcg ggcguguugg uuacaguagg aggggacagu gcgcaucgaa acugagcccc accacaacuc ucauccacgg ggugguuggg acgcaggugu cggagggauc gccagcccuc aggauaguga gcucccgcag agggauaagc uaucucccug cgacguagug guagaacacg ugggauaggg gaugaccuug ucgaccgguu aucgguccuc ugcuccuucg agcuggcaag gcgcucacag guucuacacu gcuacuaaag uugguggugg augucucgcc caaaaagauc acaaacgcgc gggacaaggu cccuuccacc uucgccgggu aaggcuagag ucagcgcugc augacuauaa cuugcggccg auccaguugc acgacuggug gucccccuca gugucucggu ugucugccga guggggcggug gucggauucc accacacccu gccacgaggu gcguggagac uuggccaguc uaggcucguc guaauuaguu gcagcgacgu uaaucaaccc guccgggcau auaauaggac
```

-continued

```
cgguugugcu ucuuccuccc uucuuagcca ggugguuacc ucccuggcgc cc
```

The polynucleotide sequence of the intergenic plus region of PEMV2 (bolded and underlined above) is presented below (SEQ ID NO:24):

```
    guuagcauga gcacgaauga agacaacaaa ucugacuuug cuguuuacgg cccugugccu acagugaugu cucuuugugc ucaguguuag gcucuuaaau uuuagcgaug gcgugacacg
    guuacacccu gaauugacag gguacagauc aagggaagcc ggggagucac caacccaccc ugaaucgaca gggcaaaaag ggaagccggg caccgcccac guggaaucga ccacgucacc
    uuuucgcguc gacuaugccg ucaacacccu uucggcccgc cagccuagga caauggcggu agggaaauau aug
```

The polynucleotide sequences of recoding frameshift sites of PEMV2 (bases 881 to 1019; see also FIG. 10) is presented
below (SEQ ID NO: 25):

```
gaccgucgucgaccuggccuguggccggcgagcggcggauuuuugguaggg 30  gcugugcugccucggcuggggggaagacaccagugugcgguuugacaaccug caccccagcaucgagguaaucaaggcgggcuaggcccc
```

Figure 5:
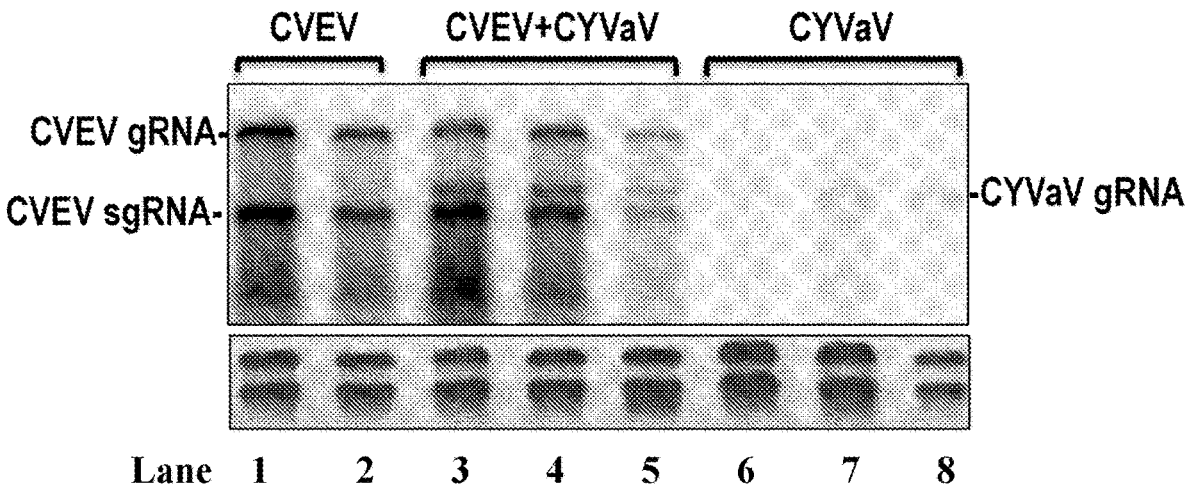
FIG. 5 shows RNA levels from agro-infiltrated leaves of *Nicotiana benthamiana*. CVEV (lanes 1-2), CVEV+CYVaV (lanes 3-5) and CYVaV (lanes 5-8) in leaves of *Nicotiana benthamiana*. Accumulation of CYVaV increased substantially in the presence of putative helper virus CVEV. Plus-strands are shown above. rRNA loading controls are shown below. p14 silencing suppressor was co-infiltrated in all leaves.
Figure 6:
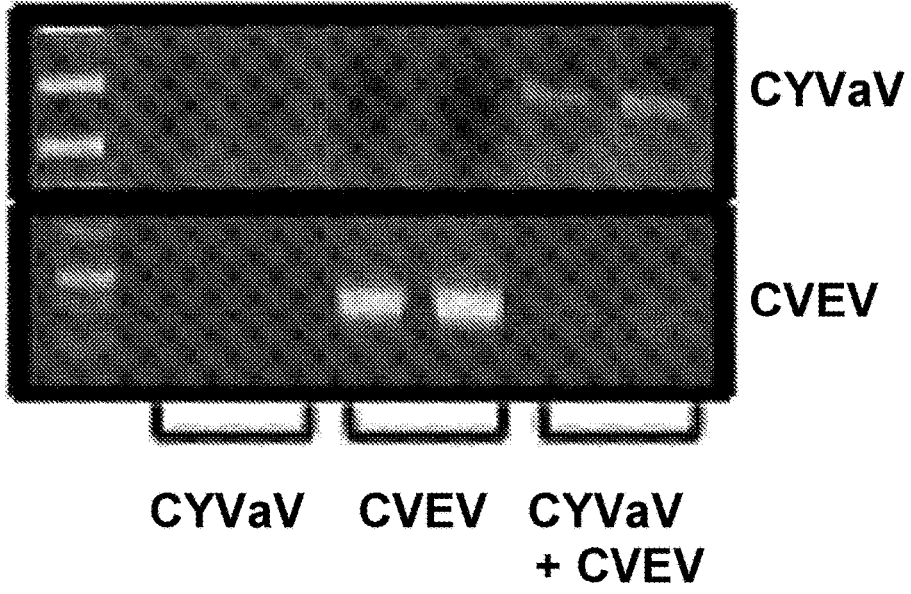
FIG. 6 shows RNA levels from another experiment with agroinfiltrated leaves of *Nicotiana benthamiana*. CYVaV or CVEV or CYVaV+CVEV agroinfiltrated into leaves of *N. benthamiana*. CYVaV was encapsidated in virions of CVEV, and virions were isolated one week later and the encapsidated RNAs subjected to PCR analysis.
Figure 7:
FIG. 7 shows yellowing symptoms of CYVaV (Panel A) and CYVaV+CVEV (Panel B), which are limited to citron (pictured), lemon, and lime.
Figure 7:
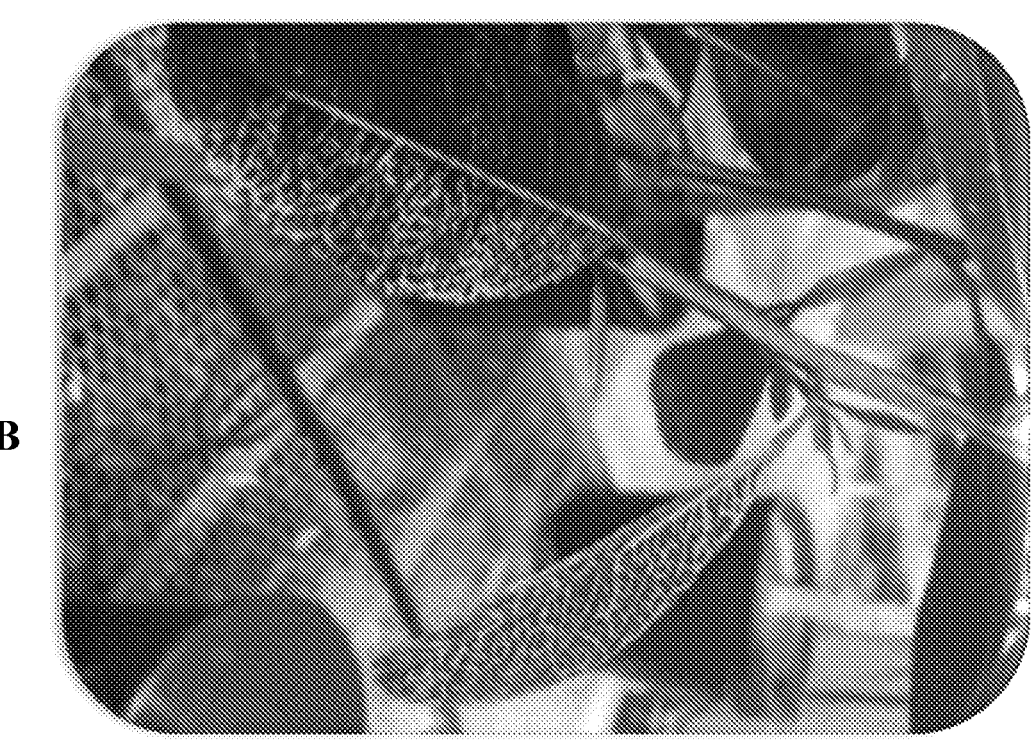

CYVaV unexpectedly replicates very efficiently in *Arabidopsis thaliana* protoplasts despite not encoding p26 (or any other movement protein), which is required for accumulation of PEMV2 because of its ability to also counter NMD. Indeed, CYVaV was unusually stable, much more stable than most traditional viruses. CYVaV also produced an astonishingly high level of p81 in wheat germ extracts, at least 50-fold more than the p94 orthologue from PEMV2 (FIG. 3, Panel C). When CYVaV was agro-infiltrated into leaves of *Nicotiana benthamiana*, it replicated in the infiltrated tissue but accumulation was relatively weak (FIG. 3, Panel B, top; FIG. 5, lanes 6-8). No replication was achieved with manual inoculation. However, when CYVaV was co-infiltrated with the enamovirus Citrus vein enation virus (CVEV), accumulation improved substantially in these cells (FIG. 5, lanes 3-5; see also FIG. 6). However, yellowing symptoms of CYVaV+CVEV (FIG. 7, Panel B) were more vibrant as compared to symptoms exhibited by CYVaV alone (FIG. 7, Panel A).

CYVaV had no synergistic effect with any other combination of citrus virus tested. Additional studies showed that CVEV may be utilized as a helper virus for CYVaV in order to allow for transmission from tree to tree. CVEV was likely responsible for the presence of CYVaV in the original limequat trees; however, CVEV is known to be very heat sensitive and thus was likely lost from the limequat trees during a hot summer.
CYVaV moved sporadically into upper, uninoculated leaves and accumulated at extremely high levels, sometimes visible by ethidium staining on gels. Symptoms that began in the ninth leaf of the major bolt comprised stunting, leaf curling, and deformation of floral tissue. Leaves in axillary stems also began showing similar symptoms around the same time. This astonishing result demonstrated that CYVaV moves systemically in the absence of any encoded movement protein(s), which is not possible by traditional plant viruses. Experiments showed that CYVaV moves systemically in *N. benthamiana* and is strictly confined to the phloem, replicating only in companion cells and phloem parenchyma cells. In citrus, CYVaV is 100% graft-transmissible, but difficult to transmit in other forms.

Fluorescence in situ hybridization (FISH) of symptomatic leaf tissue and roots confirmed that CYVaV is confined to phloem parenchyma cells, companion cells and sieve elements (FIG. 8, Panels A-G), which is characteristic of a phloem-limited virus. CYVaV levels were extremely high in the petioles of symptomatic tissue and sometimes visible in ethidium-stained gels of total RNA. Although symptoms are more severe in *N. benthamiana*, CYVaV has been found to be virtually symptomless in all varieties of citrus tested. Indeed, the most severe symptom was found on citron, the indicator tree for citrus viruses, and consisted of very minor gold flecking on leaves scattered throughout the tree.

Phloem-limited movement of CYVaV explains why it is readily graft-transmissible, but not transmissible by any other means. CYVaV lacks any encoded movement protein(s) as noted above. Instead, CYVaV utilizes the host plant's endogenous movement protein(s) and pathway for transiting between companion cells, phloem parenchyma cells, and sieve elements. In addition, since host range is believed to involve compatible interactions between viral movement proteins and host plasmodesmata-associated proteins, it is believed that CYVaV is capable of transiting through the phloem of numerous other woody and non-woody host plants using such host's endogenous movement protein(s). As such, CYVaV provides an exceptional model system for examining RNA movement (e.g., in *N. benthamiana* and/or citrus) and for use as a vector for numerous applications. Experiments confirmed that CYVaV moves systemically in a host plant and is limited to the phloem, and is readily graft-transmissible but not transmissible in other forms.

Citrus trees have a complex reproductive biology due to apomixis and sexual incompatibility between varieties. Coupled with a long juvenile period that can exceed six years, genetic improvement by traditional breeding methods is complex and time consuming. The present disclosure overcomes such problems by providing an iRNA-based (e.g., CYVaV-based) vector engineered to include therapeutic inserts using RNAi and CRISPR/Cas9. iRNAs such as CYVaV are unique among infectious agents given they encodes a polymerase yet move like a viroid using host movement proteins, and thus are capable of transiting through plants other than citrus. Thus, in addition to citrus, the iRNA-based vectors of the present disclosure may be developed for other woody plants (e.g., trees and legumes), and in particular olive trees and grapevines.

In accordance with disclosed embodiments, CYVaV is utilized in the development of a vector for delivery of small RNAs and proteins into citrus seedlings and *N. benthamiana*. The procedure utilized for CYVaV vector development was similar to that utilized by the present inventors for engineering betacarmovirus TCV to produce small RNAs (see Aguado, L. C. et al. (2017), *RNase III nucleases from diverse kingdoms serve as antiviral effectors*, Nature 547: 114-117). Exemplary and advantageous sites for adding one, two, three, or more small RNA inserts designed to be excised by RNase III-type exonucleases were identified. A small reporter RNA was expressed directly from the genome that targets phytoene desaturase, which turns the targeted tissue white.

In accordance with disclosed embodiments, vectors disclosed herein may include small RNAs with various functionality including: small RNAs that target an essential fungal mRNA; small RNAs that target an insect vector(s) for death or sterility; and small RNAs that target CVEV (as this virus together with CYVaV cause enhanced yellow-vein symptoms). In addition, the disclosed vectors may include other small RNAs and/or therapeutic agents known in the art. Thus, a phloem-restricted iRNA-based vector may be engineered to produce small RNAs that have anti-fungal and/or anti-insect and/or anti-viral properties, which provides for a superior treatment and management strategy compared to current methodologies.

CYVaV vectors may be applied manually to infected or uninfected trees by cutting into the phloem and depositing the vector either as RNA, or by agroinfiltration, or after encapsidation in the coat protein of CVEV, following citrus inoculation procedures well known to those of skill in the art, e.g. such as procedures developed and used routinely under the Citrus Clonal Protection Program (CCPP). Such procedures are routine for inoculation of CTV and other graft-transmissible pathogens of citrus. Since CYVaV does not encode a capsid protein, no virions are made and thus no natural tree-to-tree transmission of CYVaV is possible. When CYVaV is encapsidated in CVEV coat protein, no other component of CVEV is present.

As noted above, CYVaV has only two ORFs: a 5' proximal ORF that encodes replication-required protein p21; and a frame-shifting, ribosome recoding element that allows ribosomes to continue translation, extending p21 to produce p81, the RNA-dependent RNA polymerase. The organization of these two ORFs is similar to the organization of similar ORFs in viruses in the Tombusviridae and Luteoviridae. However, all viruses in these families, and indeed in all known plant RNA viruses, encode movement proteins or are associated with a secondary virus that encodes a movement protein(s). The ability to encode movement proteins, or associate with a second virus that encodes a movement protein(s), had long been considered a requirement for movement from cell-to-cell and also for transiting through the phloem to establish a systemic infection. As such, the use of iRNAs as vectors had not been proposed, and indeed iRNA molecules were previously considered unsuitable for use as an independent vector due to the lack of any encoded movement protein and belief that they were not independently mobile.

As such, the capacity for independent systemic movement of iRNAs throughout a plant's phloem despite not coding for or depending on any exogenous movement protein(s) is thus quite surprising. The CYVaV-based vectors of the present disclosure unambiguously and repeatedly demonstrated (via fluorescence in situ hybridization and other techniques) systemic movement without the aid of any helper virus. Young, un-infiltrated (systemic) tissue displayed highly visible symptoms on *N. benthamiana*, including leaf galls and root galls. The disclosed vectors utilize endogenous host movement protein(s) for mobility. In this regard, host phloem protein(s) (25 kDa phloem protein 2 (PP2) and/or 26 kDa *Cucumis sativus* phloem protein 2-like) known to traffic host RNAs into sieve elements (see Balachandran, S. et al. (1997), *Phloem sap proteins from Cucurbita maxima and Ricinus communis have the capacity to traffic cell to cell through plasmodesmata*, PNAS 94(25):14150-14155; Gomez, G. and Pallas, V. (2004), *A long-distance translocatable phloem protein from cucumber forms a ribonucleo-protein complex in vivo with Hop stunt viroid RNA*, J Virol 78(18):10104-10110) were likely shown to interact with CYVaV using Northwestern blots. Thus, since known plant viruses encode (or are dependent on) a movement protein, iRNAs are quite different structurally and functionally from traditional plant viruses.

In addition to CYVaV, other RNAs of similar size and that encode a polymerase may be utilized in the develop of similarly structured iRNA-based vectors (see, e.g., Chin, L. S. et al. (1993). *The beet western yellows virus ST9-associated RNA shares structural and nucleotide sequence homology with Tombusviruses.* Virology 192(2):473-482; Passmore, B. K. et al. (1993). *Beet western yellows virus-associated RNA: an independently replicating RNA that stimulates virus accumulation.* PNAS 90(31):10168-10172). As noted above, other iRNA relatives (e.g., iRNA r1, iRNA r2, and iRNA r3, identified in Opuntia, Fig trees, and Ethiopian corn, respectively) and that encode proteins p21 and p81 (FIG. 4) may be utilized for vector development.

Although CYVaV is present in the GenBank database (GenBank: JX101610), iRNAs do not belong to any known classification of virus given they lack cistrons that encode movement proteins. Nor are iRNAs dependent on a helper virus for systemic movement within a host. Moreover, iRNAs lack cistrons that encode coat proteins. iRNAs are also dissimilar to viroids, although both are capable of systemic movement in the absence of encoded movement proteins. Viroids are circular single stranded RNAs that have no coding capacity and replicate in the nucleus or chloroplast using a host DNA-dependent RNA polymerase. The vast majority of the tiny viroid genome, typically including about 300 to 400 nucleotides (nt), is needed for the viroid's unusual existence. In addition, viroids do not code for any proteins, which makes them unsuitable for use as vectors. In contrast, iRNAs code for their own RNA-dependent RNA polymerase (RdRp).

iRNAs may be categorized in two classes: a first class is characterized by a frameshift requirement to generate the RdRp and RNA structures proximal to the 3' end that resemble those of umbraviruses. A second class is characterized by a readthrough requirement to generate the RdRp and 3' RNA structures that resemble those of Tombusviruses. CYVaV is a member of the first class with properties similar to umbraviruses including a frameshifting recoding site and similar structures at the 3' end, and similar sequences at the 5' end. iRNA members of the second class have always been discovered in association with a helper virus.

iRNAs provide a number of benefits as compared to conventional viral vectors. For example, iRNAs are relatively small, making them easier to structurally and functionally map and genetically manipulate. In contrast, viruses such as CTV are 8-fold larger, making them more cumbersome to use as a vector. iRNAs can replicate and accumulate to unexpectedly high levels (e.g., visible by ethidium staining on gels and 4% of reads by RNAseq), which is critical for the vector's ability to deliver a sufficient amount of therapeutic agent(s) into the target plant. In addition, iRNAs are much more stable than many viruses despite not encoding a coat protein or silencing suppressor (FIG. 13), which allows for a long lifespan in the host plant and thus provides benefit over an extended period.

iRNAs are also limited to the host's phloem, which is especially useful for targeting pathogens that either reside in, or whose carriers feed from, or whose symptoms accumulate in, the phloem since the payload will be targeted to where it is most needed. By moving independent of movement proteins (whose interactions with specific host proteins is the primary factor for determining host range), iRNAs are able to transit within a broader range of hosts, thereby increasing the applicability of a single vector platform. Given the lack of coat protein expression and the dispensability of a helper virus for systemic plant infection, iRNAs cannot be vectored from plant-to-plant and instead must be introduced directly into the phloem via grafting. The lack of a coat protein prevents formation of infectious particles and thus unintended reversion to wild type infectious agents into the environment. This is particularly beneficial for streamlining regulatory approval as regulators are often concerned with the possible uncontrolled transmission of introduced biological agents.

iRNAs are also virtually benign to their hosts, unlike viruses like CTV whose isolates can be highly pathogenic. Using a common virus as a vector, such as CTV, runs the risk of superinfection exclusion, where trees previously infected and/or exposed to that virus are not able to be additionally infected by the same virus acting as the vector (e.g., most citrus trees in the USA are infected with CTV). Thus, avoiding superinfection exclusion, at a minimum, requires additional steps to the process that makes it more expensive and cumbersome.

The present disclosure also provides for novel therapeutic, prophylactic, or trait enhancing inserts that are engineered into the iRNA vector. A variety of inserts are provided, including inserts that target a particular pathogen, an insect vector, or a manifestation of the disease(s). Alternatively, or in addition, inserts are provided that strengthen or improve plant health and/or enhance desired characteristics of the plant.

The disclosed infectious agents are capable of accumulation and systemic movement throughout the host plant, and can thus deliver therapies throughout a host over a substantial time period. Characteristics of the disclosed agents are therefore highly beneficial for treating numerous specific diseases. Using an infectious agent composed of either RNA or DNA has an additional advantage of being able to code for therapeutic proteins or peptides that would be expressed within infected cells and/or by engineering the infectious agent to contain a specific sequence or cleavable portion of its genetic material to serve as an RNA-based therapeutic agent.

Products with antimicrobial properties against plant pathogens can take a number of formats and are produced through ribosomal (defensins and small bacteriocins) or non-ribosomal synthesis (peptaibols, cyclopeptides and pseudopeptides). The best known are over 900 cationic antimicrobial peptides (CAPs), such as lactoferrin or defensin, which are generally less than 50 amino acids and whose antimicrobial properties are well known in the art. CAPs are non-specific agents that target cell walls generally, with reported effects against bacteria and fungi. CTV engineered with an insert designed to express defensin has received approval for release by the USDA in Florida, but its widespread efficacy is unknown. Moreover, the isolate of CTV used for the vector makes it unsuitable for trees growing in some regions (e.g., California).

RNA therapies that target viral pathogens are also in widespread development in plants. These therapies use non-coding small interfering RNAs (siRNAs), which are generated from the genome of the plant, and thus include genetic modification of the host. In addition to negative viewpoints of some growers and consumers to genetic modification of citrus trees, the length of time to generate genetically modified trees is measured in decades and may ultimately not have the same attributes (texture/color/taste) as varieties developed over decades, and thus is not a solution to current, time sensitive agricultural diseases, in addition to being very expensive to develop and potentially impacting the quality of the fruit.

Recently, highly targeted anti-bacterial enzymes have been developed for use in animals and humans as a replacement for current antibiotics. These enzymes are engineered from bacteriophage lysis proteins and are known as enzybiotics. As with the parental bacteriophage proteins, enzybiotics can lyse bacterial cell walls on contact, but are designed to be used external to both gram positive and gram negative bacteria. Enzybiotics are engineered to lyse only targeted bacterium, leaving other members of the microbiome unaffected. In some implementations, an iRNA vector is provided that includes a non-coding RNA insert that can be translated into an anti-bacterial protein like an enzybiotic.

In some implementations, an iRNA vector is provided that includes an RNA insert that interferes with the functionality of the insect vector at issue. Insects have an RNA silencing system similar to plants; small RNAs ingested by insects are taken up into cells and target critical mRNAs for degradation or blockage of translation within the insect. In some embodiments, a targeted insert is provided that is capable of silencing a critical reproductive function of the insect vector, resulting in sterilization of the insect. Of particular relevance are phloem-feeding insects that transmit phloem-limited pathogens, where a non-coding RNA insert into a phloem-limited vector is readily taken up by feeding insects.

In some implementations, an iRNA vector is provided that includes a non-coding RNA insert that targets a plant response to a pathogen. In some cases, bacteria inserted by an insect vector does not directly damage the tree. However, the host tree produces excessive callose in their phloem in order to isolate the bacteria, which can ultimately restrict the flow of photoassimilates and kill the tree. Thus, the RNA insert silences and/or depresses such callose production.

Additional characteristics and features of the present disclosure will be further understood through reference to the following additional examples and discussion, which are provided by way of further illustration and are not intended to be limiting of the present disclosure.

Figure 9:
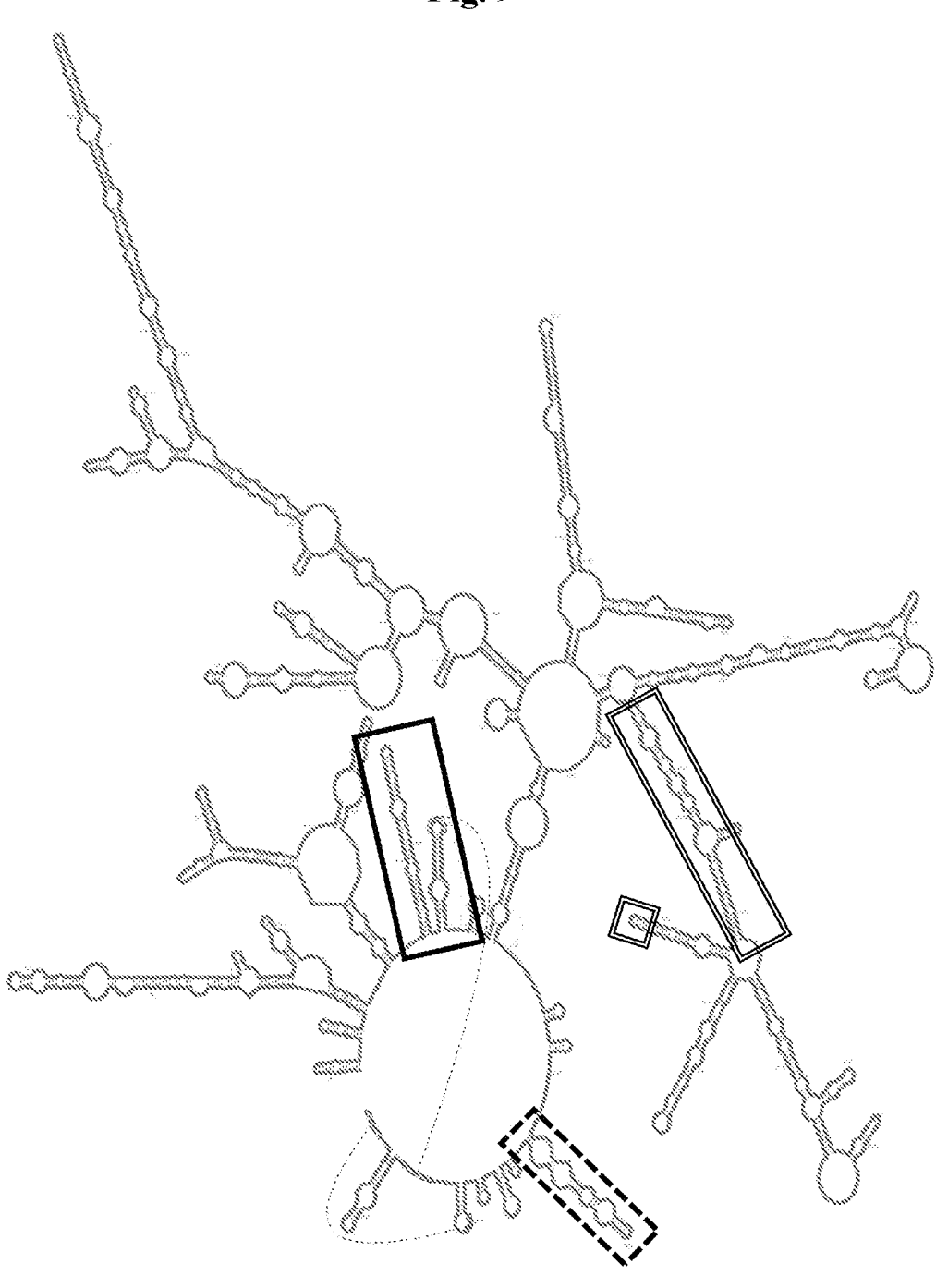
FIG. 9 illustrates schematically the full-length secondary structure of CYVaV as determined by SHAPE structure probing and phylogenetic comparisons with the CYVaV relatives in Opuntia, fig and corn. The recoding frameshift site (see FIG. 10) is identified by boxed single solid line region, and the ISS-like (I-shaped structure) 3'CITE (see FIG. 11) is identified by boxed dashed line region. For example, a region for accommodating inserted hairpin(s) is shown by boxed double line region.
Figure 11:
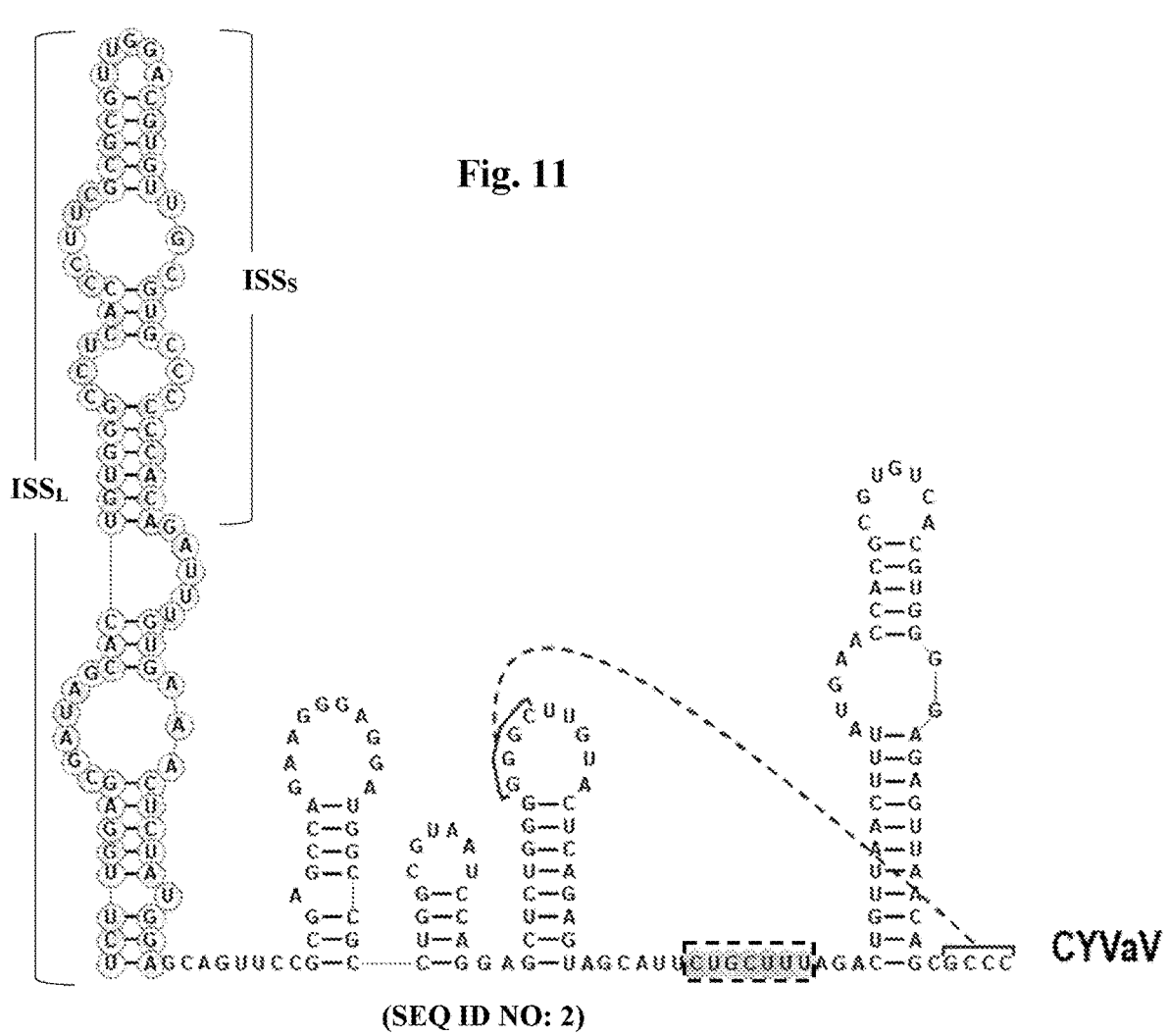
FIG. 11 illustrates schematically the ISS-like 3' Cap Independent Translation Enhancer (3'CITE) of CYVaV. The structure of the 3' end of CYVaV is shown. The 3'CITE is illustrated at the left-most portion shown and with bases circled. Sequence identified by boxed solid line engages in the long-distance RNA:RNA interaction with the recoding site.
Figure 12:
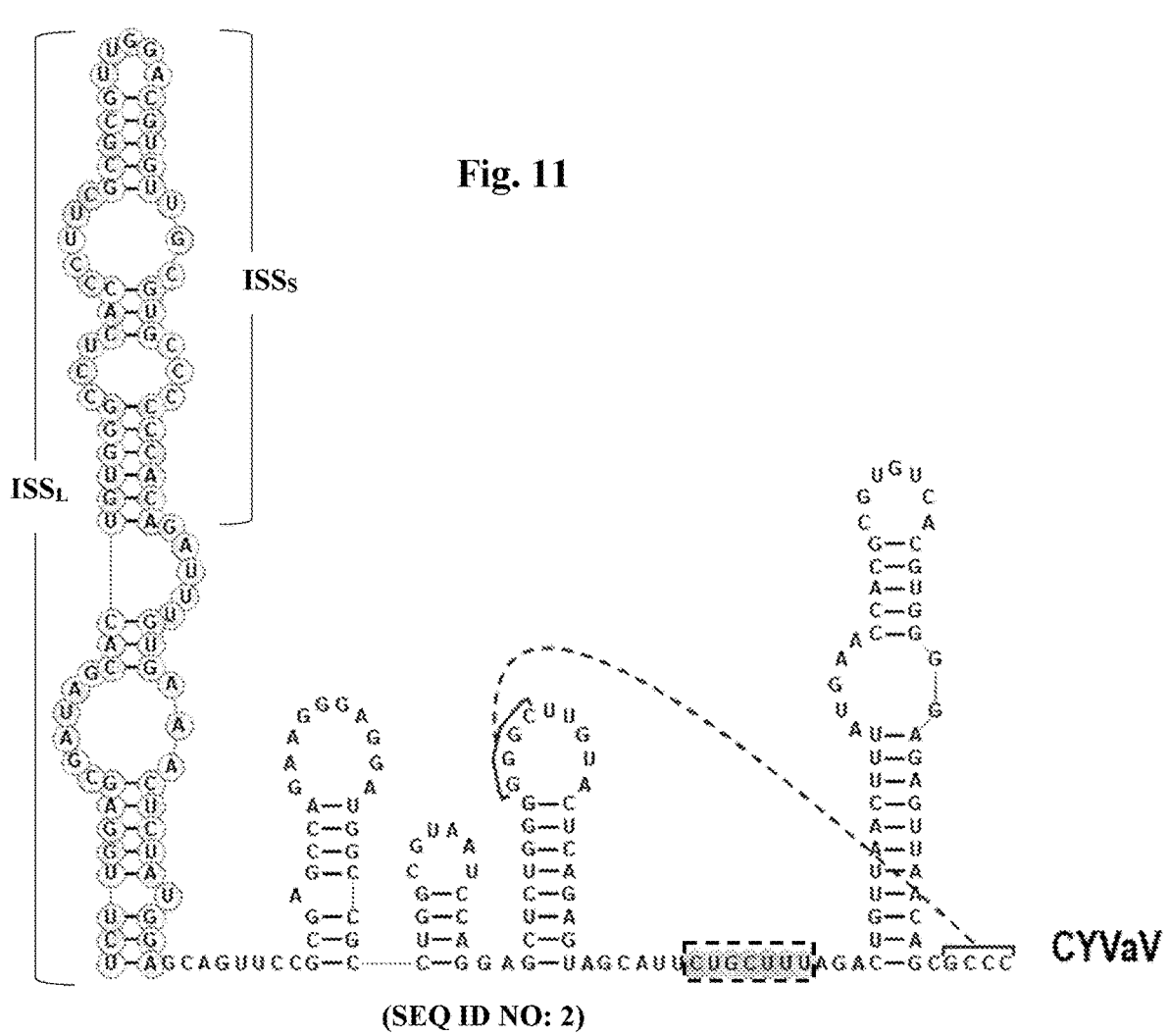
FIG. 12 illustrates results from a trans-inhibition assay. Full-length CYVaV was translated in vitro in the presence of 10-fold molar excess of a truncated version of the ISS ($ISS_S$) or full-sized ISS ($ISS_L$).

CYVaV Structure. Full length structure of CYVaV was determined by SHAPE structure probing and phylogenetic comparisons with the CYVaV relatives in Opuntia, Fig and Corn (FIG. 9). The recoding site (see FIG. 10) and the ISS-like (I-shaped structure) 3'CITE (see FIG. 11) are identified, along with a region for accommodating an insert is, for example, shown by boxed double line region and discussed in further detail with regard to exemplary locations for inserts.

The genome organization of CYVaV exhibits some similarities to other RNA molecules, particular PEMV2 (FIG. 3, Panel A). However, umbravirus PEMV2 also possesses ORFs encoding for proteins p26 and p27 involved in movement. Levels of CYVaV plus (+) strands in infiltrated N. benthamiana leaves and systemic leaves are shown in FIG. 3, Panel B. Levels of the RNA-dependent RNA polymerase (RdRp) synthesized by frameshifting in vitro in wheat germ extracts of full-length CYVaV and PEMV2 are also shown (FIG. 3, Panel C). Note the significant difference in levels of p94 from PEMV2 as compared to p81 polymerase produced by CYVaV. The frameshifting site of CYVaV is one of the strongest known in virology and believed to be responsible for its exceptionally high accumulation.

CYVaV is encapsidated in virions of CVEV. CYVaV or CVEV or CYVaV+CVEV were agroinfiltrated into leaves of N. benthamiana. CYVaV was encapsidated in virions of CVEV, and virions were isolated one week later and the encapsidated RNAs subjected to PCR analysis (see FIGS. 5 and 6). Accumulation of CYVaV increased substantially in the presence of putative helper virus CVEV. rRNA loading controls are shown below. p14 silencing suppressor was co-infiltrated in all leaves. Yellowing symptoms were slightly more severe in leaves with CYVaV+CVEV (FIG. 7, Panel B).

Figure 8:
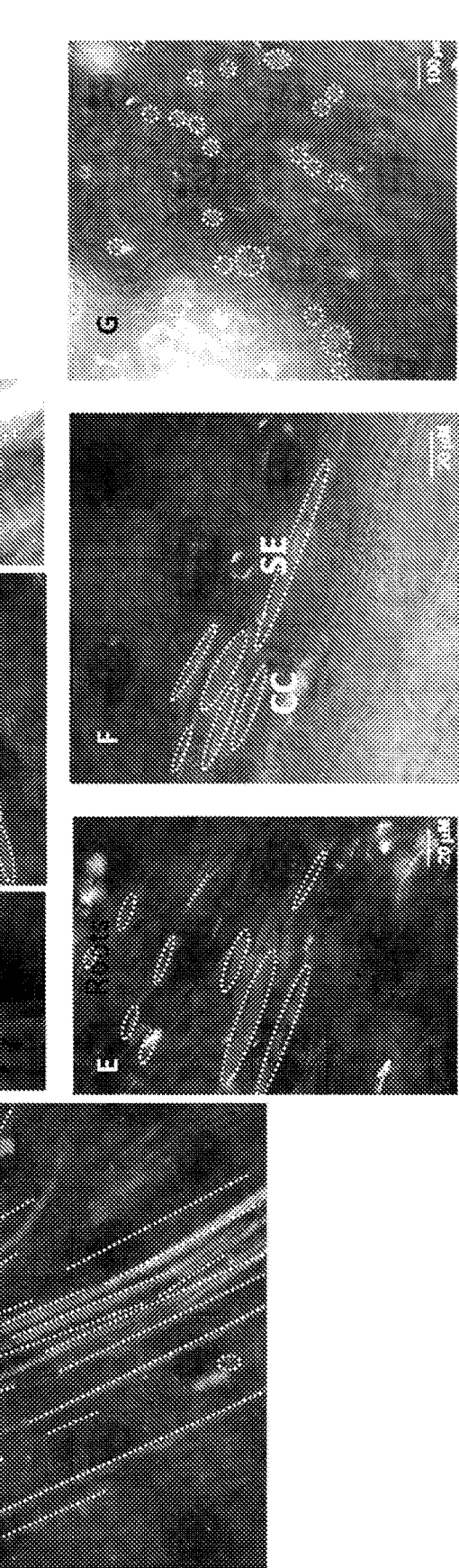
FIG. 8 shows the systemic and phloem-limited movement of CYVaV in *N. benthamiana*, wherein CYVaV is confined to the transport tissues of the plant. Fluorescence in situ hybridization (FISH) imaging detecting plus strands of CYVaV were stained pink (with areas generally shown herein with dashed white lines and circles) are shown in Panels A-G, including longitudinal and cross-sectional views of petioles (Panels A-D) and root tissue (Panels E-G). Tissue was stained with DAPI. Companion cells (CC), phloem parenchyma cells (PPC) and sieve elements (SE), and xylem (XL) are identified. Note that the iRNA is completely restricted to the SE, CC and PPC. Blue (shown herein as dark grey or black areas) is from DAPI staining of endogenous DNA. CYVaV is symptomless in virtually all tested citrus.

CYVaV is phloem-limited. Fluorescence in situ hybridization (FISH) imaging clearly detected plus strands of CYVaV, which was completely restricted to the SE, CC and PPC (FIG. 8).

Figure 13:
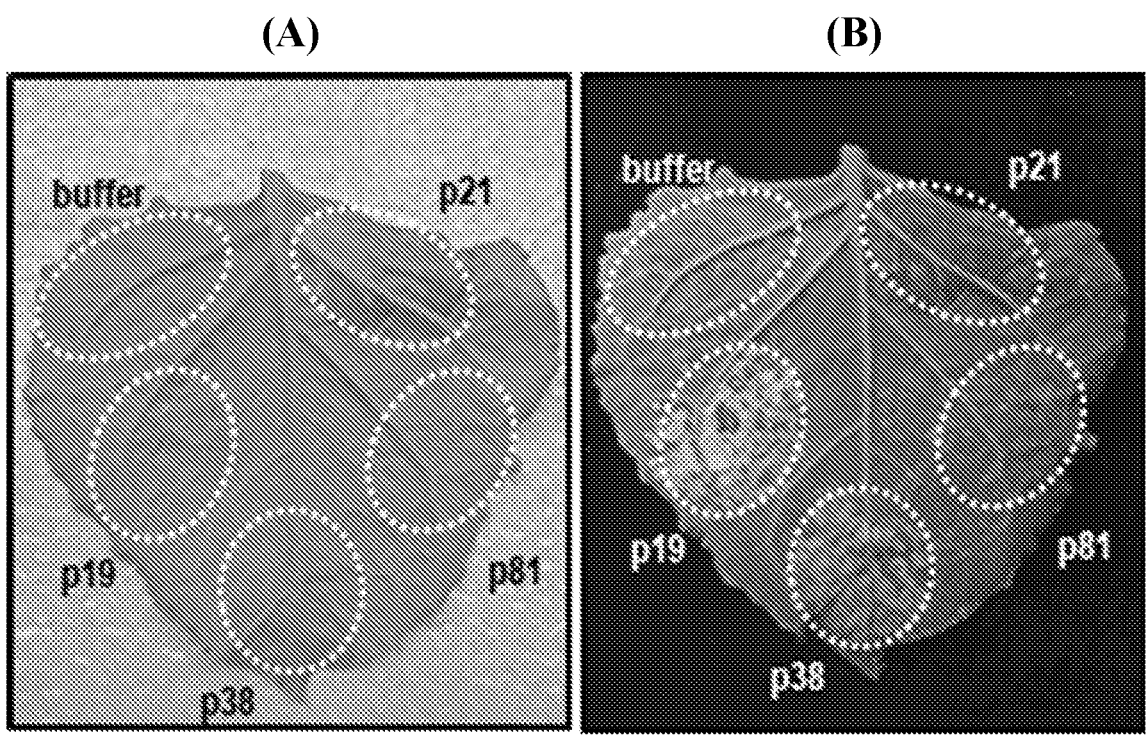
FIG. 13 demonstrates that CYVaV does not encode a silencing suppressor. Referring to Panels A and B, *N. ben-*
Figure 13:
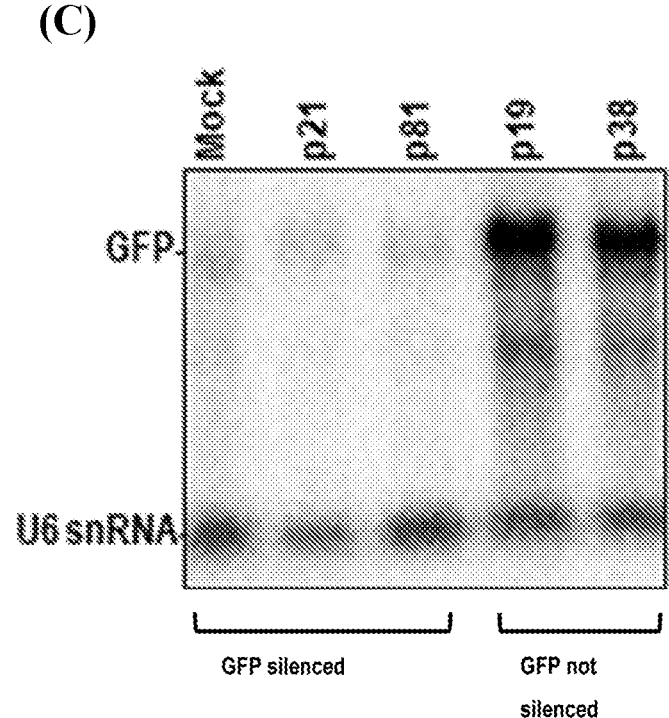

CYVaV does not encode a silencing suppressor. N. benthamiana 16C plants were agroinfiltrated with a construct expressing GFP (which is silenced in these plants) and either constructs expressing CYVaV p21 or p81, or constructs expressing known silencing suppressors p19 (from TBSV) or p38 (from TCV) (FIG. 13, Panel A). Only p19 and p38 suppress the silencing of GFP, allowing the green fluorescence to be expressed (FIG. 13, Panel B). Northern blot probed with GFP oligonucleotide showed that GFP RNA is still silenced in the presence of p21 or p81 (FIG. 13, Panel C).

Replication of CYVaV in Arabidopsis protoplasts. An infectious clone of CYVaV was generated. Wild-type RNA transcripts (CYVaV) or transcripts containing a mutation in the recoding slippery site that eliminates the synthesis of the RdRp (CYVaV-fsm), and thus doesn't replicate, were inoculated onto Arabidopsis protoplasts. RNA was extracted and a Northern blot performed 30 hours later. Note that inoculated transcripts of CYVaV-fsm were still present in the protoplasts at 30 hours (whereas in a traditional virus they would be undetectable after 4 hours).

Replication of CYVaV in N. benthamiana. Level of CYVaV accumulating in the infiltrated leaves of N. benthamiana was determined by Northern blot (FIG. 15, Panel A). Plants infiltrated with CYVaV sporadically showed systemic symptoms (FIG. 15, Panel B; see also FIG. 16). These plants accumulated high levels of CYVaV. Level of CYVaV in individual leaves of a systemically infected plant was determined (FIG. 15, Panel C). Leaves 4 and 5 were agroinfiltrated with CYVaV. Note the substantial accumulation of CYVaV in the youngest leaves.

Symptoms of N. benthamiana systemically infected with CYVaV. Leaves 4 and 5 were agroinfiltrated with CYVaV. The first sign of a systemically infected plant is a "cupped" leaf (FIG. 16), which was nearly always leaf 9. In the following few weeks, leaf galls emerged at the apical meristem and each node of the plant. Systemically infected plants also had root galls containing a substantial amount of CYVaV as evidenced by Northern plant blot.

CYVaV demonstrates an exceptional host range. Sap from a systemically-infected N. benthamiana plant was injected into the petiole of tomato (FIG. 17). One of four plants showed very strong symptoms and was positive for CYVaV by PCR. Plant shown is at 53 days post-infection with a plant of the same age.

CYVaV binds to a highly abundant protein extracted from the phloem of cucumber. Labelled full-length CYVaV binds to a prominent protein as demonstrated in the Northwestern blot (FIG. 18). Proteins were renatured after SDS gel electrophoresis. This protein is believed to be a known, highly conserved RNA binding protein containing an RRM motif known to chaperone RNAs from companion cells into sieve elements in the phloem of cucumber. No binding was seen when the proteins remained denatured after electrophoresis.

CYVaV can express an extra protein from its 3'UTR using a TEV IRES. Location of three separate inserts of nanoluciferase downstream of the Tobacco etch virus (TEV) internal ribosome entry site (IRES) were identified (FIG. 19). In vitro translation in wheat germ extracts of the three constructs was evaluated. Location of the nanoluciferase protein (Nluc) is near the bottom of the gel. Expression of nanoluciferase in protoplasts in vivo was investigated (FIG. 19, Panel C). Full-length RNA transcripts of the constructs shown in (A) were transformed into protoplasts. 18 hours later, total protein was extracted and nanoluciferase activity measured in a luminometer.

Exemplary locations for stable hairpin inserts at positions 2250, 2301 and 2319 were evaluated. The location for each of the inserts falls within an exemplary region noted above (see FIG. 9). Wheat germ extract in-vitro translation assay of T7 transcripts from CYVaV-wt, and CYVaV VIGS vectors containing different amounts of sequence at position 2250 was conducted (FIG. 20). For example, construct sfPDS60 demonstrated excellent systemic movement in plants. Wheat germ extract in-vitro translation assay of T7 transcripts from CYVaV-wt, and CYVaV VIGS vectors containing different amounts of sequence at positions 2301 and 2319 was conducted (FIG. 21). Northern blot analysis of total RNA isolated from *A. thaliana* protoplasts infected by CYVaV wt and CYVaV VIGS vectors. CYVaV-GDD and negative control was conducted (FIG. 20, Panel D). Northern blot analysis of total RNA isolated from *A. thaliana* protoplasts infected by CYVaV wt and CYVaV VIGS vectors. CYVaV-GDD and negative control. was conducted (FIG. 21, Panel D). Constructs CY2250sfPDS60, CY2301PDS60, CY2301sfPDS60, CY2319sfPDS60 (including inserts at positions 2250, 2301, 2319, respectively) all demonstrated excellent systemic movement with insertion. In addition, constructs CY2331PDS60 (including inserts at position 2331) also demonstrated the ability to move systemically throughout the host. A further construct, CY2083TAAPDS60, includes an insert at position 2083, which location is in the RdRp ORF (preceded by an inserted stop codon).

The sequences of the insertion regions (underlined below and as shown in FIG. 20, Panel G, and FIG. 21, Panel G) of the vector collected from systemic leaf is presented below:

```
                                    (SEQ ID NO: 26)
taggcctcgacacgggaaggtagctgtcccggcactgggttgcacatattc cgtgccgacgccac (SEQ ID NO: 27)
ccggcctcgacacgggaaggtagctattccgtgccgacgccgt
``` iRNA-Based Vector Platform

In one embodiment, an iRNA-based vector is provided for treating disease in the citrus industry caused by CLas bacteria (HLB). An isolate of CYVaV is utilized as a vector to target both the bacteria and the psyllid insects that deliver the bacteria into the trees. As discussed above, CYVaV is limited to the phloem where it replicates and accumulates to extremely high levels comparable to the best plant viruses. In addition, its relatively small size makes it exceptionally easy to genetically engineer. Thus, consideration of the structure and biology of CYVaV aided in the development of this novel infectious agent as a vector and model system for phloem transit.

The structure of the 3'UTR of CYVaV was determined based on SHAPE RNA structure mapping (FIG. 9). In addition, a number of replication and translation elements were identified based on biochemical assays, as well as phylogenetic conservation (with umbraviruses) of their sequence and/or structure and position (FIG. 19, Panel A). An I-shaped element was also identified that serves as a cap-independent translation enhancer (3' CITE). A series of long-distance kissing-loop interactions (double arrows) were also identified, which are believed to be involved in stabilizing the RNA and accumulation in the absence of a silencing suppressor. Based on this structure, a number of areas were identified as suitable locations for sequence insertion, which should not disturb the surrounding structure.

Certain sites have been identified for potential inserts in the 3' UTR and the RdRp ORF that can accommodate RNA hairpins, e.g., for generation of siRNAs that target feeding insects, sites that accommodate reporter ORFs and still allow for replication of an engineered CYVaV in agro-infiltrated *N. benthamiana*, and sites that trigger high level translation of reporter proteins in vitro. An engineered CYVaV incorporating the added ORF and siRNAs is introduced into a storage host tree, and then pieces thereof are usable for straight-forward introduction into field trees by grafting. Given the rarity of CYVaV (to date, it has only been identified in the four limequat trees by Weathers in the 1950s), there is little risk of superinfection exclusion.

Various insert locations were identified wherein replication or translation properties of the vector were not significantly reduced or eliminated. Insert locations adversely affecting such properties (likely due to disrupting the RNA structure or other important aspect of the CYVaV vector) were not pursued further. Four exemplary insert locations on the CYVaV-based vector were identified at positions 2250, 2301, 2319 and 2331. 50 nt hairpin inserts were successfully deployed in these locations with no disruption to translation in vitro or replication in protoplasts and CYVaV was able to move systemically in *N. benthamiana*.

Although CYVaV has no additional ORFs, both genomic (g)RNA and a subgenomic (sg)RNA of about 500 nt are detectable using probes to plus- and minus-strands. Investigation of the region that should contain an sgRNA promoter revealed an element with significant similarity to the highly conserved sgRNA promoter of umbraviruses and to a minimal but highly functional sgRNA promoter of carmovirus TCV. In addition, similar RNAs that also only express the RdRp and are related to Tombusviruses all generate a similar sized subgenomic RNA, and may simplify expression of peptides and proteins.

In order to determine where inserts are tolerated downstream of the sgRNA promoter in CYVaV, an evaluation of where critical elements exist in the 3' UTR of CYVaV was conducted, so that such elements are avoided when inserting heterologous sequences. As described about, the 3' CITE for CYVaV was identified, as well as several additional 3' proximal hairpins that are highly conserved in umbraviruses and known to be critical for replication and translation. Using deletions/point mutations, the sequence downstream of the putative sgRNA promoter and upstream of the CAS (~120 nt) was investigated for regions that do not impact either accumulation in protoplasts or systemic movement in *N. benthamiana*. A similar strategy was previously utilized by the present inventors to identify regions in the 3' UTR of TCV that can accommodate hairpins targeted by RNase III-type enzymes (Aguado, L. C. et al. (2017). *RNase III nucleases from diverse kingdoms serve as antiviral effectors*. Nature 547:114-117).

After identifying suitable regions for accommodating deletions/mutations (e.g., regions not involved in critical functions), heterologous sequences of different lengths were inserted therein to evaluate CYVaV functionality with an extended 3' UTR. Such investigation aids in determining maximal insert length to ensure that such insert will be tolerated by the CYVaV-based vector while still accumulating to robust levels and engaging in systemic movement. It is believed that the CYVaV-based vector may be able to accommodate an insert having a size of up to 2 kb. In this regard, the nearest related viruses (*papaya* umbra-like viruses, which like CYVaV, only encode a replicase-associated protein and the RdRp) are 1 to 2 kb larger, with all of the additional sequence length expanding their 3' UTRs (Quito-Avila, D. F. et al. (2015). Detection and partial genome sequence of a new umbra-like virus of *papaya* discovered in Ecuador. Eur J Plant Pathol 143:199-204). Various size sequence fragments were evaluated, beginning at 50 nt (the size of an inserted hairpin for small RNA production), up to about 600 nt (the size of an enzybiotic ORF). Initial small RNA fragments include a reporter for knock down of phytoene desaturase, which turns tissue white. The longer size fragments include nano luciferase and GFP ORFS, which may also be used as reporters for examining expression level. Inserts are made in constructs containing the wild-type (WT) sgRNA promoter and the enhanced sgRNA promoter.

Lock and Dock Sequence for stabilizing the base of inserts. Referring to FIG. 24, Panel A, the basic structure of the lock and dock sequence is shown. Tetraloop GNRA (GAAA) docking with its docking sequence generates an extremely stable structure. Sequences shown in FIG. 24, Panel A, are presented below:

```
                                      (SEQ ID NO: 28)
gaaa (SEQ ID NO: 29)
gauauggau (SEQ ID NO: 30)
guccuaaguc (SEQ ID NO: 31)
caggggaaacuuug
```

The use of a scaffold comprising a docked tetraloop as a crystallography scaffold is provided (FIG. 24, Panel B). The sequence shown in FIG. 24, Panel B, is presented below:

```
                                      (SEQ ID NO: 32)
cauuagcuaaggaugaaagucuaugcuaaug
```

A lock and dock structure in accordance with disclosed embodiments is shown in FIG. 24, Panel C. Inserts (hairpins or non-hairpin sequences) may be added to the restriction site at the identified additional insert location. Circled bases are docking sequences for the tetraloop. The sequence shown in FIG. 24, Panel C, is presented below:

```
                                      (SEQ ID NO: 33)
gcaccuaaggcgucagggucuagacccugcucaggggaaacuuugucgcua uggugc
```

Stabilizing the local 3'UTR structure is detrimental; however insertion of a destabilizing insert nearby restores viability. Referring to FIG. 25, Panel A, a representation of CYVaV-wt is shown. CYVaV-wt 3'stb is the parental stabilized construct containing 6 nt changes converting G:U pairs to G:C pairs. Two insertions of 60 nucleotides were added to the stabilized parental construct at positions 2319 and 2330 forming CY2319PDS60_3'stb and CY2330PDS60_3' stb. Nucleotide changes made to stabilize the structure and generate CYVaV-wt 3'stb are circled in Panel B. The sequences shown in FIG. 25, Panel B, is presented below:

```
                                      (SEQ ID NO: 34)
ggcuaguuaaucucauucgugggauggacaggcagccugacguugac (unmodified G:U pairs)
                                      (SEQ ID NO: 35)
guuaauguaggugucuuuccguaucuaguc (converted G:C pairs)
                                      (SEQ ID NO: 36)
gucaacgcaggugccuguccguaucuagcc
```

Targets for Treatment and Management

An anti-biotic insert for delivery by the disclosed vector is provided, which comprises either an enzybiotic or small peptide engineered to destroy the CLas bacterium. Enzybiotics prefer sugar rich, room temperature environments such as found in the plant phloem. The enzybiotic is translated in companion cells during the engineered CYVaV infection cycle. Proteins produced in the cytoplasm of the phloem are naturally able to exit into the sieve element (the default pathway for translated proteins), where CLas and other plant pathogenic bacteria take up residence. In the sieve element, the enzyme molecules move with the photo-assimilate up and down the trunk and lyse any bacteria upon contact. Since enzybiotics are targeted towards a specific class of bacteria, they preferably do not disturb the microbiome of the host tree. Various agents that target CLas have been developed (e.g., Hailing Jin, University of California, Riverside, CA). Thus, numerous inserts that target CLas bacterium are known in the art and may be utilized with the CYVaV vectors of the present disclosure.

As a further embodiment, it can be beneficial to target multiple pathways for destroying the disease and the disease psyllid vector. As a result, in certain embodiments the disclosed vectors include the enzybiotic and/or peptides described above, as well as inserts that trigger the production of siRNAs that interfere with either gene expression of the tree or the disease-carrying psyllid. In the case of the ACP, the RNA could kill the vector or render it wingless and thus harmless.

CYVaV-Based Vector Targeting Expression of Callose Synthase.

A vector comprising an RNA insert is provided that triggers the reduction of callose production and build-up in a host tree. A sufficiently large amount of the gene that produces callose in the phloem in response to bacteria is silenced via insertion of an siRNA sequence that is excised by the plant.

CYVaV-based vector may be utilized as a virus-induced gene-silencing (VIGS) vector to down-regulate expression of callose synthase in the phloem. VIGS has been widely used to down-regulate gene expression in mature plants to examine plant functional genomics (Senthil-Kumar et al. (2008). Virus-induced gene silencing and its application in characterizing genes involved in water-deficit-stress tolerance. J Plant Physiol 165(13):1404-1421). A complementary sequence is inserted into CYVaV at a suitable location as identified above (either anti-sense or a RNase III-cleavable hairpin). A citrus version of the gene is known (Enrique et al. (2011). Novel demonstration of RNAi in citrus reveals importance of citrus callose synthase in defense against *Xanthomonas citri* subsp. *citri*. Plant Biotech J 9:394-407).

Callose is a β 1,3-glucan that is synthesized in various tissues during development and biotic and abiotic stress (Chen, X. Y. and Kim, J. Y. (2009). Callose synthesis in higher plants. Plant Sig Behav 4(6):489-492). Deposition of callose in the sieve plates of sieve elements inhibits photoassimilate flow in the phloem, leading to over accumulation of callose in chloroplasts, which contributes to the death of trees during bacterial infections such as HLB (Koh, H. et al. (2012). Silent information Regulator 2 (Sir2) and Forkbead Box O (FOXO) Complement Mitochondrial Dysfunction and Dopaminergic Neuron Loss in *Drosophila* PTEN-induced Kinase 1 (PINK1) Null Mutant. J Biol Chem 287(16):12750-12758). All plants contain 12-14 callose synthase genes; one member of this gene family, CalS7 (*Arabidopsis* nomenclature), is mostly responsible for rapid callose deposition in sieve pores of the phloem in response to wounding and various pathogens (Xie et al. (2011). CalS7 encodes a callose synthase responsible for callose deposition in the phloem. Plant J 65(1):1-14). Complete inhibition of GSL7 impacted both normal phloem transport and inflorescence development in *Arabidopsis* (Barratt et al. (2011). Callose Synthase GSL7 Is Necessary for Normal Phloem Transport and Inflorescence Growth in *Arabidopsis*. Plant Physiol 155(1):328-341). A CYVaV-based vector is utilized to down-regulate the *N. benthamiana* and orange tree orthologues of CalS7 in mature plants in order to investigate the consequences of reduced (but not eliminated) sieve plate callose deposition. Alternatively, or in addition, the vector provides for an insert that expresses a callose-degrading enzyme.

In some embodiments, an insert is provided that targets one or more virus and/or fungal pathogen. In some embodiments, a hairpin insert is provided that generates an siRNA that directly targets CVEV, since CVEV is known to slightly intensify the yellowing impacts of CYVaV and to enable transport of CYVaV between trees. In some embodiments, a hairpin insert is provided that targets CTV, since CTV is a highly destructive viral pathogen of citrus (second only to CLas). In other embodiments, an insert is provided that targets another citrus (or other) virus. In some embodiments, an insert is provided that targets a fungal pathogen(s), given such pathogen(s) is able to take up siRNAs from the phloem.

In some embodiments, the CYVaV-based (or other iRNA) vector includes an insert(s) engineered to modify a phenotypic property of a plant that emanates from gene expression in companion cells. In one implantation, an insert is provided that triggers dwarfism, so that the fruit is easier to harvest and growth space requirements are reduced. Additional and/or other traits may also be targeted as desired. The iRNA vectors of the present disclosure comprising 1, 2, 3 or more inserts demonstrate stability and functionality.

All identified publications and references mentioned in this specification are herein incorporated by reference to the same extent as if each individual publication was specifically and individually indicated to be incorporated by reference in its entirety. While the invention has been described in connection with exemplary embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the features hereinbefore set forth.

What is claimed is:

1. A plus sense single stranded ribonucleic acid (RNA) vector consisting essentially of SEQ ID NO:1 with one or more heterologous segment(s) inserted therein.

2. The RNA vector of claim 1 wherein the heterologous segment(s) is located between an ORF encoding an RdRp and a 3' CITE of SEQ ID NO:1.

3. The RNA vector of claim 2, wherein said 3' CITE comprises the nucleic acid sequence(s) of SEQ ID NO: 4 and/or SEQ ID NO: 5.

4. The RNA vector of claim 2, wherein said 3' CITE comprises the nucleic acid sequence of SEQ ID NO: 3.

5. The RNA vector of claim 1, which is functionally stable for replication, movement and/or translation within the host plant for at least one month after infection thereof.

6. The RNA vector of claim 1, wherein said heterologous segment(s) comprises a polynucleotide that encodes at least one polypeptide selected from the group consisting of a reporter molecule, a peptide, and a protein.

7. The RNA vector of claim 6, wherein said polypeptide is an insecticide, an antibacterial, an antiviral, or an antifungal.

8. The RNA vector of claim 7, wherein said antibacterial is an enzybiotic.

9. The RNA vector of claim 7, wherein said antibacterial targets a bacterium Candidatus Liberibacter species.

10. The RNA vector of claim 9, wherein said Candidatus Liberibacter species is Candidatus Liberibacter asiaticus (CLas).

11. The RNA vector of claim 1, wherein said heterologous segment(s) comprises a small non-coding RNA molecule and/or an RNA interfering molecule.

12. The RNA vector of claim 11, wherein said small non-coding RNA molecule and/or said RNA interfering molecule targets an insect vector, a virus, or a fungus.

13. The RNA vector of claim 12, wherein said small non-coding RNA molecule and/or said RNA interfering molecule targets a nucleic acid of said insect vector, said virus, or said fungus.

14. The RNA vector of claim 12, wherein said targeted virus is selected from the group consisting of Citrus vein enation virus (CVEV) and Citrus tristeza virus (CTV).

15. The RNA vector of claim 1, wherein said heterologous segment(s) comprises a polynucleotide that encodes for a protein or peptide that alters a phenotypic trait.

16. The RNA vector of claim 15, wherein said phenotypic trait is selected from the group consisting of pesticide tolerance, herbicide tolerance, insect resistance, reduced callose production, increased growth rate, and dwarfism.

17. A host plant comprising the RNA vector of claim 1, wherein said host plant is a whole plant, a plant organ, a plant tissue, or a plant cell.

18. The host plant of claim 17, wherein said host plant is in a genus selected from the group consisting of citrus, vitis, ficus and olea.

19. The host plant of claim 18, wherein said host plant is a citrus tree or a citrus tree graft.

20. A method for introducing a heterologous segment(s) into a host plant comprising introducing into said host plant the RNA vector of claim 1.

21. The method of claim 20, wherein said introducing step comprises grafting a plant organ or plant tissue of a plant that comprises the RNA vector to a plant organ or plant tissue of another plant that does not comprise the RNA vector prior to said introduction.

22. The method of claim 20, wherein the RNA vector systemically infects the host plant.

23. The method of claim 20, wherein said host plant is in a genus selected from the group consisting of citrus, vitis, ficus and olea.

24. The RNA vector of claim 1, wherein the ORF that encodes a RNA-dependent RNA polymerase (RdRp) comprises conserved polynucleotide sequences having the nucleic acid sequence of: SEQ ID NO:10, SEQ ID NO:11, SEQ ID NO:12, SEQ ID NO:13and SEQ ID NO:14.

25. The RNA vector of claim 24, wherein said ORF further comprises conserved polynucleotide sequences having the nucleic acid sequence of: SEQ ID NO:15 and SEQ ID NO:16.

26. The RNA vector of claim 1, comprising conserved polynucleotide sequences having the nucleic acid sequence of: SEQ ID NO: 10, SEQ ID NO: 11, SEQ ID NO: 12, SEQ ID NO: 13, SEQ ID NO: 14, SEQ ID NO:15 and/or SEQ ID NO:16.

27. The RNA vector of claim 1, comprising conserved polynucleotide sequences having the nucleic acid sequence of: SEQ ID NO: 10, SEQ ID NO: 11, SEQ ID NO: 12, SEQ ID NO: 13, SEQ ID NO: 14, SEQ ID NO:15 and SEQ ID NO:16.

28. The RNA vector of claim 1, wherein the heterologous segment(s) is inserted between positions corresponding to positions 2158 and 2468 of SEQ ID NO:1.

\* \* \* \* \*